United States Patent
Shirai et al.

(10) Patent No.: US 10,660,827 B2
(45) Date of Patent: May 26, 2020

(54) SOLID POWDERY COSMETIC COMPOSITION

(71) Applicant: L'OREAL, Paris (FR)

(72) Inventors: Masako Shirai, Kawasaki (JP); Caroline Lebre-Lemonnier, Tokyo (JP); Padraig MacDermott, Meudon (FR); Hiroyo Kameyama, Kawasaki (JP); Kana Nakayama, Kawasaki (JP)

(73) Assignee: L'OREAL, Paris (FR)

( * ) Notice: Subject to any disclaimer, the term of this patent is extended or adjusted under 35 U.S.C. 154(b) by 70 days.

(21) Appl. No.: 15/954,989

(22) Filed: Apr. 17, 2018

(65) Prior Publication Data

US 2018/0250202 A1 Sep. 6, 2018

Related U.S. Application Data

(63) Continuation of application No. 14/648,921, filed as application No. PCT/IB2012/002821 on Dec. 4, 2012, now abandoned.

(51) Int. Cl.

| | |
|---|---|
| *A61K 8/02* | (2006.01) |
| *A61K 8/73* | (2006.01) |
| *A61K 8/25* | (2006.01) |
| *A61K 8/92* | (2006.01) |
| *A61K 8/81* | (2006.01) |
| *A61K 8/90* | (2006.01) |
| *A61K 8/898* | (2006.01) |
| *A61K 8/891* | (2006.01) |
| *A61K 8/87* | (2006.01) |
| *A61Q 1/12* | (2006.01) |
| *A61Q 1/10* | (2006.01) |

(52) U.S. Cl.
CPC .............. *A61K 8/022* (2013.01); *A61K 8/25* (2013.01); *A61K 8/732* (2013.01); *A61K 8/8111* (2013.01); *A61K 8/8117* (2013.01); *A61K 8/8152* (2013.01); *A61K 8/87* (2013.01); *A61K 8/891* (2013.01); *A61K 8/898* (2013.01); *A61K 8/90* (2013.01); *A61K 8/92* (2013.01); *A61Q 1/10* (2013.01); *A61Q 1/12* (2013.01)

(58) Field of Classification Search
CPC .......... A61K 8/022; A61K 8/732; A61K 8/25; A61K 8/92; A61K 8/8111; A61K 8/8117; A61K 8/90; A61K 8/898; A61K 8/891; A61K 8/87; A61K 8/8152; A61Q 1/12; A61Q 1/10
See application file for complete search history.

(56) References Cited

U.S. PATENT DOCUMENTS

| | | |
|---|---|---|
| 2,676,182 A | 4/1954 | Daudt et al. |
| 3,627,851 A | 12/1971 | Brady |
| 3,772,247 A | 11/1973 | Flannigan |
| 4,935,484 A | 6/1990 | Wolfgruber et al. |
| 5,061,481 A | 10/1991 | Suzuki et al. |
| 5,082,706 A | 1/1992 | Tangney |
| 5,110,890 A | 5/1992 | Butler |
| 5,219,560 A | 6/1993 | Suzuki et al. |
| 5,221,534 A | 6/1993 | DesLauriers et al. |
| 5,248,739 A | 9/1993 | Schmidt et al. |
| 5,302,685 A | 4/1994 | Tsumura et al. |
| 5,319,040 A | 6/1994 | Wengrovius et al. |
| 5,817,302 A | 10/1998 | Berthiaume et al. |
| 5,851,517 A | 12/1998 | Mougin et al. |
| 5,874,069 A | 2/1999 | Mendolia et al. |
| 5,919,441 A | 7/1999 | Mendolia et al. |
| 5,981,680 A | 11/1999 | Petroff et al. |
| 6,051,216 A | 4/2000 | Barr et al. |
| 6,254,877 B1 | 7/2001 | De La Poterie et al. |
| 6,491,927 B1 | 12/2002 | Arnaud et al. |
| 6,682,748 B1 | 1/2004 | De La Poterie et al. |
| 7,803,877 B2 | 9/2010 | Lion et al. |
| 7,915,347 B2 | 3/2011 | Lion et al. |

(Continued)

FOREIGN PATENT DOCUMENTS

| | | |
|---|---|---|
| EP | 0748746 A1 | 12/1996 |
| EP | 0749747 A1 | 12/1996 |

(Continued)

OTHER PUBLICATIONS

Office Action for counterpart U.S. Appl. No. 14/648,921, dated May 22, 2017.

(Continued)

*Primary Examiner* — Trevor Love

(74) *Attorney, Agent, or Firm* — The Marbury Law Group, PLLC

(57) ABSTRACT

The present invention relates to a cosmetic composition, comprising:

an oil phase in an amount of 20% by weight or more, preferably from 28% to 45% by weight, relative to the total weight of the composition, said oil phase including preferably at least one non-volatile oil, a pulverulent phase in an amount of 40% by weight or more, preferably from 55% to 70% by weight, relative to the total weight of the composition, at least one hydrophobic film-forming polymer, the cosmetic composition is obtainable, and preferably obtained, by a process comprising the steps of:

mixing said oil phase, said hydrophobic film-forming polymer(s), said pulverulent phase, and at least one additional solvent to prepare a slurry; and shaping said slurry in a container by compression and/or aspiration to prepare the cosmetic composition.

20 Claims, No Drawings

(56) References Cited

U.S. PATENT DOCUMENTS

| | | |
|---|---|---|
| 8,658,141 B2 | 2/2014 | Bui et al. |
| 9,089,503 B2 | 7/2015 | Bui et al. |
| 2002/0055562 A1 | 5/2002 | Butuc |
| 2004/0120920 A1 | 6/2004 | Lion et al. |
| 2004/0146473 A1 | 7/2004 | Lion |
| 2004/0156812 A1 | 8/2004 | Lion |
| 2005/0069508 A1 | 3/2005 | Pays et al. |
| 2005/0183511 A1 | 8/2005 | Giron |
| 2006/0127341 A1 | 6/2006 | Lion et al. |
| 2006/0134034 A1 | 6/2006 | Blin et al. |
| 2006/0251601 A1 | 11/2006 | Arnaud |
| 2007/0009456 A1 | 1/2007 | Delacour et al. |
| 2008/0171006 A1 | 7/2008 | Bui et al. |
| 2008/0305061 A1 | 12/2008 | Bui et al. |
| 2009/0004125 A1 | 1/2009 | Lion |
| 2011/0171151 A1 | 7/2011 | Arnaud et al. |
| 2011/0236331 A1 | 9/2011 | Vic et al. |
| 2014/0010775 A1 | 1/2014 | Sonoyama et al. |
| 2016/0045427 A1 | 2/2016 | Vic et al. |

FOREIGN PATENT DOCUMENTS

| | | |
|---|---|---|
| EP | 0923928 A1 | 6/1999 |
| EP | 0930060 A1 | 7/1999 |
| EP | 0963751 A2 | 12/1999 |
| EP | 1034776 A1 | 9/2000 |
| JP | 56-108703 A | 8/1981 |
| JP | 05-017710 A | 1/1993 |
| JP | 07-258460 A | 10/1995 |
| JP | 09-171154 A | 6/1997 |
| JP | 09-188830 A | 7/1997 |
| JP | 10-158450 A | 6/1998 |
| JP | 10-158451 A | 6/1998 |
| JP | 10-158541 A | 6/1998 |
| JP | 11-001530 A | 1/1999 |
| JP | 2004-149772 A | 5/2004 |
| JP | 2005-053915 A | 3/2005 |
| JP | 2008-189663 A | 8/2008 |
| JP | 2008-214264 A | 9/2008 |
| JP | 2008-303220 A | 12/2008 |
| JP | 2011-207880 A | 10/2011 |
| JP | 2012-502018 A | 1/2012 |
| JP | 2012-197241 A | 10/2012 |
| WO | 03/045337 A1 | 6/2003 |
| WO | 03/045377 A1 | 6/2003 |
| WO | 2004/055081 A2 | 7/2004 |
| WO | 2005/075542 A1 | 8/2005 |
| WO | 2010/105952 A2 | 9/2010 |
| WO | 2012/035513 A1 | 3/2012 |
| WO | 2012/066457 A1 | 5/2012 |
| WO | WO2012/066457 * 5/2012 ............ A61K 8/891 |
| WO | 2012/087453 A1 | 6/2012 |
| WO | 2012/163984 A2 | 12/2012 |

OTHER PUBLICATIONS

Final Office Action for counterpart U.S. Appl. No. 14/648,921, dated Sep. 5, 2017.

Office Action for counterpart U.S. Appl. No. 14/648,921, dated Dec. 18, 2017.

International Search Report for PCT/IB2012/002821 dated Oct. 2, 2013.

Japanese Office Action for Application No. 2015-544546, dated Dec. 19, 2016 (with English translation).

English language abstract for EP 1034776 (Sep. 13, 2000).

English machine translation for JP 05-017710 (Jan. 26, 1993).

English language abstract for JP 56-108703 (Aug. 28, 1981).

English machine translation for JP 07-258460 (Oct. 9, 1995).

English language abstract for JP 09-171154 (Jun. 30, 1997).

English machine translation for JP 09-188830 (Jul. 22, 1997).

English machine translation for JP 10-158450 (Jun. 16, 1998).

English machine translation for JP 10-158451 (Jun. 16, 1998).

English machine translation for JP 11-001530 (Jan. 6, 1999).

* cited by examiner

SOLID POWDERY COSMETIC COMPOSITION

CROSS REFERENCE TO RELATED APPLICATIONS

This application is a continuation of U.S. application Ser. No. 14/648,921, filed Jun. 2, 2015, the contents of which are incorporated here by reference. This application claims the benefit of PCT/IB2012/002821, filed internationally on Dec. 4, 2012, which is incorporated herein by reference.

The present invention relates to a cosmetic composition, in particular a solid powdery cosmetic composition, in particular to a pressed powdery composition prepared by a wet process.

Skin make up cosmetics may commonly be used to give an attractive color to the skin, such as the face, but also to mask skin imperfections, such as redness, marks and wrinkles.

The makeup powdery cosmetics may be in the form of a loose powdery cosmetic composition or a compacted powdery cosmetic composition.

The loose powdery compositions generally include only pulverulent phase comprising different types of particles or a pulverulent phase accompanied with a very small amount of fatty phase (oil(s)) representing generally 2 or 3% by weight compared to the total weight of the composition).

The compact powdery composition generally includes a pulverulent phase and a fatty phase which are respectively present according to a respective total amount such that the weight ratio of the pulverulent phase and the fatty phase is about 90/10. Generally the fatty phase incorporates a liquid fatty phase (oil phase) which plays the role of a binder for the pulverulent phase, allowing thus to aggregate the particles comprised in the pulverulent phase in view of compacting the resulting composition into a make-up pan.

A typical method to make a compacted powdery cosmetic composition such as a powdery foundation or an eyeshadow is generally a dry process. However according to a minority way of preparing such powdery compositions, wet process may be used.

In the dry process, the pulverulent phase and the oil phase are mixed together and compacted to about 100 hundred bars into a make-up pan in the form of a compacted powder, for instance by an electric motor, a hydraulic ram or a pneumatic cylinder.

In the wet process, an additional volatile solvent is added to the pulverulent phase and the oil phase so as to form a slurry able to be compacted in the form of a compacted powder. The volatile solvent is eliminated from the composition. Generally, the quantity of oil phase into the composition is low (10% or less) so as to obtain a good compacting of the powder via the mechanical means above-cited and allows to the composition not to overflow from the pan.

Such a technical concern generally obliges the formulators of compacted powder compositions to limit the amount of oil phase in order to have a good compacting of the powder and avoid any overflow from the pan during this compacting process.

However a composition with a high amount of powder may have the drawback to be fragile and not resist against impact.

Furthermore a composition with a high amount of powder may not have optimized sensorial properties, when the composition is picked-up in the compact and/or applied onto the skin.

Moreover given the large amount of pulverulent phase in such powdery cosmetic composition, it is quite difficult for the formulators to obtain a good wearing of the composition onto the skin, except acting on the components of the pulverulent phase. Additionally, another way which could consist in increasing the amount of oil phase for playing onto the wearing properties of such powdery composition may be considered as complicated because the high level of oil phase into a powdery composition might give them difficult to be compacted as well as might provoke said powdery composition to "wax", that is to say the composition might harden during its storage preventing the user from picking-up said composition.

At the last, some powdery cosmetic compositions may not show satisfying cosmetic properties as well as long lasting cosmetic effects, for instance due to the secretion of sweat and sebum from the skin, and the like.

An objective of the present invention is to provide a cosmetic composition which can provide long lasting cosmetic effects even if the cosmetic composition includes a substantial amount of powder.

Others objectives of the present invention are to provide a cosmetic composition which can provide at least one of the following properties:
  good cohesion and homogenization of the composition,
  good resistance to impact,
  good texture of the composition,
  convenient hardness of the composition,
  good pick-up properties (in term of quantity),
  comfort to be wear (without drying effect onto the skin),
  improved lasting cosmetic effects while maintaining a substantial amount of powder in the composition for keeping the powdery effect associated with such compositions,
  good sensoriality at the time of picking-up the composition (softness effect),
  good sensoriality at the time of applying the composition.

The objective of the present invention can be realized by a cosmetic composition, preferably a solid powdery composition, comprising:
  an oil phase in an amount of 20% by weight or more, preferably from 25% to 50% by weight, and more preferably from 28% to 40% by weight, relative to the total weight of the composition, said oil phase including preferably at least one non-volatile oil, more preferably at least one non-volatile hydrocarbon-based oil and/or at least one non-volatile silicone oil, still more preferably at least one non-volatile hydrocarbon-based oil and at least one non-volatile silicone oil,
  a pulverulent phase in an amount of 40% by weight or more, preferably from 50% to 75% by weight, and more preferably from 55% to 70% by weight, relative to the total weight of the composition,
  at least one hydrophobic film-forming polymer,
  the cosmetic composition is obtainable, and preferably obtained, by a process, called wet process, comprising the steps of:
    mixing said oil phase, said hydrophobic film-forming polymer(s), said pulverulent phase, and at least one additional solvent to prepare a slurry; and
    shaping said slurry in a container by compression and/or aspiration to prepare the cosmetic composition, preferably by compression and aspiration.

Preferably, the cosmetic composition according to the invention is a make-up composition including at least one colouring agent.

The oil phase and the hydrophobic film-forming polymer(s) form the fatty phase or binder of the composition, preferably they both form a liquid fatty phase of the composition, to be mixed to the pulverulent phase and to the additional solvent.

Preferably a composition according to the invention is a pressed cosmetic composition, that is to say that the shaping of the composition is obtained by pressing it between 2 and 100 bars, more preferably between 2 and 50 bars.

Such a cosmetic composition allows to solve at least one of the previous cited technical problems and preferentially every mentioned technical problem.

The hydrophobic film-forming polymer can be selected from the group consisting of polyamide-silicone block polymers, silicone resins, block ethylenic polymers, vinyl polymers comprising at least one carbosiloxane dendrimer derivative, copolymers comprising carboxylate groups and polydimethylsiloxane groups, lipodispersible polymer in the form of a non-aqueous dispersion of polymer particles, olefin copolymers selected from amorphous olefin copolymers and olefin copolymers with controlled and moderate crystallization, hydrocarbon-based resins having a number-average molecular weight of less than or equal to 10000 g/mol, and a mixture thereof.

The polyamide-silicone block polymer may comprise a polyamide-silicone block copolymer comprising at least one unit of formula (III) or (IV):

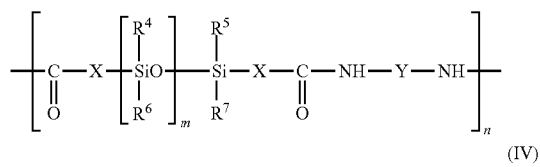
(III)

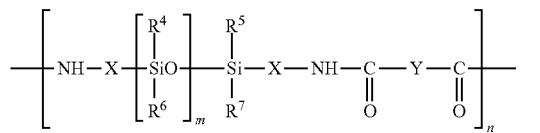
(IV)

in which:
1) $R^4$, $R^5$, $R^6$ and $R^7$, which may be identical or different, represent a group chosen from:
   linear, branched or cyclic, saturated or unsaturated, $C_1$ to $C_{40}$ hydrocarbon-based groups, possibly containing in their chain one or more oxygen, sulfur and/or nitrogen atoms, and possibly being partially or totally substituted with fluorine atoms,
   $C_6$-$C_{10}$ aryl groups, optionally substituted with one or more $C_1$-$C_4$ alkyl groups,
   polyoganosiloxane chains possibly containing one or more oxygen, sulfur and/or nitrogen atoms,
2) the groups X, which may be identical or different, represent a linear or branched $C_1$-$C_{30}$ alkylenediyl group, possibly containing in its chain one or more oxygen and/or nitrogen atoms;
3) Y is a saturated or unsaturated $C_1$ to $C_{50}$ linear or branched alkylene, arylene, cycloalkylene, alkylarylene or arylalkylene divalent group, which may comprise one or more oxygen, sulfur and/or nitrogen atoms, and/or may bear as substituent one of the following atoms or groups of atoms: fluoro, hydroxyl, $C_3$ to $C_8$ cycloalkyl, $C_1$ to $C_{40}$ alkyl, $C_5$ to $C_{10}$ aryl, phenyl optionally substituted with 1 to 3 $C_1$ to $C_3$ alkyl, $C_1$ to $C_3$ hydroxyalkyl and $C_1$ to $C_6$ aminoalkyl groups, or 4) Y represents a group corresponding to the formula:

in which:
T represents a linear or branched, saturated or unsaturated, $C_3$-$C_{24}$ trivalent or tetravalent hydrocarbon-based group optionally substituted with a polyorganosiloxane chain, and possibly containing one or more atoms chosen from O, N and S, or T represents a trivalent atom chosen from N, P and Al, and $R^8$ represents a linear or branched $C_1$-$C_{50}$ alkyl group or a polyorganosiloxane chain, possibly comprising one or more ester, amide, urethane, thiocarbamate, urea, thiourea and/or sulfonamide groups, which may possibly be linked to another chain of the polymer; and 5) n is an integer ranging from 2 to 500 and preferably from 2 to 200, and m is an integer ranging from 50 to 1000, preferably from 50 to 700 and better still from 50 to 200.

The silicone resin may be selected from the group consisting of polymethylsilsesquioxanes and siloxysilicate resins, in particular trimethyl siloxysilicate resins.

The block ethylenic polymer may be a block ethylenic copolymer comprising at least a first block with a glass transition temperature (Tg) of greater than or equal to 40° C. and being totally or partly derived from one or more first monomers, which are such that the homopolymer prepared from these monomers has a glass transition temperature of greater than or equal to 40° C., and at least a second block with a glass transition temperature of less than or equal to 20° C. and being derived totally or partly from one or more second monomers, which are such that the homopolymer prepared from these monomers has a glass transition temperature of less than or equal to 20° C., the said first block and the said second block being connected together via a statistical intermediate segment comprising at least one of the said first constituent monomers of the first block and at least one of the said second constituent monomers of the second block, and the said block copolymer having a polydispersity index I of greater than 2.

The block ethylenic copolymer may preferably be such that the said first block is obtained from at least one acrylate monomer of formula $CH_2=CH-COOR^2$ in which $R^2$ represents a $C_4$ to $C_{12}$ cycloalkyl group and from at least one methacrylate monomer of formula $CH_2=C(CH_3)-COOR'_2$ in which $R'_2$ represents a $C_4$ to $C_{12}$ cycloalkyl group, and the said second block being obtained from at least a second monomer with a glass transition temperature of less than or equal to 20° C. and from an additional monomer, preferably acrylic acid.

The vinyl polymer comprising at least one carbosiloxane dendrimer derivative may comprise at least one carbosiloxane dendrimer-based unit and is the product of polymerization of (A) 0 to 99.9 parts by weight of a vinyl monomer; and
(B) 100 to 0.1 part by weight of a carbosiloxane dendrimer containing a radical-polymerizable organic group, represented by the formula:

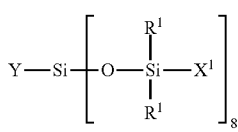

in which Y represents a radical-polymerizable organic group, $R^1$ represents an aryl group or an alkyl group containing from 1 to 10 carbon atoms, and $X^1$ represents a silylalkyl group which, when i=1, is represented by the formula:

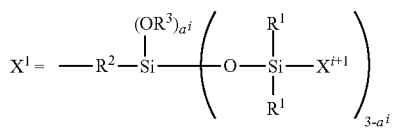

in which $R^1$ is the same as defined above, $R^2$ represents an alkylene group containing from 2 to 10 carbon atoms, $R^3$ represents an alkyl group containing from 1 to 10 carbon atoms, $X^{i+1}$ represents a hydrogen atom, an alkyl group containing from 1 to 10 carbon atoms, an aryl group, or the silylalkyl group defined above with i=i+1; i is an integer from 1 to 10 that represents the generation of the said silylalkyl group, and $a^i$ is an integer from 0 to 3; in which the said radical-polymerizable organic group Y contained in components (B) is chosen from the group formed by an organic group that contains a methacylic group or an acrylic group and that is represented by the formulae:

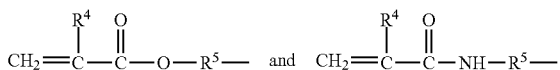

in which $R^4$ represents a hydrogen atom or an alkyl group, $R^5$ represents an alkylene group containing from 1 to 10 carbon atoms; and an organic group containing a styryl group and that is represented by the formula:

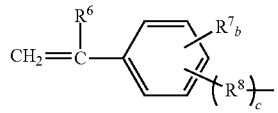

in which $R^6$ represents a hydrogen atom or an alkyl group, $R^7$ represents an alkyl group containing from 1 to 10 carbon atoms, $R^8$ represents an alkylene group containing from 1 to 10 carbon atoms, b is an integer from 0 to 4, and c is 0 or 1, such that if c is 0, —$(R^8)_c$— represents a bond.

The vinyl polymer comprising at least one carbosiloxane dendrimer derivative may preferably be an acylate/polytrimethyl siloxymethacrylate copolymer.

The copolymer comprising carboxylate groups and polydimethylsiloxane groups may be selected from the group consisting of copolymers of acrylic acid and of stearyl acrylate containing polydimethylsiloxane grafts, copolymers of stearyl methacylate containing polydimethylsiloxane grafts, copolymers of acrylic acid and of stearyl methacrylate containing polydimethylsiloxane grafts, copolymers of methyl methacrylate, butyl methacrylate, 2-ethylhexylacrylate and stearyl methacrylate containing polydimethylsiloxane grafts.

The amorphous olefin copolymer may preferably comprise at least one styrene block.

The amorphous olefin copolymer may preferably be selected from the group consisting of a styrene-ethylene/butylene-styrene triblock copolymer, a styrene-ethylene/butylene diblock copolymer, a styrene-ethylene/isoprene-styrene triblock copolymer, a styrene-ethylene/isoprene diblock copolymer, or a mixture thereof.

The hydrocarbon-based resin having a number-average molecular weight of less than or equal to 10 000 g/mol may be selected from indene hydrocarbon-based resins.

Preferably a composition according to the invention includes at least one film-forming polymer selected from olefin copolymers selected from amorphous olefin copolymers and olefin copolymers with controlled and moderate crystallization, hydrocarbon-based resin having a number-average molecular weight of less than or equal to 10 000 g/mol, and their mixture(s).

Preferably a composition according to the invention includes at least one film-forming polymer selected from olefin copolymers selected from amorphous olefin copolymers.

Preferably a composition according to the invention includes at least one film-forming polymer selected from olefin copolymers selected from amorphous copolymers including at least one styrene block and at least one olefin block.

The hydrophobic film-forming polymer may be present in an amount of 0.1% by weight or more, preferably from 0.5% to 15% by weight, and more preferably from 1.0% to 12% by weight relative to the total weight of the composition.

The oil phase may comprise at least one non-volatile silicone oil selected from phenyl silicone oils and non-phenyl linear silicone oils, preferably in an amount ranging from 1% to 35% by weight, preferably from 2% to 30% by weight, and according to a particular embodiment from 4% to 12% by weight, relative to the total weight of the composition.

The oil phase may comprise at least one non-volatile hydrocarbon-based oil selected from fatty esters represented by the formula RCOOR' wherein R denotes a $C_{1-29}$ fatty acid residue, and R' denotes $C_{2-30}$ hydrocarbon group, preferably in an amount ranging from 10% to 40% by weight, preferably from 12% to 35% by weight, and more preferably from 15% to 30% by weight, relative to the total weight of the composition.

The pulverulent phase may comprise at least one non-spherical filler preferably selected from the group consisting of talc, mica, silica, kaolin, sericite, calcinated talc, calcinated mica, calcinated sericite, synthetic mica, lauroyl lysine, metal soap, bismuth oxychloride, barium sulfate, boron nitride, calcium carbonate, magnesium carbonate, magnesium hydrogen carbonate, hydroxyapatite, and a mixture thereof.

The pulverulent phase may comprise at least one spherical filler, preferably selected from the group consisting of organic filler and silica, preferably selected from the group consisting of polyurethane powder, polyamide powder and silica.

The pulverulent phase may comprise at least one coloring agent, preferably at least one pearlescent pigment.

The amount of the oil phase and the amount of the pulverulent phase may be such that the weight ratio of the oil phase:the pulverulent phase is ranging from 20:80 to 45:55, preferably 25:75 to 40:60, and more preferably 30:70 to 38:62.

The amount of the oil phase and the amount of the hydrophobic film-forming polymer(s) may be such that the weight ratio of the oil phase:the hydrophobic film-forming polymer(s) is ranging from 98:2 to 70:30, preferably 95:5 to 80:20, and more preferably 91:9 to 75:25.

The mixing step in the wet process may include mixing the oil phase, the hydrophobic film-forming polymers(s), and the pulverulent phase, to form a mixture, and further mixing the at least one additional solvent with the mixture.

Alternatively, the mixing step in the wet process may include mixing the oil phase, the hydrophobic film-forming polymers(s) and the at least one additional solvent to form a mixture, and further mixing the pulverulent phase with the mixture.

The additional solvent may comprise a volatile solvent, preferably a volatile organic solvent.

The wet process may further comprise a step of drying the cosmetic composition, after the step of shaping.

The present invention also relates to a cosmetic process including a step of applying to skin, preferably face or eyelid, a cosmetic composition according to the present invention as explained above.

After diligent research, the inventors have discovered that it is possible to provide a cosmetic composition which can show long lasting cosmetic effects even if the cosmetic composition includes a substantial amount of powder, by preparing the cosmetic composition in accordance with a wet process using a relatively large amount of a liquid fatty substance.

Thus, the present invention is a cosmetic composition, comprising:

an oil phase in an amount of 20% by weight or more, preferably from 25% to 50% by weight, and more preferably from 28% to 45% by weight, relative to the total weight of the composition, said oil phase including preferably at least one silicone oil and at least one hydrocarbon-based oil, more preferably at least one non volatile silicone oil and at least one non volatile hydrocarbon-based oil; and a pulverulent phase in an amount of 40% by weight or more, preferably from 50% to 75% by weight, and more preferably from 55% to 70% by weight, relative to the total weight of the composition;

at least one hydrophobic film-forming polymer, and
the cosmetic composition is obtained by a wet process comprising the steps of:
mixing said liquid fatty phase, said pulverulent phase, and at least one additional solvent to prepare a slurry; and
shaping said slurry in a container by compression and/or aspiration to prepare the cosmetic composition.

The cosmetic composition according to the present invention can notably provide long lasting cosmetic effects and sensorial effects. Therefore, for example, the color on the skin does not substantially change for a long period of time; skin imperfections, such as redness, marks and wrinkles can be masked for a long period of time; the matt appearance of the skin is maintained for a long period of time. Furthermore, the make-up provided by the cosmetic composition according to the present invention can be well adhered onto the skin for a long period of time.

Hereinafter, the cosmetic composition according to the present invention will be explained in a more detailed manner.

[Oil Phase]

The cosmetic composition according to the present invention includes at least one oil phase. This oil phase advantageously serve as binder for the pulverulent phase described later. Such an oil phase preferably comprises at least one non-volatile oil.

The term "oil" means a water-immiscible non-aqueous compound that is liquid at room temperature (25° C.) and at atmospheric pressure (760 mmHg).

The term "non-volatile oil" means an oil that remains on a keratin substance such as skin and hair at room temperature and pressure. More precisely, a non-volatile oil has an evaporation rate strictly less than 0.01 mg/cm$^2$/min.

A cosmetic composition according to the present invention advantageously has a content of oil phase and in particular of non-volatile oil(s), of greater than or equal to 20% by weight, preferably from 25% to 50% by weight, and more preferably from 28% to 40% by weight, relative to the total weight of the composition.

The oil phase may preferably include at least one non-volatile hydrocarbon-based oil and/or at least one non-volatile silicone oil, preferably at least one non-volatile hydrocarbon-based oil and at least one non-volatile silicone oil.

The at least one non-volatile hydrocarbon-based oil and the at least one non-volatile silicone oil are advantageously present in the composition according to a respective total amount such that weight of the non-volatile hydrocarbon-based oil(s) and the non-volatile silicone oil(s) greater than or equal to 1, more preferably greater than or equal to 2, preferably inclusively comprised between 1.5 and 10, preferably between 1.8 and 6.

(Non-Volatile Hydrocarbon-Based Oil)

The oil phase of a cosmetic composition according to the present invention advantageously comprise one or more non-volatile hydrocarbon-based oils.

As the non-volatile hydrocarbon-based oils, mention may be made of:

hydrocarbon-based oils of plant origin, such as phytostearyl esters, such as phytostearyl oleate, phytostearyl isostearate and lauroyl/octyldodecyl/phytostearyl glutamate; triglycerides formed from fatty acid esters of glycerol, in particular whose fatty acids may have chain lengths ranging from $C_{18}$ to $C_{36}$, these oils possibly being linear or branched, and saturated or unsaturated; these oils may especially be heptanoic or octanoic triglycerides, shea oil, alfalfa oil, poppy oil, pumpkin oil, millet oil, barley oil, quinoa oil, rye oil, candlenut oil, passionflower oil, shea butter oil, aloe oil, sweet almond oil, peach stone oil, groundnut oil, argan oil, avocado oil, baobab oil, borage oil, broccoli oil, calendula oil, camellina oil, carrot oil, safflower oil, hemp oil, rapeseed oil, cottonseed oil, coconut oil, marrow seed oil, wheatgerm oil, jojoba oil, lily oil, macadamia oil, corn oil, meadowfoam oil, St-John's wort oil, monoi oil, hazelnut oil, apricot kernel oil, walnut oil, olive oil, evening primrose oil, palm oil, blackcurrant pip oil, kiwi seed oil, grape seed oil, pistachio oil, pumpkin oil, quinoa oil, musk rose oil, sesame oil, soybean oil, sunflower oil, castor oil and watermelon oil, and mixtures thereof or alternatively caprylic/capric acid triglycerides, such as those sold by the company Stéarineries Dubois or those sold under the names Miglyol 810®, 812® and 818® by the company Dynamit Nobel;

synthetic ethers containing from 10 to 40 carbon atoms;
synthetic esters, for instance the oils of formula $R_1COOR_2$, in which $R_1$ represents at least one linear or branched fatty acid residue containing from 1 to 40 carbon atoms and $R_2$ represents a hydrocarbon-based chain, which is especially branched, containing from 1 to 40 carbon atoms, on condition that $R_1+R_2 \geq 10$. The esters may be chosen especially from fatty acid esters of alcohols, for instance cetostearyl octanoate, isopropyl alcohol esters, such as isopropyl myristate, isopropyl palmitate, ethyl palmitate, 2-ethylhexyl palmitate, isopropyl stearate, isopropyl isostearate, isostearyl isostearate, octyl stearate, hydroxylated esters, for instance isostearyl lactate, octyl hydroxystearate, diisopropyl adipate, heptanoates, and especially isostearyl heptanoate, alcohol or polyalcohol octanoates, decanoates or ricinoleates, for instance propylene glycol dioctanoate, cetyl octanoate, tridecyl octanoate, 2-ethylhexyl 4-diheptanoate, 2-ethylhexyl palmitate, alkyl benzoates, notably $C_{12}$-$C_{15}$ alkyl benzoates, polyethylene glycol diheptanoate, propylene glycol 2-diethylhexanoate, and mixtures thereof hexyl laurate, neopentanoic acid esters, for instance isodecyl neopentanoate, isotridecyl neopentanoate, isostearyl neopentanoate, octyldodecyl neopentanoate, isononanoic acid esters, for instance isononyl isononanoate, isotridecyl isononanoate, octyl isononanoate, hydroxylated esters, for instance isostearyl lactate and diisostearyl malate;

polyol esters and pentaerythritol esters, for instance dipentaerythrityl tetrahydrostearate/tetraisostearate;

esters of diol dimers and of diacid dimers;

copolymers of diol dimer and of diacid dimer and esters thereof such as dilinoleyl diol dimer/dilinoleic dimer copolymers, and esters thereof;

copolymers of polyols and of diacid dimers, and esters thereof;

fatty alcohols that are liquid at room temperature, with a branched and/or unsaturated carbon-based chain containing from 12 to 26 carbon atoms, for instance 2-octyldodecanol, isostearyl alcohol, oleyl alcohol, 2-hexyldecanol, 2-butyloctanol and 2-undecylpentadecanol;

$C_{12}$-$C_{22}$ higher fatty acids, such as oleic acid, linoleic acid and linolenic acid, and mixtures thereof;

dialkyl carbonates, the two alkyl chains possibly being identical or different, such as dicaprylyl carbonate; and oils with a molar mass of between about 400 and about 10 000 g/mol, in particular about 650 to about 10 000 g/mol, in particular from about 750 to about 7500 g/mol and more particularly ranging from about 1000 to about 5000 g/mol; mention may be made especially, alone or as a mixture, of (i) lipophilic polymers such as polybutylenes, polyisobutylenes, for example hydrogenated, polydecenes and hydrogenated polydecenes, vinylpyrolidone copolymers, such as the vinylpyrolidone/1-hexadecene copolymer, and polyvinylpyrrolidone (PVP) copolymers, such as the copolymers of a $C_2$-$C_{30}$ alkene, such as $C_3$-$C_{22}$, and combinations thereof; (ii) linear fatty acid esters containing a total carbon number ranging from 35 to 70, for instance pentaerythrityl tetrapelargonate; (iii) hydroxylated esters such as polyglyceryl-2 triisostearate; (iv) aromatic esters such as tridecyl trimellitate; (v) esters of fatty alcohols or of branched $C_{24}$-$C_{28}$ fatty acids, such as those described in U.S. Pat. No. 6,491,927 and pentaerythritol esters, and especially triisoarachidyl citrate, pentaerythrityl tetraisononanoate, glyceryl triisostearate, glyceryl 2-tridecyltetradecanoate, pentaerythrityl tetraisostearate, poly(2-glyceryl) tetraisostearate or pentaerythrityl 2-tetradecyltetradecanoate; (vi) diol dimer esters and polyesters, such as esters of diol dimer and of fatty acid, and esters of diol dimer and of diacid.

According to one particular embodiment, the oil phase may be free of non-volatile hydrocarbon-based oil(s). However, according to a preferred embodiment, if the oil phase includes the non-volatile hydrocarbon-based oil(s), it is preferable that the hydrocarbon oil be selected from fatty esters represented by the formula RCOOR' wherein R denotes a $C_{1-29}$ fatty acid residue, and R' denotes $C_{2-30}$ hydrocarbon group.

If the oil phase includes the non-volatile hydrocarbon-based oil(s), it is preferable that the amount of the non-volatile hydrocarbon-based oil(s) range from 10% to 40% by weight, preferably from 12% to 35% by weight, and more preferably from 15% to 30% by weight, relative to the total weight of the composition.

(Non-Volatile Silicone Oil)

The oil phase of a cosmetic composition according to the present invention advantageously comprise one or more non-volatile silicone oils.

The non-volatile silicone oil that may be used in the present invention may be chosen from silicone oils with a viscosity at 25° C. of greater than or equal to 8 centistokes (cSt) ($8 \times 10^{-6}$ m$^2$/s) and less than 800 000 cSt, preferably between 10 and 600 000 cSt and preferably between 100 and 500 000 cSt. The viscosity of this silicone may be measured according to standard ASTM D-445.

Among these silicone oils, two types of oil may be distinguished, according to whether or not they contain phenyl.

Representative examples of these non-volatile linear silicone oils that may be mentioned include polydimethylsiloxanes; alkyl dimethicones; vinyl methyl methicones; and also silicones modified with optionally fluorinated aliphatic groups, or with functional groups such as hydroxyl, thiol and/or amine groups.

Thus, non-phenyl non-volatile silicone oils that may be mentioned include:

PDMSs comprising alkyl or alkoxy groups, which are pendent and/or at the end of the silicone chain, these groups each containing from 2 to 24 carbon atoms, PDMSs comprising aliphatic groups, or functional groups such as hydroxyl, thiol and/or amine groups, polyalkylmethylsiloxanes optionally substituted with a fluorinated group, such as polymethyltrifluoropropyldimethylsiloxanes, polyalkylmethylsiloxanes substituted with functional groups such as hydroxyl, thiol and/or amine groups, polysiloxanes modified with fatty acids, fatty alcohols or polyoxyalkylenes, and mixtures thereof.

According to one particular embodiment, the oil phase contains at least one non-phenyl linear silicone oil.

The non-phenyl linear silicone oil may be chosen especially from the silicones of formula:

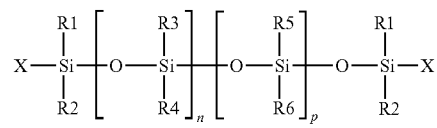

in which:

$R_1$, $R_2$, $R_5$ and $R_6$ are, together or separately, an alkyl radical containing 1 to 6 carbon atoms, $R_3$ and $R_4$ are, together or separately, an alkyl radical containing from 1 to 6 carbon atoms, a vinyl radical, an amine radical or a hydroxyl radical, X is an alkyl radical containing from 1 to 6 carbon atoms, a hydroxyl radical or an amine radical, n and p are integers chosen so as to have a fluid compound.

As non-volatile silicone oils that may be used according to the present invention, mention may be made of those for which:

- the substituents $R_1$ to $R_6$ and X represent a methyl group, and p and n are such that the viscosity is 500 000 cSt, such as the product sold under the name SE30 by the company General Electric, the product sold under the name AK 500000 by the company Wacker, the product sold under the name Mirasil DM 500 000 by the company Bluestar, and the product sold under the name Dow Corning 200 Fluid 500 000 cSt by the company Dow Corning,
- the substituents $R_1$ to $R_6$ and X represent a methyl group, and p and n are such that the viscosity is 60 000 cSt, such as the product sold under the name Dow Corning 200 Fluid 60000 CS by the company Dow Corning, and the product sold under the name Wacker Belsil DM 60 000 by the company Wacker,
- the substituents $R_1$ to $R_6$ and X represent a methyl group, and p and n are such that the viscosity is 350 cSt, such as the product sold under the name Dow Corning 200 Fluid 350 CS by the company Dow Corning,
- the substituents $R_1$ to $R_6$ represent a methyl group, the group X represents a hydroxyl group, and n and p are such that the viscosity is 700 cSt, such as the product sold under the name Baysilone Fluid T0.7 by the company Momentive.

According to one preferred embodiment variant, the oil phase contains at least one phenyl silicone oil.

Representative examples of these non-volatile phenyl silicone oils that may be mentioned include:

the phenyl silicone oils corresponding to the following formula;

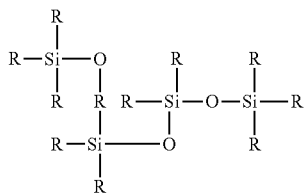
(I)

in which formula (I) the groups R represent, independently of each other, a methyl or a phenyl, with the proviso that at least one group R represents a phenyl. Preferably, in this formula, the phenyl silicone oil comprises at least three phenyl groups, for example at least four at least five or at least six, the phenyl silicone oils corresponding to the following formula;

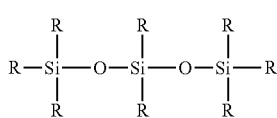
(II)

in which formula (II) the groups R represent, independently of each other, a methyl or a phenyl, with the proviso that at least one group R represents a phenyl. Preferably, in this formula, the said organopolysiloxane comprises at least three phenyl groups, for example at least four or at least five. Mixtures of the phenyl organopolysiloxanes described previously may be used. Examples that may be mentioned include mixtures of triphenyl, tetraphenyl or pentaphenyl organopolysiloxanes, the phenyl silicone oils corresponding to the following formula;

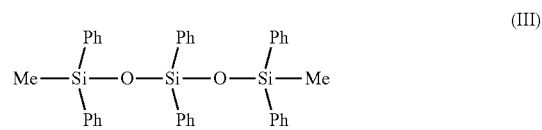
(III)

in which formula (III) Me represents methyl, Ph represents phenyl. Such a phenyl silicone is especially manufactured by Dow Corning under the reference PH-1555 HRI or Dow Corning 555 Cosmetic Fluid (chemical name: 1,3,5-trimethyl-1,1,3,5,5-pentaphenyl trisiloxane; INCI name: trimethyl pentaphenyl trisiloxane). The reference Dow Corning 554 Cosmetic Fluid may also be used, the phenyl silicone oils corresponding to the following formula;

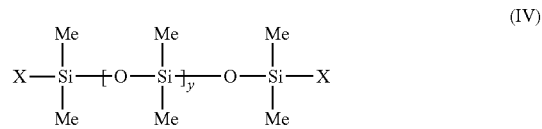
(IV)

in which formula (IV) Me represents methyl, y is between 1 and 1000 and X represents —CH—CH(CH$_3$)(Ph).

the phenyl silicone oils corresponding to formula (V) below;

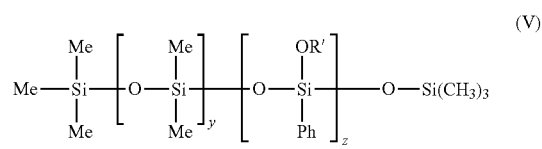
(V)

in which formula (V) Me is methyl and Ph is phenyl, OR' represents a group —OSiMe$_3$ and y is 0 or ranges between 1 and 1000, and z ranges between 1 and 1000, such that compound (V) is a non-volatile oil. According to a first embodiment, y ranges between 1 and 1000. Use may be made, for example, of trimethyl siloxyphenyl dimethicone, sold especially under the reference Belsil PDM 1000 sold by the company Wacker. According to a second embodiment, y is equal to 0. Use may be made, for example, of phenyl trimethylsiloxy trisiloxane, sold especially under the reference Dow Corning 556 Cosmetic Grade Fluid, the phenyl silicone oils corresponding to formula (VI) below, and mixtures thereof;

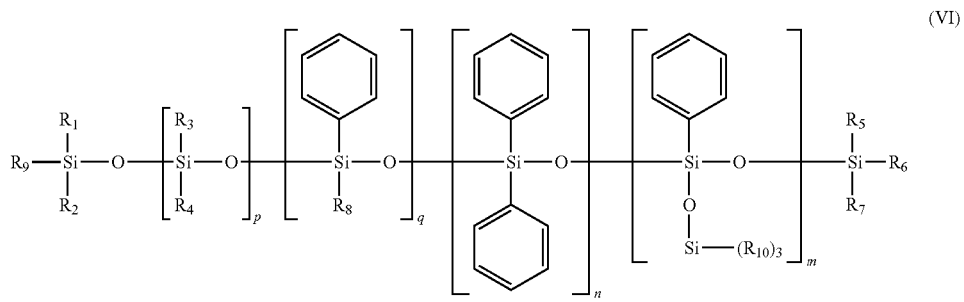

(VI)

in which formula (VI):

$R_1$ to $R_{10}$, independently of each other, are saturated or unsaturated, linear, cyclic or branched $C_1$-$C_{30}$ hydrocarbon-based radicals, m, n, p and q are, independently of each other, integers between 0 and 900, with the proviso that the sum m+n+q is other than 0; preferably, the sum m+n+q is between 1 and 100. Preferably, the sum m+n+p+q is between 1 and 900 and better still between 1 and 800. Preferably, q is equal to 0, the phenyl silicone oils corresponding to formula (VII) below, and mixtures thereof;

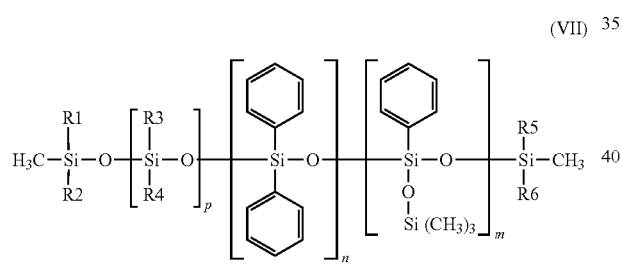

(VII)

in which formula (VII):

$R_1$ to $R_6$, independently of each other, are saturated or unsaturated, linear, cyclic or branched $C_1$-$C_{30}$ hydrocarbon-based radicals, m, n and p are, independently of each other, integers between 0 and 100, with the proviso that the sum n+m is between 1 and 100; preferably, $R_1$ to $R_6$, independently of each other, represent a saturated, linear or branched $C_1$-$C_{30}$ and especially $C_1$-$C_{12}$ hydrocarbon-based radical and in particular a methyl, ethyl, propyl or butyl radical; $R_1$ to $R_6$ may especially be identical, and in addition may be a methyl radical; Preferably, m=1 or 2 or 3, and/or n=0 and/or p=0 or 1 may apply, in formula (VI), the phenyl silicone oils corresponding to formula (VIII), and mixtures thereof:

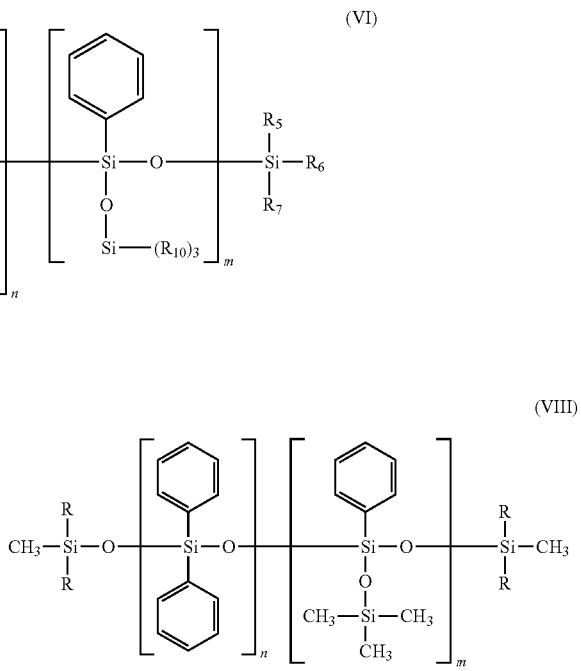

(VIII)

in which formula (VIII):

R is a $C_1$-$C_{30}$ alkyl radical, an aryl radical or an aralkyl radical, n is an integer ranging from 0 to 100, and m is an integer ranging from 0 to 100, with the proviso that the sum n+m ranges from 1 to 100. In particular, the radicals R of formula (VIII) and $R_1$ to $R_{10}$ defined previously may each represent a linear or branched, saturated or unsaturated alkyl radical, especially of $C_2$-$C_{20}$, in particular $C_3$-$C_{16}$ and more particularly $C_4$-$C_{10}$, or a monocyclic or polycyclic $C_6$-$C_{14}$ and especially $C_{10}$-$C_{13}$ aryl radical, or an aralkyl radical whose aryl and alkyl residues are as defined previously. Preferably, R of formula (VIII) and $R_1$ to $R_{10}$ may each represent a methyl, ethyl, propyl, isopropyl, decyl, dodecyl or octadecyl radical, or alternatively a phenyl, tolyl, benzyl or phenethyl radical. According to one embodiment, a phenyl silicone oil of formula (VIII) with a viscosity at 25° C. of between 5 and 1500 mm$^2$/s (i.e. 5 to 1500 cSt), and preferably with a viscosity of between 5 and 1000 mm$^2$/s (i.e. 5 to 1000 cSt) may be used. As phenyl silicone oils of formula (VIII), it is especially possible to use phenyl trimethicones such as DC556 from Dow Corning (22.5 cSt), the oil Silbione 70663V30 from Rhone-Poulenc (28 cSt) or diphenyl dimethicones such as Belsil oils, especially Belsil PDM1000 (1000 cSt), Belsil PDM 200 (200 cSt) and Belsil PDM 20 (20 cSt) from Wacker. The values in parentheses represent the viscosities at 25° C.

the phenyl silicone oils corresponding to the following formula, and mixtures thereof:

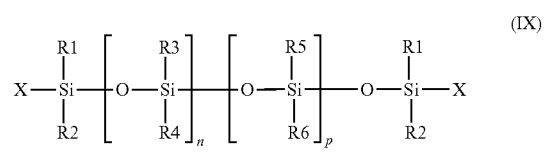

(IX)

in which formula (IX):
$R_1$, $R_2$, $R_5$ and $R_6$ are, together or separately, an alkyl radical containing 1 to 6 carbon atoms,
$R_3$ and $R_4$ are, together or separately, an alkyl radical containing from 1 to 6 carbon atoms or an aryl radical,
X is an alkyl radical containing from 1 to 6 carbon atoms, a hydroxyl radical or a vinyl radical,
n and p being chosen so as to give the oil a weight-average molecular mass of less than 200 000 g/mol, preferably less than 150 000 g/mol and more preferably less than 100 000 g/mol.

The phenyl silicones that are most particularly suitable for use in the present invention are those corresponding to formulae (II) and especially to formulae (III), (V) and (VIII) hereinabove.

More particularly, the phenyl silicones are chosen from phenyl trimethicones, phenyl dimethicones, phenyl-trimethylsiloxydiphenylsiloxanes, diphenyl dimethicones, diphenylmethyldiphenyltrisiloxanes and 2-phenylethyl trimethylsiloxysilicates, and mixtures thereof.

Preferably, the weight-average molecular weight of the non-volatile phenyl silicone oil used according to the present invention ranges from 500 to 10 000 g/mol.

According to one particular embodiment, the oil phase may be free of non-volatile silicone oil(s). However, the oil phase includes preferably a non-volatile silicone oil(s) selected from phenyl silicone oils, non-phenyl linear silicone oils and their mixture(s).

Preferably the oil phase includes preferably a non-volatile silicone oil(s) selected from phenyl silicone oils corresponding to formulae (II) and especially to formulae (III), (V) and (VIII), polydimethysiloxane oil(s), their mixture(s).

If the oil phase includes the non-volatile silicone oil(s), it is preferable that the amount of the silicone oil(s) range from 1% to 35% by weight, preferably from 2% to 30% by weight, and according to a particular embodiment from 4% to 12% by weight, relative to the total weight of the composition.

(Volatile Oil)

The oil phase may optionally comprise at least one volatile oil.

The term "volatile oil" means an oil (or non-aqueous medium) that can evaporate on contact with the skin in less than one hour, at room temperature and atmospheric pressure. The volatile oil is a cosmetic volatile oil, which is liquid at room temperature. More specifically, a volatile oil has an evaporation rate of between 0.01 and 200 mg/cm$^2$/min, limits included.

To measure this evaporation rate, 15 g of oil or of oil mixture to be tested are placed in a crystallizing dish 7 cm in diameter, which is placed on a balance in a large chamber of about 0.3 m$^3$ that is temperature-regulated, at a temperature of 25° C., and hygrometry-regulated, at a relative humidity of 50%. The liquid is allowed to evaporate freely, without stirring it, while providing ventilation by means of a fan (Papst-Motoren, reference 8550 N, rotating at 2700 rpm) placed in a vertical position above the crystallizing dish containing the said oil or the said mixture, the blades being directed towards the crystallizing dish, 20 cm away from the bottom of the crystallizing dish. The mass of oil remaining in the crystallizing dish is measured at regular intervals. The evaporation rates are expressed in mg of oil evaporated per unit of area (cm$^2$) and per unit of time (minutes).

This volatile oil may be a hydrocarbon-based oil, silicone oil or fluoro oil. It is preferably a hydrocarbon-based oil.

The term "hydrocarbon-based oil" means an oil mainly containing hydrogen and carbon atoms.

The term "silicone oil" means an oil containing at least one silicon atom, and especially containing Si—O groups. According to one embodiment, the said composition comprises less than 10% by weight of non-volatile silicone oil(s), relative to the total weight of the composition, better still less than 5% by weight, or even is free of silicone oil.

The term "fluoro oil" means an oil comprising at least one fluorine atom.

The oils may optionally comprise oxygen, nitrogen, sulfur and/or phosphorus atoms, for example in the form of hydroxyl or acid radicals.

The volatile oils may be chosen from hydrocarbon-based oils containing from 8 to 16 carbon atoms, and especially $C_8$-$C_{16}$ branched alkanes (also known as isoparaffins), for instance isododecane, isodecane and isohexadecane.

The volatile hydrocarbon-based oil may also be a linear volatile alkane containing 7 to 17 carbon atoms, in particular 9 to 15 carbon atoms and more particularly 11 to 13 carbon atoms. Mention may be made especially of n-nonadecane, n-decane, n-undecane, n-dodecane, n-tridecane, n-tetradecane, n-pentadecane and n-hexadecane, and mixtures thereof.

Preferably, the composition is free of volatile oil. Such an absence of volatile oil makes it possible, where appropriate, to dispense with a perfectly leak tight conditioning assembly for the said composition.

(Film-Forming Polymer)

The composition according to the present invention includes at least one hydrophobic film-forming polymer. Generally the oil phase and the hydrophobic film-forming polymer(s) form the liquid fatty phase of the composition.

For the purposes of the present invention, the term "polymer" means a compound corresponding to the repetition of one or more units (these units being derived from compounds known as monomers). This or these units(s) are repeated at least twice and preferably at least three times.

For the purposes of the present invention, the term "hydrophobic film-forming polymer" is intended to denote a film-forming polymer that has no affinity for water and, in this respect, does not lend itself to formulation in the form of a solute in an aqueous medium. In particular, the term "hydrophobic polymer" means a polymer with a solubility in water at 25° C. of less than 1% by weight.

The term "film-forming polymer" means a polymer that is capable of forming, by itself or in the presence of an auxiliary film-forming agent, a macroscopically continuous film that adheres to a support, especially to keratin materials, preferably a cohesive film, and better still a film whose cohesion and mechanical properties are such that the said film may be isolable and manipulable in isolation, for example when the said film is prepared by pouring onto a non-stick surface, for instance a Teflon-coated or silicone-coated surface.

In one preferred embodiment, the hydrophobic film-forming polymer is a polymer chosen from the group comprising:
film-forming polymers that are soluble in an organic solvent medium, in particular liposoluble polymers; this means that the polymer is soluble or miscible in the organic medium and will form a single homogeneous phase when it is incorporated into the medium;
film-forming polymers that are dispersible in an organic solvent medium; this means that the polymer forms an insoluble phase in the organic medium, the polymer remaining stable and/or compatible once incorporated into this medium. In particular, such polymers may be in the form of non-aqueous dispersions of polymer particles, preferably dispersions in silicone-based or hydrocarbon-based oils; in one embodiment, the non-aqueous dispersions of polymer comprise polymer particles stabilized on their surface with at least one stabilizer, these non-aqueous dispersions are often referred to as "NADs"; and film-forming polymers in the form of aqueous dispersions of polymer particles; this means that the polymer forms an insoluble phase in water, the polymer remaining stable and/or compatible once incorporated into the water, the polymer particles possibly being stabilized at their surface with at least one stabilizer. These polymer particles are often referred to as "latices"; in this case, the composition must comprise an aqueous phase.

It is preferable that the hydrophobic film-forming polymer be present in an amount of 0.1% by weight or more, preferably from 0.1% to 10% by weight, and more preferably from 0.5% to 8% by weight, still more preferably from 1% to 6% by weight relative to the total weight of the composition.

It is preferable that the amount of the oil phase and the amount of the hydrophobic film-forming polymer(s) are such that the weight ratio of the oil phase: the hydrophobic film-forming polymer(s) is ranging from 98:2 to 70:30, preferably 95:5 to 80:20, and more preferably 91:9 to 75:25.

It is preferable that the hydrophobic film-forming polymer be selected from polyamide-silicone block polymers, block ethylenic polymers, vinyl polymers comprising at least one carbosiloxane dendrimer derivative, copolymers comprising carboxylate groups and polydimethylsiloxane groups, silicone resins, lipodispersible polymer in the form of a non-aqueous dispersion of polymer particles, olefin copolymers selected from amorphous olefin copolymers and olefin copolymers with controlled and moderate crystallization, hydrocarbon-based resins having a number-average molecular weight of less than or equal to 10000 g/mol, and a mixture thereof.

(1) Polyamide-Silicone Block Polymer

According to one embodiment, a cosmetic composition according to the present invention comprises, as a hydrophobic film-forming polymer, at least one polyamide silicone block polymer, also known as a silicone polyamide.

The silicone polyamides are preferably solid at room temperature (25° C.) and atmospheric pressure (760 mmHg).

The silicone polyamides of the composition of the present invention may be polymers of the polyorganosiloxane type, for instance those described in documents U.S. Pat. Nos. 5,874,069, 5,919,441, 6,051,216 and 5,981,680. According to the present invention, the silicone polymers may belong to the following two families:

(a) polyorganosiloxanes comprising at least two amide groups, these two groups being located in the polymer chain, and/or
(b) polyorganosiloxanes comprising at least two amide groups, these two groups being located on grafts or branches.

According to a first variant, the silicone polymers are polyorganosiloxanes as defined above in which the units capable of establishing hydrogen interactions are located in the polymer chain.

The silicone polymers may more particularly be polymers comprising at least one unit corresponding to the general formula I:

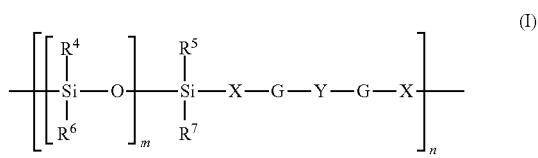

in which:
R4, R5, R6 and R7, which may be identical or different, represent a group chosen from
  linear, branched or cyclic, saturated or unsaturated, $C_1$ to $C_{40}$ hydrocarbon-based groups, possibly containing in their chain one or more oxygen, sulfur and/or nitrogen atoms, and possibly being partially or totally substituted with fluorine atoms,
  $C_6$-$C_{10}$ aryl groups, optionally substituted with one or more $C_1$-$C_4$ alkyl groups,
  polyorganosiloxane chains possibly containing one or more oxygen, sulfur and/or nitrogen atoms,
the groups X, which may be identical or different, represent a linear or branched $C_1$ to $C_{30}$ alkylenediyl group, possibly containing in its chain one or more oxygen and/or nitrogen atoms;
Y is a saturated or unsaturated $C_1$ to $C_{50}$ linear or branched alkylene, arylene, cycloalkylene, alkylarylene or arylalkylene divalent group, which may comprise one or more oxygen, sulfur and/or nitrogen atoms and/or which may bear as substituent one of the following atoms or groups of atoms: fluorine, hydroxyl, $C_3$ to $C_8$ cycloalkyl, $C_1$ to $C_{40}$ alkyl, $C_5$ to $C_{10}$ aryl, phenyl optionally substituted with 1 to 3 $C_1$ to $C_3$ alkyl, $C_1$ to $C_3$ hydroxyalkyl and $C_1$ to $C_6$ aminoalkyl groups, or
Y represents a group corresponding to the formula:

in which:
T represents a linear or branched, saturated or unsaturated, $C_3$ to $C_{24}$ trivalent or tetravalent hydrocarbon-based group optionally substituted with a polyorganosiloxane chain, and possibly containing one or more atoms chosen from O, N and S, or T represents a trivalent atom chosen from N, P and Al, and
R8 represents a linear or branched $C_1$ to $C_{50}$ alkyl group or a polyorganosiloxane chain, possibly comprising one or more ester, amide, urethane, thiocarbamate, urea, thiourea and/or sulfonamide groups, which may possibly be linked to another chain of the polymer;
the groups G, which may be identical or different, represent divalent groups chosen from:

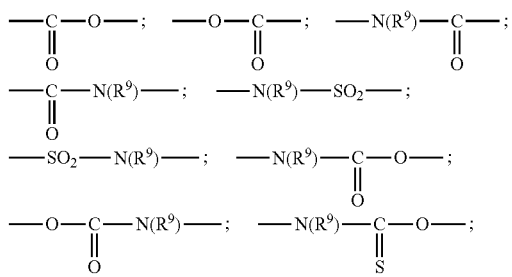

-continued $$—O—C(=S)—N(R^9)—; \quad —N(R^9)—C(=O)—N(R^9)—,$$

$$—N(R^9)—C(=S)—N(R^9)—,$$

$$—N(R^9)—C(=O)—C(=O)—N(R^9); \quad —NH—C(=NH)—NH—; \text{ et}$$

$$—NH—C(=NH)—NH—C(=NH)—NH—;$$

in which R9 represents a hydrogen atom or a linear or branched $C_1$ to $C_{20}$ alkyl group, on condition that at least 50% of the groups R9 of the polymer represent a hydrogen atom and that at least two of the groups G of the polymer are a group other than $$—O—C(=O)— \text{ and } —C(=O)—O—$$

and
n is an integer ranging from 2 to 500 and preferably from 2 to 200, and m is an integer ranging from 1 to 1000, preferably from 1 to 700 and better still from 6 to 200.

According to the present invention, 80% of the groups R4, R5, R6 and R7 of the polymer are preferably chosen from methyl, ethyl, phenyl and 3,3,3-trifluoropropyl groups.

According to the present invention, Y can represent various divalent groups, furthermore optionally comprising one or two free valencies to establish bonds with other units of the polymer or copolymer. Preferably, Y represents a group chosen from:

$C_1$ to $C_{20}$ and preferably $C_1$ to $C_{10}$ linear alkylene groups,
$C_{30}$ to $C_{56}$ branched alkylene groups possibly comprising rings and unconjugated unsaturations,
$C_5$ to $C_6$ cycloalkylene groups,
phenylene groups optionally substituted with one or more $C_1$ to $C_{40}$ alkyl groups,
$C_1$ to $C_{20}$ alkylene groups comprising from 1 to 5 amide groups,
$C_1$ to $C_{20}$ alkylene groups comprising one or more substituents chosen from hydroxyl, $C_3$ to $C_8$ cycloalkane, $C_1$ to $C_3$ hydroxyalkyl and $C_1$ to $C_6$ alkylamine groups,
polyorganosiloxane chains of formula:

$$R^4—\underset{R^7}{\overset{R^5}{Si}}—O—\left[\underset{R^6}{\overset{R^4}{Si}}—O\right]_m—\underset{R^7}{\overset{R^5}{Si}}—T\diagdown$$

in which R4, R5, R6, R7, T and m are as defined above, and
polyorganosiloxane chains of formula:

$$—\underset{R^7}{\overset{R^5}{Si}}—O—\left[\underset{R^6}{\overset{R^4}{Si}}—O\right]_m—\underset{R^7}{\overset{R^5}{Si}}—T\diagdown.$$

According to the second variant, the polyorganosiloxanes may be polymers comprising at least one unit corresponding to formula (II):

$$—\left[\underset{R^6}{\overset{R^4}{Si}}—O\right]_{m_1}\left[\underset{R^{10}}{\overset{R^{11}}{Si}}—O\right]_{m_2}— \quad (II)$$

in which:
R4 and R6, which may be identical or different, are as defined above for formula (I),
R10 represents a group as defined above for R4 and R6, or represents a group of formula —X-G-R12 in which X and G are as defined above for formula (I) and R12 represents a hydrogen atom or a linear branched or cyclic, saturated or unsaturated, $C_1$ to $C_{50}$ hydrocarbon-based group optionally comprising in its chain one or more atoms chosen from O, S and N, optionally substituted with one or more fluorine atoms and/or one or more hydroxyl groups, or a phenyl group optionally substituted with one or more $C_1$ to $C_4$ alkyl groups,
R11 represents the group of formula —X-G-R12 in which X, G and R12 are as defined above,
m1 is an integer ranging from 1 to 998, and
m2 is an integer ranging from 2 to 500.

According to the present invention, the silicone polymer used as structuring agent may be a homopolymer, i.e. a polymer comprising several identical units, in particular units of formula (I) or of formula (II).

According to the present invention, it is also possible to use a silicone polymer formed from a copolymer comprising several different units of formula (I), i.e. a polymer in which at least one of the groups R4, R5, R6, R7, X, G, Y, m and n is different in one of the units. The copolymer may also be formed from several units of formula (II), in which at least one of the groups R4, R6, R10, R11, m1 and m2 is different in at least one of the units.

It is also possible to use a polymer comprising at least one unit of formula (I) and at least one unit of formula (II), the units of formula (I) and the units of formula (II) possibly being identical to or different from each other.

According to one variant, it is also possible to use a polymer furthermore comprising at least one hydrocarbon-based unit comprising two groups capable of establishing hydrogen interactions, chosen from ester, amide, sulfonamide, carbamate, thiocarbamate, urea, urethane, thiourea, oxamido, guanidino and biguanidino groups, and combinations thereof.

These copolymers may be block polymers or grafted polymers.

According to one advantageous embodiment of the present invention, the groups capable of establishing hydrogen interactions are amide groups of formulae —C(O)NH— and —HN—C(O)—. In this case, the structuring agent may be a polymer comprising at least one unit of formula (III) or (IV):

$$—\left[\underset{O}{\overset{}{C}}—X—\left[\underset{R^6}{\overset{R^4}{SiO}}\right]_m\underset{R^7}{\overset{R^5}{Si}}—X—\underset{O}{\overset{}{C}}—NH—Y—NH\right]_n— \quad (III)$$

(IV)

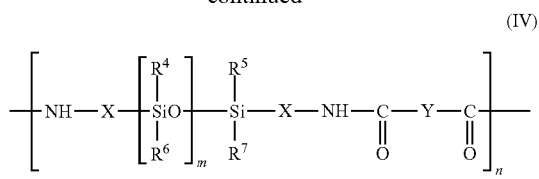

in which R4, R5, R6, R7, X, Y, m and n are as defined above.

Such a unit may be obtained:

either by a condensation reaction between a silicone containing α, ω-carboxylic acid end units and one or more diamines, according to the following reaction scheme:

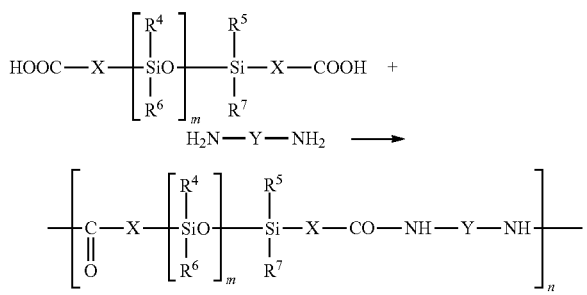

or by reaction of two unsaturated αcarboxylic acid molecules with a diamine according to the following reaction scheme:

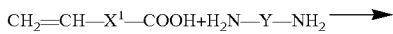

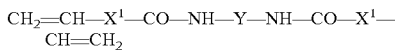

followed by the addition of a siloxane to the ethylenic unsaturations, according to the following scheme:

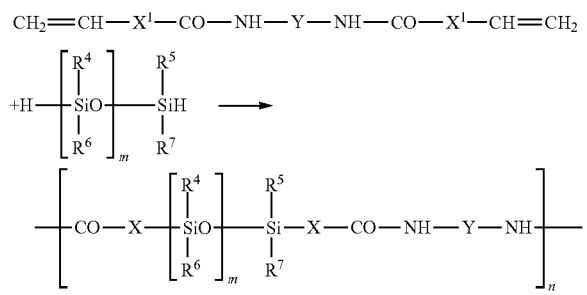

in which X1-$(CH_2)_2$— corresponds to X defined above and Y, R4, R5, R6, R7 and m are as defined above, or by reaction of a silicone containing α, ω-$NH_2$ end groups and of a diacid of formula HOOC—Y—COOH according to the following reaction scheme:

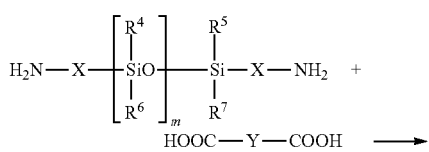

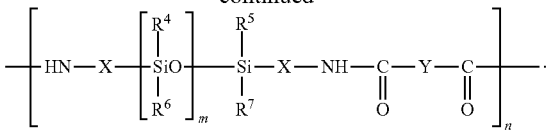

In these polyamides of formula (III) or (IV), m ranges from 1 to 700, in particular from 15 to 500 and especially from 50 to 200, and n ranges in particular from 1 to 500, preferably from 1 to 100 and better still from 4 to 25, X is preferably a linear or branched alkylene chain containing from 1 to 30 carbon atoms, in particular 1 to 20 carbon atoms, especially from 5 to 15 carbon atoms and more particularly 10 carbon atoms, and Y is preferably an alkylene chain that is linear or branched, or which may comprise rings and/or unsaturations, containing from 1 to 40 carbon atoms, in particular 1 to 20 carbon atoms and better still from 2 to 6 carbon atoms, in particular 6 carbon atoms.

In formulae (III) and (IV), the alkylene group representing X or Y can optionally contain in its alkylene part at least one of the following components:

one to five amide, urea, urethane or carbamate groups, a $C_5$ or $C_6$ cycloalkyl group, and a phenylene group optionally substituted with 1 to 3 identical or different $C_1$ to $C_3$ alkyl groups.

In formulae (III) and (IV), the alkylene groups may also be substituted with at least one component chosen from the group consisting of:

a hydroxyl group, a $C_3$ to $C_8$ cycloalkyl group, one to three $C_1$ to $C_{40}$ alkyl groups, a phenyl group optionally substituted with one to three $C_1$ to $C_3$ alkyl groups, a $C_1$ to $C_3$ hydroxyalkyl group, and a $C_1$ to $C_6$ aminoalkyl group.

In these formulae (III) and (IV), Y may also represent:

in which R8 represents a polyorganosiloxane chain and T represents a group of formula:

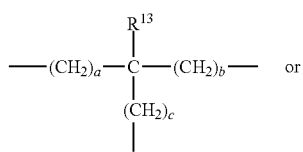

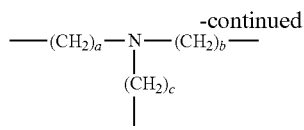

in which a, b and c are, independently, integer ranging from 1 to 10, and R13 is a hydrogen atom or a group such as those defined for R4, R5, R6 and R7.

In formulae (III) and (IV), R4, R5, R6 and R7 preferably represent, independently, a linear or branched $C_1$ to $C_{40}$ alkyl group, preferably a $CH_3$, $C_2H_5$, n-$C_3H_7$ or isopropyl group, a polyorganosiloxane chain or a phenyl group optionally substituted with one to three methyl or ethyl groups.

As has been seen previously, the polymer may comprise identical or different units of formula (III) or (IV).

Thus, the polymer may be a polyamide containing several units of formula (III) or (IV) of different lengths, i.e. a polyamide corresponding to formula (V):

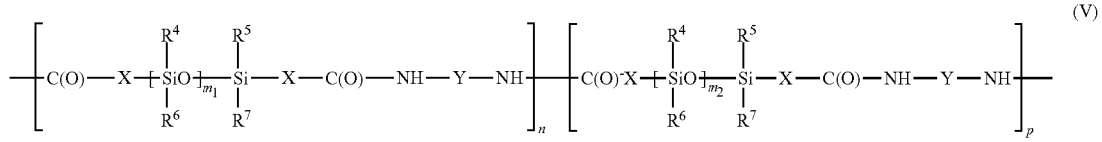

which X, Y, n and R4 to R7 have the meanings given above, m1 and m2, which are different, are chosen in the range from 1 to 1000, and p is an integer ranging from 2 to 300.

In this formula, the units may be structured to form either a block copolymer, or a random copolymer or an alternating copolymer. In this copolymer, the units may be not only of different lengths, but also of different chemical structures, for example containing different groups Y. In this case, the polymer may correspond to formula VI:

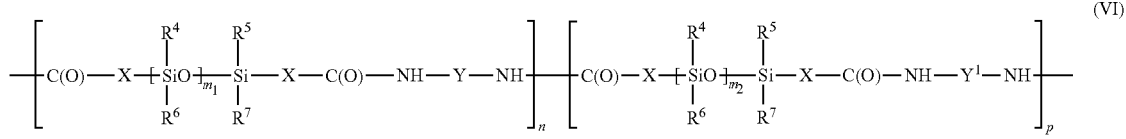

which R4 to R7, X, Y, m1, m2, n and p have the meanings given above and Y1 is different from Y but chosen from the groups defined for Y. As previously, the various units may be structured to form either a block copolymer, or a random copolymer or an alternating copolymer.

In this first embodiment of the present invention, the structuring agent may also be formed from a grafted copolymer. Thus, the polyamide containing silicone units may be grafted and optionally crosslinked with silicone chains containing amide groups. Such polymers may be synthesized with trifunctional amines.

In this case, the polymer may comprise at least one unit of formula (VII):

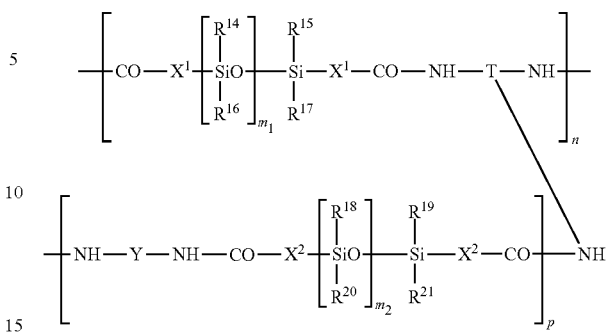

in which X1 and X2, which are identical or different, have the meaning given for X in formula (I), n is as defined in formula (I), Y and T are as defined in formula (I), R14 to R21 are groups chosen from the same group as R4 to R7, m1 and m2 are numbers located in the range from 1 to 1000, and p is an integer ranging from 2 to 500.

In formula (VII), the following are preferred:
p ranges from 1 to 25 and better still from 1 to 7,
R14 to R21 are methyl groups,
T corresponds to one of the following formulae:

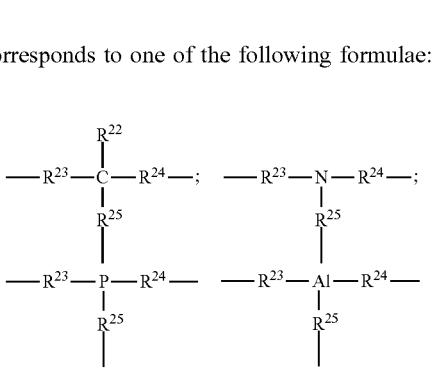

in which R22 is a hydrogen atom or a group chosen from the groups defined for R4 to R7, and R23, R24 and R25 are, independently, linear or branched alkylene groups, more preferably corresponding to the formula:

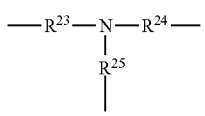

in particular with R23, R24 and R25 representing —CH$_2$—CH$_2$—, m1 and m2 range from 15 to 500 and better still from 15 to 45, X1 and X2 represent —(CH$_2$)$_{10}$—, and Y represents —CH$_2$—.

These polyamides containing a grafted silicone unit of formula (VII) may be copolymerized with polyamide silicones of formula (II) to form block copolymers, alternating copolymers or random copolymers. The weight percentage of grafted silicone units (VII) in the copolymer may range from 0.5% to 30% by weight.

According to the present invention, as has been seen previously, the siloxane units may be in the main chain or backbone of the polymer, but they may also be present in grafted or pendent chains. In the main chain, the siloxane units may be in the form of segments as described above. In the pendent or grafted chains, the siloxane units may appear individually or in segments.

According to one embodiment variant of the present invention, a copolymer of silicone polyamide and of hydrocarbon-based polyamide, or a copolymer comprising units of formula (III) or (IV) and hydrocarbon-based polyamide units, may be used. In this case, the silicone polyamide units may be located at the ends of the hydrocarbon-based polyamide.

According to one preferred embodiment, the silicone polyamide comprises units of formula III, preferably in which the groups R4, R5, R6 and R7 represent methyl groups, one from among X and Y represents an alkylene group of 6 carbon atoms and the other represents an alkylene group of 11 carbon atoms, n representing the degree of polymerization, DP, of the polymer. By way of example of such silicone polyamides, mention may be made of the compounds sold by the company Dow Corning under the names DC 2-8179 (DP 100) and DC 2-8178 (DP 15), the INCI name of which is Nylon-611/dimethicone copolymer.

Advantageously, the cosmetic composition according to the present invention comprises at least one polydimethylsiloxane block polymer of general formula (I) with an index m of about 15.

More preferably, the cosmetic composition according to the present invention comprises at least one polymer comprising at least one unit of formula (III) in which m ranges from 5 to 100, in particular from 10 to 75 and even more particularly is about 15; even more preferably, R4, R5, R6 and R7 independently represent a linear or branched C$_1$ to C$_{40}$ alkyl group, preferably a group CH$_3$, C$_2$H$_5$, n-C$_3$H$_7$ or isopropyl in formula (III).

According to one preferred mode, the silicone polyamide sold by the company Dow Corning under the name DC 2-8179 (DP 100) is used.

As examples of silicone polymers that may be used, mention may be made of one of the silicone polyamides obtained in accordance with Examples 1 to 3 of document U.S. Pat. No. 5,981,680.

Preferably, the polyamide-silicone block (co)polymer may be present in the composition in an active material content ranging from 0.1% to 20%, better still from 0.5% to 15%, better still from 1% to 12% and even better still from 1.5% to 10% by weight relative to the total weight of the composition.

(2) Block Ethylenic Polymer

According to one embodiment of the present invention, the hydrophobic film-forming polymer may be a block ethylenic copolymer, which may contain at least a first block with a glass transition temperature (Tg) of greater than or equal to 40° C. and being totally or partly derived from one or more first monomers, which are such that the homopolymer prepared from these monomers has a glass transition temperature of greater than or equal to 40° C., and at least a second block with a glass transition temperature of less than or equal to 20° C. and being derived totally or partly from one or more second monomers, which are such that the homopolymer prepared from these monomers has a glass transition temperature of less than or equal to 20° C., the said first block and the said second block being connected together via a statistical intermediate segment comprising at least one of the said first constituent monomers of the first block and at least one of the said second constituent monomers of the second block, and the said block copolymer having a polydispersity index I of greater than 2.

The block polymer used according to the present invention thus comprises at least one first block and at least one second block.

The term "at least one block" means one or more blocks.

The term "block" polymer means a polymer comprising at least two different blocks and preferably at least three different blocks.

The term "ethylenic" polymer means a polymer obtained by polymerization of ethylenically unsaturated monomers.

The block ethylenic polymer used according to the present invention is prepared exclusively from monofunctional monomers.

This means that the block ethylenic polymer used according to the present invention does not contain any multifunctional monomers, which make it possible to break the linearity of a polymer so as to obtain a branched or even crosslinked polymer, as a function of the content of multifunctional monomer. The polymer used according to the present invention does not, either, contain any macromonomers (the term "macromonomer" means a monofunctional monomer containing pendent groups of polymeric nature, and preferably having a molecular mass of greater than 500 g/mol, or alternatively a polymer comprising on only one of its ends a polymerizable (or ethylenically unsaturated) end group), which are used in the preparation of a grafted polymer.

It is pointed out that, in the text hereinabove and hereinbelow, the terms "first" and "second" blocks do not in any way condition the order of the said blocks in the structure of the block polymer.

The first block and the second block of the polymer used in the present invention may be advantageously mutually incompatible.

The term "mutually incompatible blocks" means that the mixture formed from the polymer corresponding to the first block and form the polymer corresponding to the second block is not miscible in the polymerization solvent that is in major amount by weight for the block polymer, at room temperature (25° C.) and atmospheric pressure (10$^5$ Pa), for a content of the mixture of the said polymers of greater than or equal to 5% by weight, relative to the total weight of the mixture of the said polymers and of the said polymerization solvent, it being understood that:

i) the said polymers are present in the mixture in a content such that the respective weight ratio ranges from 10/90 to 90/10, and that ii) each of the polymers corresponding to the first and second blocks has an average (weight-average or number-average) molecular mass equal to that of the block polymer ±15%.

In the case of a mixture of polymerization solvents, and in the event that two or more solvents are present in identical mass proportions, the said polymer mixture is immiscible in at least one of them.

Needless to say, in the case of a polymerization performed in a single solvent, this solvent is the solvent that is in major amount.

The block polymer used according to the present invention may comprise at least a first block and at least a second block that are connected together via an intermediate segment comprising at least one constituent monomer of the first block and at least one constituent monomer of the second block. The intermediate segment (also known as the intermediate block) has a glass transition temperature Tg that is between the glass transition temperatures of the first and second blocks.

The intermediate segment is a block comprising at least one constituent monomer of the first block and at least one constituent monomer of the second block of the polymer allowing these blocks to be "compatibilized".

Advantageously, the intermediate segment comprising at least one constituent monomer of the first block and at least one constituent monomer of the second block of the block polymer is a statistical polymer.

Preferably, the intermediate block is derived essentially from constituent monomers of the first block and of the second block.

The term "essentially" means at least 85%, preferably at least 90%, better still 95% and even better still 100%.

The block polymer used according to the present invention is advantageously a film-forming block ethylenic polymer.

The term "ethylenic" polymer means a polymer obtained by polymerization of ethylenically unsaturated monomers.

Preferentially, the polymer used according to the present invention does not comprise any silicon atoms in its backbone. The term "backbone" means the main chain of the polymer, as opposed to the pendent side chains.

Preferably, the polymer used according to the present invention is not water-soluble, i.e. the polymer is not soluble in water or in a mixture of water and linear or branched lower monoalcohols containing from 2 to 5 carbon atoms, for instance ethanol, isopropanol or n-propanol, without modifying the pH, at the solids content of at least 1% by weight, at room temperature (25° C.).

Preferably, the polymer used according to the present invention is not an elastomer.

The term "non-elastomeric polymer" means a polymer which, when it is subjected to a constraint intended to stretch it (for example by 30% relative to its initial length), it does not return to a length substantially identical to its initial length when the constraint ceases.

More specifically, the term "non-elastomeric polymer" denotes a polymer with an instantaneous recovery $R_i$<50% and a delayed recovery $R_{2h}$<70% after having been subjected to a 30% elongation. Preferably, $R_i$ is <30% and $R_{2h}$<50%.

More specifically, the non-elastomeric nature of the polymer is determined according to the following protocol.

A polymer film is prepared by pouring a solution of the polymer in a Teflon-coated mould, followed by drying for 7 days in an environment conditioned at 23±5° C. and 50±10% relative humidity.

A film about 100 μm thick is thus obtained, from which are cut rectangular specimens (for example using a punch) 15 mm wide and 80 mm long.

This sample is subjected to a tensile stress using a machine sold under the reference Zwick, under the same temperature and humidity conditions as for the drying.

The specimens are pulled at a speed of 50 mm/min and the distance between the jaws is 50 mm, which corresponds to the initial length ($I_0$) of the specimen.

The instantaneous recovery Ri is determined in the following manner:
the specimen is pulled by 30% ($\varepsilon_{max}$), i.e. about 0.3 times its initial length ($I_0$)
the constraint is released by applying a return speed equal to the tensile speed, i.e. 50 mm/min, and the residual elongation of the specimen is measured as a percentage, after returning to zero constraint ($\varepsilon_i$).

The percentage instantaneous recovery ($R_i$) is given by the following formula:

$$R_i=(\varepsilon_{max}-\varepsilon_i)/\varepsilon_{max}\times100$$

To determine the delayed recovery, the percentage residual elongation of the specimen ($\varepsilon_{2h}$) is measured 2 hours after returning to zero constraint.

The percentage delayed recovery ($R_{2h}$) is given by the following formula:

$$R_{2h}=(\varepsilon_{max}-\varepsilon_{2h})/\varepsilon_{max}\times100$$

Purely as a guide, a polymer according to one embodiment of the present invention preferably has an instantaneous recovery $R_i$ of 10% and a delayed recovery $R_{2h}$ of 30%.

The polydispersity index of the polymer of the present invention is greater than 2.

Advantageously, the block polymer used in the cosmetic compositions according to the present invention has a polydispersity index I of greater than 2, for example ranging from 2 to 9, preferably greater than or equal to 2.5, for example ranging from 2.5 to 8 and better still greater than or equal to 2.8, and especially ranging from 2.8 to 6.

The polydispersity index I of the polymer is equal to the ratio of the weight-average molecular mass Mw to the number-average molecular mass Mn.

The weight-average molar mass (Mw) and number-average molar mass (Mn) are determined by gel permeation liquid chromatography (THF solvent, calibration curve established with linear polystyrene standards, refractometric detector).

The weight-average mass (Mw) of the polymer used according to the present invention is preferably less than or equal to 300 000; it ranges, for example, from 35 000 to 200 000 and better still from 45 000 to 150 000 g/mol.

The number-average mass (Mn) of the polymer used according to the present invention is preferably less than or equal to 70 000; it ranges, for example, from 10 000 to 60 000 and better still from 12 000 to 50 000 g/mol.

Preferably, the polydispersity index of the polymer used according to the present invention is greater than 2, for example ranging from 2 to 9, preferably greater than or equal to 25, for example ranging from 25 to 8 and better still greater than or equal to 2.8, and especially ranging from 2.8 to 6.

First Block with a Tg of Greater than or Equal to 40° C.

The block with a Tg of greater than or equal to 40° C. has, for example, a Tg ranging from 40 to 150° C., preferably greater than or equal to 50° C., for example ranging from 50° C. to 120° C. and better still greater than or equal to 60° C., for example ranging from 60° C. to 120° C.

The glass transition temperatures indicated for the first and second blocks may be theoretical Tg values determined from the theoretical Tg values of the constituent monomers of each of the blocks, which may be found in a reference manual such as the Polymer Handbook, 3rd Edition, 1989, John Wiley, according to the following relationship, known as Fox's law:

$$1/Tg = \Sigma(\overline{\omega}_i/Tg_i), i$$

$\overline{\omega}_i$ being the mass fraction of the monomer i in the block under consideration and $Tg_i$ being the glass transition temperature of the homopolymer of the monomer i.

Unless otherwise indicated, the Tg values indicated for the first and second blocks in the present patent application are theoretical Tg values.

The difference between the glass transition temperatures of the first and second blocks is generally greater than 10° C., preferably greater than 20° C. and better still greater than 30° C.

In the present invention, the expression: "between . . . and . . . " is intended to denote a range of values for which the limits mentioned are excluded, and "from . . . to . . . " and "ranging from . . . to . . . " are intended to denote a range of values for which the limits are included.

The block with a Tg of greater than or equal to 40° C. may be a homopolymer or a copolymer.

The block with a Tg of greater than or equal to 40° C. may be derived totally or partially from one or more monomers which are such that the homopolymer prepared from these monomers has a glass transition temperature of greater than or equal to 40° C. This block may also be referred to as a "rigid block".

In the case where this block is a homopolymer, it is derived from monomers which are such that the homopolymers prepared from these monomers have glass transition temperatures of greater than or equal to 40° C. This first block may be a homopolymer consisting of only one type of monomer (for which the Tg of the corresponding homopolymer is greater than or equal to 40° C.).

In the case where the first block is a copolymer, it may be totally or partially derived from one or more monomers, the nature and concentration of which are chosen such that the Tg of the resulting copolymer is greater than or equal to 40° C.

The copolymer may comprise, for example:
monomers which are such that the homopolymers prepared from these monomers have Tg values of greater than or equal to 40° C., for example a Tg ranging from 40 to 150° C., preferably greater than or equal to 50° C., for example ranging from 50° C. to 120° C. and better still greater than or equal to 60° C., for example ranging from 60° C. to 120° C., and
monomers which are such that the homopolymers prepared from these monomers have Tg values of less than 40° C., chosen from monomers with a Tg of between 20° C. and 40° C. and/or monomers with a Tg of less than or equal to 20° C., for example a Tg ranging from −100° C. to 20° C., preferably less than 15° C., especially ranging from −80° C. to 15° C. and better still less than 10° C., for example ranging from −50° C. to 0° C., as described later.

The first monomers whose homopolymers have a glass transition temperature of greater than or equal to 40° C. are chosen, preferably, from the following monomers, also known as the main monomers:
the methacrylates of formula $CH_2=C(CH_3)-COOR_1$
in which $R_1$ represents a linear or branched unsubstituted alkyl group containing from 1 to 4 carbon atoms, such as a methyl, ethyl, propyl or isobutyl group or $R_1$ represents a $C_4$ to $C_{12}$ cycloalkyl group, preferably a $C_8$ to $C_{12}$ cycloalkyl, such as isobornyl methacrylate,
the acrylates of formula $CH_2=CH-COOR_2$
in which $R_2$ represents a $C_4$ to $C_{12}$ cycloalkyl group such as an isobornyl group or a tert-butyl group,
the (meth)acrylamides of formula:

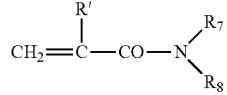

in which $R_7$ and $R_8$, which may be identical or different, each represent a hydrogen atom or a linear or branched $C_1$ to $C_{12}$ alkyl group such as an n-butyl, t-butyl, isopropyl, isohexyl, isooctyl or isononyl group; or $R_7$ represents H and $R_8$ represents a 1,1-dimethyl-3-oxobutyl group, and
R' denotes H or methyl. Examples of monomers that may be mentioned include N-butylacrylamide, N-tert-butylacrylamide, N-isopropylacrylamide, N,N-dimethylacylamide and N,N-dibutylacrylamide, and mixtures thereof.

The first block is advantageously obtained from at least one acrylate monomer of formula $CH_2=CH-COOR_2$ and from at least one methacrylate monomer of formula $CH_2=C(CH_3)-COOR_2$ in which $R_2$ represents a $C_4$ to $C_{12}$ cycloalkyl group, preferably a $C_8$ to $C_{12}$ cycloalkyl, such as isobornyl. The monomers and the proportions thereof are preferably chosen such that the glass transition temperature of the first block is greater than or equal to 40° C.

According to one embodiment, the first block is obtained from:
i) at least one acrylate monomer of formula $CH_2=CH-COOR_2$ in which $R_2$ represents a $C_4$ to $C_{12}$ cycloalkyl group, preferably a $C_8$ to $C_{12}$ cycloalkyl, such as isobornyl, and
ii) at least one methacrylate monomer of formula $CH_2=C(CH_3)-COOR'_2$ in which $R'_2$ represents a $C_4$ to $C_{12}$ cycloalkyl group, preferably a $C_8$ to $C_{12}$ cycloalkyl, such as isobornyl.

According to one embodiment, the first block is obtained from at least one acrylate monomer of formula $CH_2=CH-COOR_2$ in which $R_2$ represents a $C_8$ to $C_{12}$ cycloalkyl group, such as isobornyl, and from at least one methacrylate monomer of formula $CH_2=C(CH_3)-COOR'_2$ in which $R_2$ represents a $C_8$ to $C_{12}$ cycloalkyl group, such as isobornyl.

Preferably, $R_2$ and $R'_2$ represents, independently or simultaneously, an isobornyl group.

Preferably, the block copolymer comprises from 50% to 80% by weight of isobornyl methacrylate/acrylate, from 10% to 30% by weight of isobutyl acrylate and from 2% to 10% by weight of acrylic acid.

The first block may be obtained exclusively from the said acrylate monomer and from the said methacrylate monomer.

The acrylate monomer and the methacrylate monomer are preferably in mass proportions of between 30/70 and 70/30, preferably between 40/60 and 60/40, especially about 50/50.

The proportion of the first block advantageously ranges from 20% to 90%, better still from 30% to 80% and even better still from 60% to 80% by weight of the polymer.

According to one embodiment, the first block is obtained by polymerization of isobornyl methacrylate and isobornyl acrylate.

Second Block with a Glass Transition Temperature of Less than 20° C.

The second block advantageously has a glass transition temperature Tg of less than or equal to 20° C., for example, a Tg ranging from −100° C. to 20° C., preferably less than or equal to 15° C., especially ranging from −80° C. to 15° C. and better still less than or equal to 10° C., for example ranging from −100° C. to 10° C., especially ranging from −30° C. to 10° C.

The second block is totally or partially derived from one or more second monomers, which are such that the homopolymer prepared from these monomers has a glass transition temperature of less than or equal to 20° C.

This block may also be referred to as a "flexible block".

The monomer with a Tg of less than or equal to 20° C. (known as the second monomer) is preferably chosen from the following monomers:
- the acrylates of formula $CH_2=CHCOOR_3$, $R_3$ representing a linear or branched $C_1$ to $C_{12}$ unsubstituted alkyl group, with the exception of the tert-butyl group, in which one or more heteroatoms chosen from O, N and S are optionally intercalated,
- the methacrylates of formula $CH_2=C(CH_3)-COOR_4$, $R_4$ representing a linear or branched $C_6$ to $C_{12}$ unsubstituted alkyl group, with the exception of the tert-butyl group, in which one or more heteroatoms chosen from O, N and S are optionally intercalated,
- the vinyl esters of formula $R_5-CO-O-CH=CH_2$, in which $R_5$ represents a linear or branched $C_4$ to $C_{12}$ alkyl group,
- ethers of vinyl alcohol and of a $C_4$ to $C_{12}$ alcohol,
- N—($C_4$ to $C_{12}$)alkyl acrylamides, such as N-octylacrylamide, and
- mixtures thereof.

The preferred monomers with a Tg of less than or equal to 20° C. are isobutyl acrylate, 2-ethylhexyl acrylate or mixtures thereof in all proportions.

Each of the first and second blocks may contain in small proportion at least one constituent monomer of the other block.

Thus, the first block may contain at least one constituent monomer of the second block, and vice versa.

Each of the first and/or second blocks may comprise, in addition to the monomers indicated above, one or more other monomers known as additional monomers, which are different from the main monomers mentioned above.

The nature and amount of this or these additional monomer(s) are chosen such that the block in which they are present has the desired glass transition temperature.

This additional monomer is chosen, for example, from:
ethylenically unsaturated monomers comprising at least one tertiary amine function, such as 2-vinylpyridine, 4-vinylpyridine, dimethylaminoethyl methacrylate, diethylaminoethyl methacrylate, dimethylaminopropylmethacrylamide, and salts thereof, the methacrylates of formula $CH_2=C(CH_3)-COOR_6$ in which $R_6$ represents a linear or branched alkyl group containing from 1 to 4 carbon atoms, such as a methyl, ethyl, propyl or isobutyl group, the said alkyl group being substituted with one or more substituents chosen from hydroxyl groups (for instance 2-hydroxypropyl methacrylate and 2-hydroxyethyl methacrylate) and halogen atoms (Cl, Br, I or F), such as trifluoroethyl methacrylate, the methacrylates of formula $CH_2=C(CH_3)-COOR_9$, $R_9$ representing a linear or branched $C_6$ to $C_{12}$ alkyl group in which one or more heteroatoms chosen from O, N and S are optionally intercalated, the said alkyl group being substituted with one or more substituents chosen from hydroxyl groups and halogen atoms (Cl, Br, I or F), the acrylates of formula $CH_2=CHCOOR_{10}$, $R_{10}$ representing a linear or branched $C_1$ to $C_{12}$ alkyl group substituted with one or more substituents chosen from hydroxyl groups and halogen atoms (Cl, Br, I and F), such as 2-hydroxypropyl acrylate and 2-hydroxyethyl acrylate, or $R_{10}$ represents a $C_1$ to $C_{12}$ alkyl-O-POE (polyoxyethylene) with repetition of the oxyethylene unit 5 to 10 times, for example methoxy-POE, or $R_8$ represents a polyoxyethylenated group comprising from 5 to 10 ethylene oxide units.

In particular, the first block may comprise as additional monomer
(meth)acrylic acid, preferably acrylic acid,
tert-butyl acrylate,
the methacrylates of formula $CH_2=C(CH_3)-COOR_1$, in which $R_1$ represents a linear or branched unsubstituted alkyl group containing from 1 to 4 carbon atoms, such as a methyl, ethyl, propyl or isobutyl group,
the (meth)acrylamides of formula:

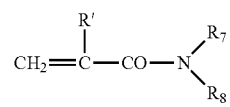

in which $R_7$ and $R_8$, which may be identical or different, each represent a hydrogen atom or a linear or branched $C_1$ to $C_{12}$ alkyl group such as an n-butyl, t-butyl, isopropyl, isohexyl, isooctyl or isononyl group; or $R_7$ represents H and $R_8$ represents a 1,1-dimethyl-3-oxobutyl group, and R' denotes H or methyl. Examples of monomers that may be mentioned include N-butylacrylamide, N-tert-butylacrylamide, N-isopropylacrylamide, N,N-dimethylacrylamide and N,N-dibutylacrylamide, and mixtures thereof.

The additional monomer may represent 0.5% to 30% by weight relative to the weight of the polymer. According to one embodiment, the polymer used in the present invention does not contain any additional monomer.

Preferably, the polymer used in the present invention comprises at least isobornyl acrylate and isobornyl methacrylate monomers in the first block and isobutyl acrylate and acrylic acid monomers in the second block.

Preferably, the polymer comprises at least isobornyl acrylate and isobornyl methacrylate monomers in equivalent weight proportion in the first block and isobutyl acrylate and acrylic acid monomers in the second block.

Preferably, the polymer comprises at least isobornyl acrylate and isobornyl methacrylate monomers in equivalent weight proportion in the first block and isobutyl acrylate and acrylic acid monomers in the second block, the first block representing 70% by weight of the polymer.

Preferably, the polymer comprises at least isobornyl acrylate and isobornyl methacrylate monomers in equivalent weight proportion in the first block and isobutyl acrylate and acrylic acid monomers in the second block. Preferably, the block with a Tg of greater than 40° C. represents 70% by weight of the polymer, and acrylic acid represents 5% by weight of the polymer.

According to one embodiment, the first block does not comprise any additional monomer.

According to a preferred embodiment, the second block comprises acrylic acid as additional monomer. In particular, the second block is advantageously obtained from an acrylic acid monomer and from at least one other monomer with a Tg of less than or equal to 20° C.

The block copolymer may advantageously comprise more than 2% by weight of acrylic acid monomers, and especially from 2% to 15% by weight, for example from 3% to 15% by weight, in particular from 4% to 15% by weight or even from 4% to 10% by weight of acrylic acid monomers, relative to the total weight of the said copolymer.

The constituent monomers of the second block and the proportions thereof are preferably chosen such that the glass transition temperature of the second block is less than or equal to 20° C.

Intermediate Segment

The intermediate segment (also known as the intermediate block) connects the first block and the second block of the polymer used according to the present invention. The intermediate segment results from the polymerization:

i) of the first monomer(s), and optionally of the additional monomer(s), which remain available after their polymerization to a maximum degree of conversion of 90% to form the first block, and ii) of the second monomer(s), and optionally of the additional monomer(s), added to the reaction mixture.

The formation of the second block is initiated when the first monomers no longer react or are no longer incorporated into the polymer chain either because they are all consumed or because their reactivity no longer allows them to be.

Thus, the intermediate segment comprises the first available monomers, resulting from a degree of conversion of these first monomers of less than or equal to 90%, during the introduction of the second monomer(s) during the synthesis of the polymer.

The intermediate segment of the block polymer is a statistical polymer (which may also be referred to as a statistical block). This means that it comprises a statistical distribution of the first monomer(s) and of the second monomer(s) and also of the additional monomer(s) that may be present.

Thus, the intermediate segment is a statistical block, as are the first block and the second block if they are not homopolymers (i.e. if they are both formed from at least two different monomers).

Process for Preparing the Copolymer

The block ethylenic copolymer used according to the present invention is prepared by free radical polymerization, according to the techniques that are well known for this type of polymerization.

The free radical polymerization is performed in the presence of an initiator, whose nature is adapted, in a known manner, as a function of the desired polymerization temperature and of the polymerization solvent. In particular, the initiator may be chosen from initiators containing a peroxide fiction, redox couples, or other radical polymerization initiators known to those skilled in the art.

In particular, examples of initiators containing a peroxide function that may be mentioned include:

peroxyesters, such as tert-butyl peroxyacetate, tert-butyl perbenzoate, tert-butyl peroxy-2-ethylhexanoate (Trigonox 21S from Akzo Nobel) and 2,5-bis(2-ethylhexanoylperoxy)-2,5-dimethylhexane (Trigonox 141 from Akzo Nobel);

peroxydicarbonates, such as diisopropyl peroxydicarbonate;

peroxy ketones, such as methyl ethyl ketone peroxide;

hydroperoxides, such as hydrogen peroxide ($H_2O_2$) and tert-butyl hydroperoxide;

diacyl peroxides, such as acetyl peroxide and benzoyl peroxide;

dialkyl peroxides, such as di-tert-butyl peroxide;

inorganic peroxides, such as potassium peroxodisulfate ($K_2S_2O_8$).

An example of an initiator in the form of a redox couple that may be mentioned is the potassium thiosulfate+potassium peroxodisulfate couple.

According to one preferred embodiment, the initiator is chosen from organic peroxides comprising from 8 to 30 carbon atoms. Preferably, the initiator used is 2,5-bis(2-ethylhexanoylperoxy)-2,5-dimethylhexane sold under the reference Trigonox® 141 by the company Akzo Nobel.

The block copolymer used according to the present invention is prepared by free-radical polymerization rather than by controlled or living polymerization. In particular, the polymerization of the block ethylenic copolymer is performed in the absence of control agents, and in particular in the absence of control agents conventionally used in living or controlled polymerization processes, for instance nitroxides, alkoxyamines, dithioesters, dithiocarbamates, dithiocarbonates or xanthates, trithiocarbonates and copper-based catalysts.

As indicated previously, the intermediate segment is a statistical block, as are the first block and the second block if they are not homopolymers (i.e. if they are both formed from at least two different monomers).

The block copolymer may be prepared by free-radical polymerization, and in particular via a process that consists in mixing, in the same reactor, a polymerization solvent, an initiator, at least one monomer with a glass transition temperature of greater than or equal to 40° C. and at least one monomer with a glass transition temperature of less than or equal to 20° C., according to the following sequence:

some of the polymerization solvent and optionally some of the initiator and of the monomers of the first addition are placed in the reactor, and the mixture is heated to a reaction temperature of between 60 and 120° C., the said at least one first monomer with a Tg of greater than or equal to 40° C. and optionally some of the initiator are then introduced, in a first addition, and the mixture is left to react for a time T corresponding to a maximum degree of conversion of the said monomers of 90%, more polymerization initiator and the said at least one second monomer with a glass transition temperature of less than or equal to 20° C. are then placed in the reactor in a second addition, and the mixture is left to react for a time T' after which the degree of conversion of the said monomers reaches a plateau, the reaction mixture is cooled to room temperature.

Preferably, the copolymer may be prepared by free-radical polymerization, in particular via a process that consists in mixing, in the same reactor, a polymerization solvent, an initiator, an acrylic acid monomer, at least one monomer with a glass transition temperature of less than or equal to 20° C., at least one acrylate monomer of formula $CH_2=CH-COOR$ in which $R_2$ represents a $C_4$ to $C_{12}$ cycloalkyl group, and at least one methacrylate monomer of formula $CH_2=C(CH_3)-COOR'_2$ in which $R'_2$ represents a $C_4$ to $C_{12}$ cycloalkyl group, according to the following sequence of steps:

- some of the polymerization solvent and optionally some of the initiator and of the monomers of the first addition are placed in the reactor, and the mixture is heated to a reaction temperature of between 60 and 120° C.,
- the said at least one acrylate monomer of formula $CH_2=CH-COOR_2$ and the said at least one methacrylate monomer of formula $CH_2=C(CH_3)-COOR'_2$ as monomers with a Tg of greater than or equal to 40° C., and optionally some of the initiator, are then introduced, in a first addition, and the mixture is left to react for a time T corresponding to a maximum degree of conversion of the said monomers of 90%,
- more polymerization initiator, the acrylic acid monomer and the said at least one second monomer with a glass transition temperature of less than or equal to 20° C. are then placed in the reactor, in a second addition, and the mixture is left to react for a time T' after which the degree of conversion of the said monomers reaches a plateau,
- the reaction mixture is cooled to room temperature.

The term "polymerization solvent" means a solvent or a mixture of solvents. In particular, as polymerization solvents that may be used, mention may be made of:

- ketones that are liquid at room temperature, such as methyl ethyl ketone, methyl isobutyl ketone, diisobutyl ketone, isophorone, cyclohexanone or acetone;
- propylene glycol ethers that are liquid at room temperature, such as propylene glycol monomethyl ether, propylene glycol monomethyl ether acetate or dipropylene glycol mono-n-butyl ether;
- short-chain esters (containing from 3 to 8 carbon atoms in total) such as ethyl acetate, methyl acetate, propyl acetate, n-butyl acetate or isopentyl acetate;
- ethers that are liquid at room temperature, such as diethyl ether, dimethyl ether or dichlorodiethyl ether;
- alkanes that are liquid at room temperature, such as decane, heptane, dodecane, isododecane, cyclohexane or isohexadecane;
- cyclic aromatic compounds that are liquid at room temperature, such as toluene or xylene; aldehydes that are liquid at room temperature, such as benzaldehyde or acetaldehyde; and
- mixtures thereof.

Conventionally, the polymerization solvent is a volatile oil with a flash point of less than 80° C. The flash point is measured in particular according to standard ISO 3679.

The polymerization solvent may be chosen especially from ethyl acetate, butyl acetate, alcohols such as isopropanol or ethanol, and aliphatic alkanes such as isododecane, and mixtures thereof. Preferably, the polymerization solvent is a mixture of butyl acetate and isopropanol or isododecane.

According to another embodiment, the copolymer may be prepared by free-radical polymerization according to a preparation process that consists in mixing, in the sane reactor, a polymerization solvent, an initiator, at least one monomer with a glass transition temperature of less than or equal to 20° C., and at least one monomer with a Tg of greater than or equal to 40° C., according to the following sequence of steps:

- some of the polymerization solvent and optionally some of the initiator and of the monomers of the first addition are placed in the reactor, and the mixture is heated to a reaction temperature of between 60 and 120° C.,
- the said at least one monomer with a glass transition temperature of less than or equal to 20° C. and optionally some of the initiator are then introduced, in a first addition, and the mixture is left to react for a time T corresponding to a maximum degree of conversion of the said monomers of 90%,
- more polymerization initiator and the said at least one monomer with a Tg of greater than or equal to 40° C. are then placed in the reactor, in a second addition, and the mixture is left to react for a time T' after which the degree of conversion of the said monomers reaches a plateau,
- the reaction mixture is cooled to room temperature.

According to one preferred embodiment, the copolymer may be prepared by free-radical polymerization according to a preparation process that consists in mixing, in the same reactor, a polymerization solvent, an initiator, an acrylic acid monomer, at least one monomer with a glass transition temperature of less than or equal to 20° C., at least one monomer with a Tg of greater than or equal to 40° C., and, in particular as monomers with a Tg of greater than or equal to 40° C., at least one acrylate monomer of formula $CH_2=CH-COOR_2$ in which $R_2$ represents a $C_4$ to $C_{12}$ cycloalkyl group, and at least one methacrylate monomer of formula $CH_2=C(CH_3)-COOR'_2$ in which $R'_2$ represents a $C_4$ to $C_{12}$ cycloalkyl group, according to the following sequence of steps:

- some of the polymerization solvent and optionally some of the initiator and of the monomers of the first addition are placed in the reactor, and the mixture is heated to a reaction temperature of between 60 and 120° C.,
- the acrylic acid monomer and the said at least one monomer with a glass transition temperature of less than or equal to 20° C. and optionally some of the initiator are then introduced, in a first addition, and the mixture is left to react for a time T corresponding to a maximum degree of conversion of the said monomers of 90%,
- more polymerization initiator, the said at least one acrylate monomer of formula $CH_2=CH-COOR_2$ and the said at least one methacrylate monomer of formula $CH_2=C(CH_3)-COOR'_2$ as monomers with a Tg of greater than or equal to 40° C. are then placed in the reactor, in a second addition, and the mixture is left to react for a time T' after which the degree of conversion of the said monomers reaches a plateau,
- the reaction mixture is cooled to room temperature.

The polymerization temperature is preferably about 90° C.

The reaction time after the second addition is preferably between 3 and 6 hours.

Preferably, the block ethylenic copolymer may be present in the composition in an active material content ranging from 0.1% to 20%, better still from 0.5% to 15%, better still from 1% to 12% and even better still from 2% to 10% by weight relative to the total weight of the composition.

Distillation of the Synthesis Solvent

It is possible to perform a step of total or partial removal of the said volatile oil or solvent (conventionally isododecane). This is then performed in particular by distillation, optionally under vacuum, and optional addition of non-volatile hydrocarbon-based ester oil comprising at least 16 carbon atoms and having a molar mass of less than 650 g/mol, such as octyldodecyl neopentanoate (especially 2-octyldodecyl neopentanoate).

This step is performed at elevated temperature and optionally under vacuum to distil off a maximum amount of volatile synthesis solvent, and is known to those skilled in the art.

(3) Vinyl Polymer Comprising at Least One Carbosiloxane Dendrimer Derivative

According to one particular embodiment, a cosmetic composition used according to the present invention may comprise, as a hydrophobic film-forming polymer, at least one vinyl polymer comprising at least one carbosiloxane dendrimer-based unit.

The vinyl polymer used according to the present invention especially has a backbone and at least one side chain, which comprises a carbosiloxane dendrimer-based unit having a carbosiloxane dendrimer structure.

Vinyl polymers comprising at least one carbosiloxane dendrimer unit as described in patent applications WO 03/045 337 and EP 963 751 by the company Dow Corning may be used in particular.

The term "carbosiloxane dendrimer structure" in the context of the present invention represents a structure with branched groups of high molecular masses, the said structure having high regularity in the radial direction starting from the bond to the backbone. Such carbosiloxane dendrimer structures are described in the form of a highly branched siloxane-silylalkylene copolymer in the laid-open Japanese patent application Kokai 9-171 154.

A vinyl polymer used according to the present invention may contain carbosiloxane dendrimer-based units that may be represented by the following general formula:

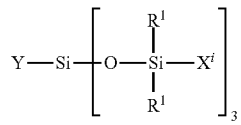

in which $R^1$ represents an aryl group or an alkyl group containing from 1 to 10 carbon atoms, and $X^i$ represents a silylalkyl group which, when i=1, is represented by the formula:

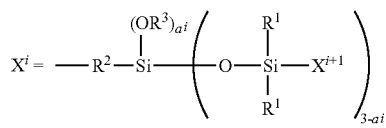

in which $R^1$ is the same as defined above, $R^2$ represents an alkylene group containing from 2 to 10 carbon atoms, $R^3$ represents an alkyl group containing from 1 to 10 carbon atoms, $X^{i+1}$ represents a hydrogen atom, an alkyl group containing from 1 to 10 carbon atoms, an aryl group or the silylalkyl group defined above with i=i+1; i is an integer from 1 to 10 which represents the generation of the said silylalkyl group, and $a^i$ is an integer from 0 to 3; Y represents a radical-polymerizable organic group chosen from:

organic groups containing a methacrylic group or an acrylic group and that are represented by the formulae:

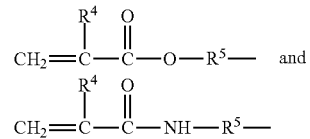

in which $R^4$ represents a hydrogen atom or an alkyl group, $R^5$ represents an alkylene group containing from 1 to 10 carbon atoms, such as a methylene group, an ethylene group, a propylene group or a butylene group, the methylene group and the propylene group being preferred; and organic groups containing a styryl group and that are represented by the formula:

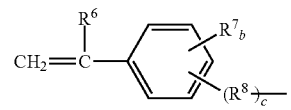

in which $R^6$ represents a hydrogen atom or an alkyl group, $R^7$ represents an alkyl group containing from 1 to 10 carbon atoms, such as a methyl group, an ethyl group, a propyl group or a butyl group, the methyl group being preferred, $R^8$ represents an alkylene group containing from 1 to 10 carbon atoms, such as a methylene group, an ethylene group, a propylene group or a butylene group, the ethylene group being preferred, b is an integer from 0 to 4, and c is 0 or 1 such that if c is 0, $—(R^8)_c—$ represents a bond.

According to one embodiment, $R^1$ may represent an aryl group or an alkyl group containing from 1 to 10 carbon atoms. The alkyl group may preferably be represented by a methyl group, an ethyl group, a propyl group, a butyl group, a pentyl group, an isopropyl group, an isobutyl group, a cyclopentyl group or a cyclohexyl group. The aryl group may preferably be represented by a phenyl group and a naphthyl group. The methyl and phenyl groups are more particularly preferred, and the methyl group is preferred among all.

A vinyl polymer containing at least one carbosiloxane dendrimer-based unit has a molecular side chain containing a carbosiloxane dendrimer structure, and may be the product of polymerization of:

(A) from 0 to 99.9 parts by weight of a vinyl monomer; and (B) from 100 to 0.1 part by weight of a carbosiloxane dendrimer containing a radical-polymerizable organic group, represented by the general formula:

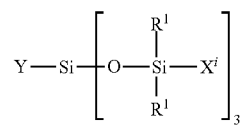

in which Y represents a radical-polymerizable organic group, $R^1$ represents an aryl group or an alkyl group containing from 1 to 10 carbon atoms, and $X^i$ represents a silylalkyl group which, when i=1, is represented by the formula:

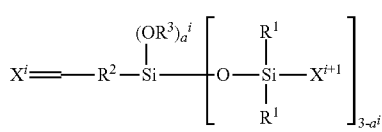

in which R¹ is the same as defined above, R² represents an alkylene group containing from 2 to 10 carbon atoms, R³ represents an alkyl group containing from 1 to 10 carbon atoms, $X^{i+1}$ represents a hydrogen atom, an alkyl group containing from 1 to 10 carbon atoms, an aryl group, or the silylalkyl group defined above with i=i+1; i is an integer from 1 to 10 that represents the generation of the said silylalkyl group, and $a^i$ is an integer from 0 to 3;

in which the said radical-polymerizable organic group contained in the component (B) is chosen from:

organic groups containing a methacrylic group or an acrylic group and that are represented by the formulae:

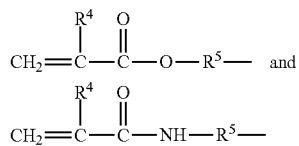

in which R⁴ represents a hydrogen atom or an alkyl group, R⁵ represents an alkylene group containing from 1 to 10 carbon atoms; and organic groups containing a styryl group and that are represented by the formula:

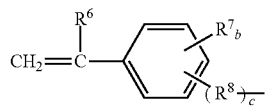

in which R⁶ represents a hydrogen atom or an alkyl group, R⁷ represents an alkyl group containing from 1 to 10 carbon atoms, R⁸ represents an alkylene group containing from 1 to 10 carbon atoms, b is an integer from 0 to 4, and c is 0 or 1, such that if c is 0, —(R⁸)$_c$— represents a bond.

The monomer of vinyl type that is the component (A) in the vinyl polymer is a monomer of vinyl type that contains a radical-polymerizable vinyl group.

There is no particular limitation as regards such a monomer.

The following are examples of this monomer of vinyl type: methyl methacrylate, ethyl methacrylate, n-propyl methacrylate, isopropyl methacrylate or a methacrylate of a lower alkyl analogue; glycidyl methacrylate; butyl methacrylate, butyl acrylate, n-butyl methacrylate, isobutyl methacrylate, tert-butyl acrylate, tert-butyl methacrylate, n-hexyl methacrylate, cyclohexyl methacrylate, 2-ethylhexyl acrylate, 2-ethylhexyl methacrylate, octyl methacrylate, lauryl methacrylate, stearyl acrylate, stearyl methacrylate or a higher-analogue methacrylate; or a higher-analogue methacrylate; vinyl acetate, vinyl propionate or a vinyl ester of a lower fatty acid analogue; vinyl caproate, vinyl 2-ethylhexoate, vinyl laurate, vinyl stearate or an ester of a higher fatty acid analogue; styrene, vinyltoluene, benzyl methacrylate, phenoxyethyl methacrylate, vinyl-pyrrolidone or similar vinylaromatic monomers; methacrylamide, N-methylolmethacrylamide, N-methoxymethylmethacylamide, isobutoxymethoxy-methacrylamide, N,N-dimethylmethacrylamide or similar monomers of vinyl type containing amide groups; hydroxyethyl methacrylate, hydroxypropyl methacrylate or similar monomers of vinyl type containing hydroxyl groups; acrylic acid methacrylic acid, itaconic acid, crotonic acid, fumaric acid, maleic acid or similar monomers of vinyl type containing a carboxylic acid group; tetrahydrofurfuryl methacrylate, butoxyethyl methacrylate, ethoxydiethylene glycol methacrylate, polyethylene glycol methacrylate, polypropylene glycol monomethacrylate, hydroxybutyl vinyl ether cetyl vinyl ether, 2-ethylhexyl vinyl ether or a similar monomer of vinyl type with ether bonds; methacryloxypropyltrimethoxysilane, polydimethylsiloxane containing a methacrylic group on one of its molecular ends, polydimethylsiloxane containing a styryl group on one of its molecular ends, or a similar silicone compound containing unsaturated groups; butadiene; vinyl chloride; vinylidene chloride; methacrylonitrile; dibutyl fumarate; anhydrous maleic acid; anhydrous succinic acid; methacryl glycidyl ether, an organic salt of an amine, an ammonium salt, and an alkali metal salt of methacrylic acid, of itaconic acid, of crotonic acid, of maleic acid or of fumaric acid; a radical-polymerizable unsaturated monomer containing a sulfonic acid group such as a styrenesulfonic acid group; a quaternary ammonium salt derived from methacrylic acid, such as 2-hydroxy-3-methacryloxypropyltrimethylammonium chloride; and a methacrylic acid ester of an alcohol containing a tertiary amine group, such as a methacrylic acid ester of diethylamine.

Multifunctional monomers of vinyl type may also be used.

The following are examples of such compounds: trimethylolpropane trimethacrylate, pentaerythrityl trimethacrylate, ethylene glycol dimethacrylate, tetraethylene glycol dimethacrylate, polyethylene glycol dimethacrylate, 1,4-butanediol dimethacrylate, 1,6-hexanediol dimethacrylate, neopentyl glycol dimethacrylate, trimethylolpropanetrioxyethyl methacrylate, tris(2-hydroxyethyl) isocyanurate dimethacrylate, tris(2-hydroxyethyl) isocyanurate trimethacrylate, polydimethylsiloxane capped with styryl groups containing divinylbenzene groups on both ends, or similar silicone compounds containing unsaturated groups.

A carbosiloxane dendrimer, which is the component (B), may be represented by the following formula:

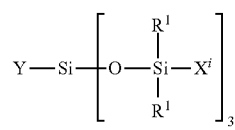

in which Y represents a radical-polymerizable organic group as defined previously.

The following are preferred examples of radical-polymerizable organic groups Y: an acryloxymethyl group, a 3-acryloxypropyl group, a methacryloxymethyl group, a 3-methacryloxypropyl group, a 4-vinylphenyl group, a 3-vinylphenyl group, a 4-(2propenyl)phenyl group, a 3-(2-propenyl)phenyl group, a 2-(4-vinylphenyl)ethyl group, a 2-(3- vinylphenyl)ethyl group, a vinyl group, an allyl group, a methallyl group and a 5-hexenyl group.

R' is as defined previously.

$X^i$ represents a silylalkyl group that is represented by the following formula, when i is equal to 1:

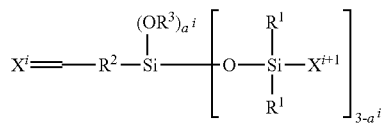

in which $R^1$ is as defined above.

$R^2$ represents an alkylene group containing from 2 to 10 carbon atoms, such as an ethylene group, a propylene group, a butylene group, a hexylene group or a similar linear alkylene group; a methylmethylene group, a methylethylene group, a 1-methylpentylene group, a 1,4-dimethylbutylene group or a similar branched alkylene group. The ethylene, methylethylene, hexylene, 1-methylpentylene and 1,4-dimethylbutylene groups are preferred above all.

$R^3$ represents an alkyl group containing from 1 to 10 carbon atoms, such as methyl, ethyl, propyl, butyl and isopropyl groups.

$X^{i+1}$ represents a hydrogen atom, an alkyl group containing from 1 to 10 carbon atoms, an aryl group or the silylalkyl group with i=i+1.

$a^i$ is an integer from 0 to 3, and i is an integer from 1 to 10 that indicates the generation number, which represents the number of repetitions of the silylalkyl group.

For example, when the generation number is equal to 1, the carbosiloxane dendrimer may be represented by the first general formula shown below, in which Y, $R^1$, $R^2$ and $R^3$ are the same as defined above, $R^{12}$ represents a hydrogen atom or is identical to $R^1$; $a^1$ is identical to $a^i$. Preferably, the mean total number of groups $OR^3$ in a molecule is within the range from 0 to 7.

When the generation number is equal to 2, the carbosiloxane dendrimer may be represented by the second general formula shown below, in which Y, $R^1$, $R^2$, $R^3$ and $R^{12}$ are the same as defined above; $a^1$ and $a^2$ represent the $a^i$ of the indicated generation. Preferably, the mean total number of groups $OR^3$ in a molecule is within the range from 0 to 25.

When the generation number is equal to 3, the carbosiloxane dendrimer is represented by the third general formula shown below, in which Y, $R^1$, $R^2$, $R^3$ and $R^{12}$ are the same as defined above; $a^1$, $a^2$ and $a^3$ represent the $a^i$ of the indicated generation. Preferably, the mean total number of groups $OR^3$ in a molecule is within the range from 0 to 79.

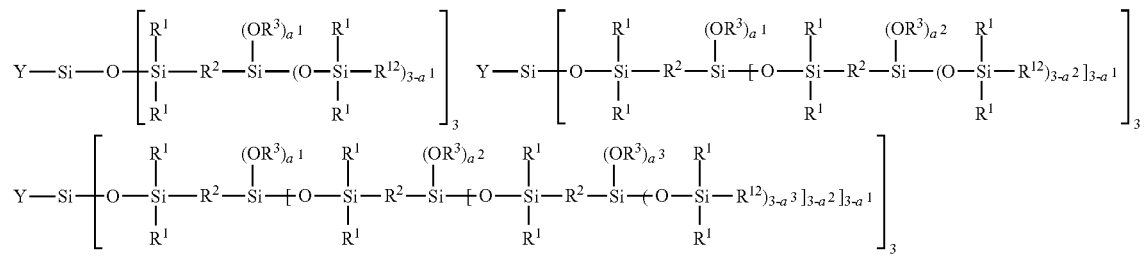

A carbosiloxane dendrimer that contains a radical-polymerizable organic group may be represented by the following mean structural formulae:

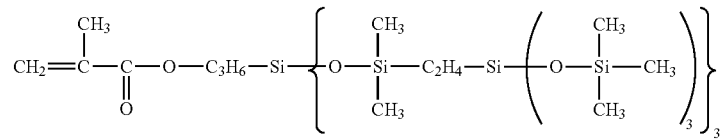

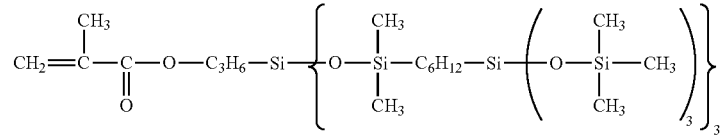

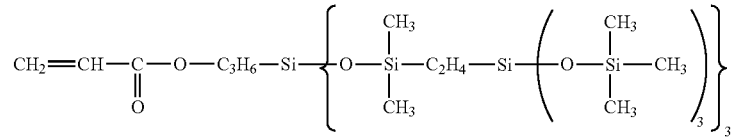

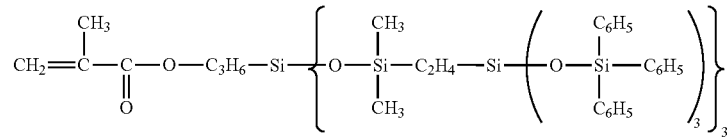

-continued

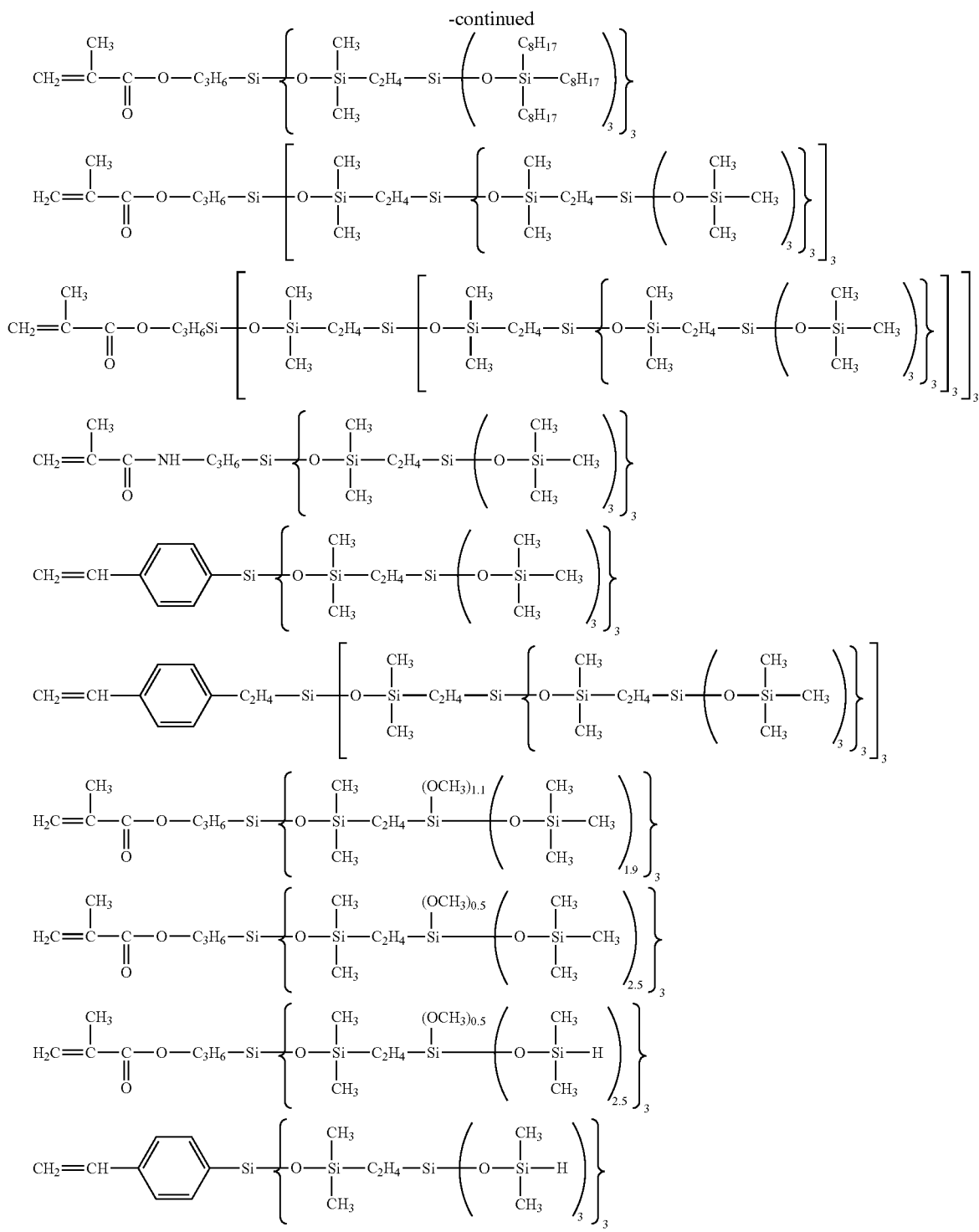

The carbosiloxane dendrimer may be manufactured according to the process for manufacturing a branched silalkylene siloxane described in Japanese patent application Hei 9-171 154.

For example, it may be produced by subjecting an organosilicon compound containing a hydrogen atom linked to a silicon atom, represented by the following general formula:

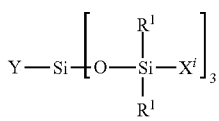

and an organosilicon compound containing an alkenyl group, to a hydrosilylation reaction.

In the above formula, the organosilicon compound may be represented by 3-methacyloxypropyltris(dimethylsiloxy)silane, 3-acryloxypropyltris(dimethylsiloxy)silane and 4-vinylphenyltris(dimethylsiloxy)silane. The organosilicon compound that contains an alkenyl group may be represented by vinyltris(trimethylsiloxy)silane, vinyltris(dimethylphenylsiloxy)silane, and 5-hexenyltris(trimethylsiloxy)silane.

The hydrosilylation reaction is performed in the presence of a chloroplatinic acid, a complex of vinylsiloxane and of platinum, or a similar transition metal catalyst.

A vinyl polymer containing at least one carbosiloxane dendrimer-based unit may be chosen from polymers such that the carbosiloxane dendrimer-based unit is a carbosiloxane dendritic structure represented by formula (I):

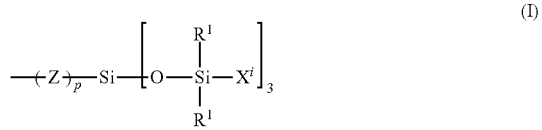

in which Z represents a divalent organic group, "p" is 0 or 1, $R^1$ is an aryl or alkyl group containing from 1 to 10 carbon atoms and $X^i$ is a silylalkyl group represented by formula (II):

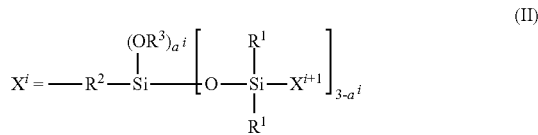

in which $R^1$ is as defined above, $R^2$ is an alkylene group containing from 1 to 10 carbon atoms, $R^3$ is an alkyl group containing from 1 to 10 carbon atoms and $X^{i+1}$ is a group chosen from the group comprising hydrogen atoms, aryl groups and alkyl groups containing up to 10 carbon atoms, and silylalkyl groups $X^i$ in which the power "i" is an integer from 1 to 10 indicating the generation of the starting silylalkyl group in each carbosiloxane dendritic structure with a value of 1 for the group $X^i$ in formula (I) and the index "$a^i$" is an integer from 0 to 3.

In a vinyl polymer containing at least one carbosiloxane dendrimer-based unit, the polymerization ratio between the components (A) and (B), in terms of the weight ratio between (A) and (B), may be within a range from 0/100 to 99.9/0.1, or even from 0.1/99.9 to 99.9/0.1 and preferably within a range from 1/99 to 99/1. A ratio between the components (A) and (B) of 0/100 means that the compound becomes a homopolymer of component (B).

A vinyl polymer containing at least one carbosiloxane dendrimer-based unit may be obtained by copolymerization of the components (A) and (B), or by polymerization of component (B) alone.

The polymerization may be a five-radical polymerization or an ionic polymerization, but free-radical polymerization is preferred.

The polymerization may be performed by bringing about a reaction between the components (A) and (B) in a solution for a period of from 3 to 20 hours in the presence of a radical initiator at a temperature of from 50° C. to 150° C.

A suitable solvent for this purpose is hexane, octane, decane, cyclohexane or a similar aliphatic hydrocarbon benzene, toluene, xylene or a similar aromatic hydrocarbon; diethyl ether, dibutyl ether, tetrahydrofuran, dioxane or similar ethers; acetone, methyl ethyl ketone, methyl isobutyl ketone, diisobutyl ketone or similar ketones; methyl acetate, ethyl acetate, butyl acetate, isobutyl acetate or similar esters; methanol, ethanol, isopropanol, butanol or similar alcohols; octamethylcyclotetrasiloxane, decamethylcyclopentasiloxane, hexamethyldisiloxane, octamethyltrisiloxane or a similar organosiloxane oligomer.

A radical initiator may be any compound known in the art for standard free-radical polymerization reactions. Specific examples of such radical initiators are 2,2'-obis(isobutyronitrile), 2,2'-azobis(2-methylbutyronitrile), 2,2'-azobis(2,4-dimethylvaleronitrile) or similar compounds of azobis type; benzoyl peroxide, lauroyl peroxide, tert-butyl peroxybenzoate, tert-butyl peroxy-2-ethylhexanoate or a similar organic peroxide. These radical initiators may be used alone or in a combination of two or more. The radical initiators may be used in an amount of from 0.1 to 5 parts by weight per 100 parts by weight of the components (A) and (B). A chain-transfer agent may be added. The chain-transfer agent may be 2-mercaptoethanol, butyl mercaptan, n-dodecyl mercaptan, 3-mercaptopropyltrimethoxysilane, a polydimethylsiloxane containing a mercaptopropyl group or a similar compound of mercapto type; methylene chloride, chloroform, carbon tetrachloride, butyl bromide, 3-chloropropyltrimethoxysilane or a similar halogenated compound.

In the manufacture of the polymer of vinyl type, after the polymerization, the residual unreacted vinyl monomer may be removed under conditions of heating under vacuum.

To facilitate the preparation of the mixture of the starting material of cosmetic products, the number-average molecular mass of the vinyl polymer containing a carbosiloxane dendrimer may be chosen within the range between 3000 and 2 000 000 and preferably between 5000 and 800 000. It may be a liquid, a gum, a paste, a solid, a powder or any other form. The preferred forms are solutions formed from the dilution of a dispersion or of a powder in solvents.

The vinyl polymer may be a dispersion of a polymer of vinyl type having a carbosiloxane dendrimer structure in its molecular side chain, in a liquid such as a silicone oil, an organic oil, an alcohol or water.

The silicone oil may be a dimethylpolysiloxane with the two molecular ends capped with trimethylsiloxy groups, a copolymer of methylphenylsiloxane and of dimethylsiloxane having the two molecular ends capped with trimethylsiloxy groups, a copolymer of methyl-3,3,3-trifluoropropylsiloxane and of dimethylsiloxane having the two molecular ends capped with trimethylsiloxy groups, or similar unreactive linear silicone oils, and also hexamethylcyclotrisiloxane, octamethylcyclotetrasiloxane, decamethylcyclopentasiloxane, dodecamethylcyclohexasiloxane or a similar cyclic compound. In addition to the unreactive silicone oils, modified polysiloxanes containing functional groups such as silanol groups, amino groups and polyether groups on the ends or within the molecular side chains may be used.

The organic oils may be isododecane, liquid paraffin, isoparaffin, hexyl laurate, isopropyl myristate, myristyl myristate, cetyl myristate, 2-octyldodecyl myristate; isopropyl palmitate, 2-ethylhexyl palmitate, butyl stearate, decyl oleate, 2-octyldodecyl oleate, myristyl lactate, cetyl lactate, lanolin acetate, stearyl alcohol, cetostearyl alcohol, oleyl alcohol, avocado oil almond oil, olive oil, cocoa oil, jojoba oil, gum oil, sunflower oil, soybean oil, camellia oil, squalane, castor oil, cottonseed oil, coconut oil, egg yolk oil, polypropylene glycol monooleate, neopentyl glycol 2-ethylhexanoate or a similar glycol ester oil; triglyceryl isostearate, the triglyceride of a fatty acid of coconut oil, or a similar oil of a polyhydric alcohol ester, polyoxyethylene lauryl ether, polyoxypropylene cetyl ether or a similar polyoxyalkylene ether.

The alcohol may be any type that is suitable for use in combination with a cosmetic product starting material. For example, it may be methanol, ethanol, butanol, isopropanol or similar lower alcohols.

A solution or a dispersion of the alcohol should have a viscosity within the range from 10 to $10^9$ mPa at 25° C. To improve the sensory use properties in a cosmetic product, the viscosity should be within the range from 100 to $5\times10^8$ mPa·s.

The solutions and dispersions may be readily prepared by mixing the vinyl polymer having a carbosiloxane dendrimer structure with a silicone oil, an organic oil, an alcohol or water. The liquids may be present in the step of polymerization of a vinyl polymer containing at least one carbosiloxane dendrimer-based unit. In this case, the unreacted residual vinyl monomer should be completely removed by heat treatment of the solution or dispersion under atmospheric pressure or reduced pressure.

In the case of a dispersion, the dispersity of the polymer of vinyl type may be improved by adding a surfactant.

Such an agent may be hexylbenzenesulfonic acid, octylbenzenesulfonic acid, decylbenzenesulfonic acid, dodecylbenzenesulfonic acid, cetylbenzenesulfonic acid, myristylbenzenesulfonic acid or anionic surfactants of the sodium salts of these acids; octyltrimethylammonium hydroxide, dodecyltrimethylammonium hydroxide, hexadecyltrimethylammonium hydroxide, octyldimethylbenzylammonium hydroxide, decyldimethylbenzylammonium hydroxide, dioctadecyldimethylammonium hydroxide, beef tallow-trimethylammonium hydroxide, coconut oil-trimethylammonium hydroxide, or a similar cationic surfactant a polyoxyalkylene alkyl ether, a polyoxyalkylenealkylphenol, a polyoxyalkylene alkyl ester, the sorbitol ester of polyoxyalkylene, polyethylene glycol, polypropylene glycol, an ethylene oxide additive of diethylene glycol trimethylnonanol, and nonionic surfactants of polyester type, and also mixtures.

In addition, the solvents and dispersions may be combined with iron oxide suitable for use with cosmetic products, or a similar pigment, and also zinc oxide, titanium oxide, silicon oxide, mica, talc or similar mineral oxides in powder form. In the dispersion, a mean particle diameter of the polymer of vinyl type may be within a range of between 0.001 and 100 microns and preferably between 0.01 and 50 microns. The reason for this is that, outside the recommended range, a cosmetic product mixed with the emulsion will not have a nice enough feel on the skin or to the touch, or sufficient spreading properties or a pleasant feel.

A vinyl polymer contained in the dispersion or the solution may have a concentration in the range between 0.1% and 95% by weight and preferably between 5% and 85% by weight. However, to facilitate the handling and the preparation of the mixture, the range should preferably be between 10% and 75% by weight.

According to one preferred mode, a vinyl polymer that is suitable for use in the present invention may be one of the polymers described in the examples of patent application EP 0 963 751.

According to one preferred embodiment, a vinyl polymer grafted with a carbosiloxane dendrimer may be the product of polymerization of:
(A) from 0.1 to 99 parts by weight of one or more acrylate or methacrylate monomers; and (B) from 100 to 0.1 part by weight of an acrylate or methacrylate monomer of a tris[tri(trimethylsiloxy)silylethyldimethylsiloxy]silylpropyl carbosiloxane dendrimer.

According to one embodiment, a vinyl polymer containing at least one carbosiloxane dendrimer-based unit may comprise a tris[tris(trimethylsiloxy)silylethyldimethylsiloxy]sil-ylpropyl carbosiloxane dendrimer-based unit corresponding to one of the formulae:

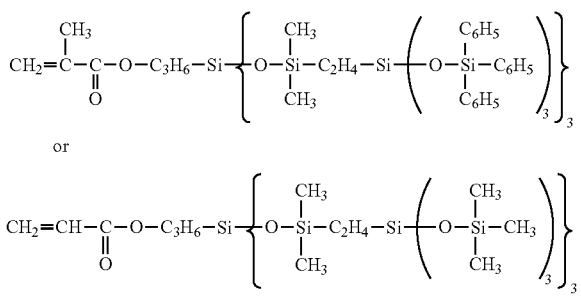

According to one preferred mode, a vinyl polymer containing at least one carbosiloxane dendrimer-based unit used in the present invention comprises at least one butyl acrylate monomer.

According to one embodiment, a vinyl polymer may also comprise at least one fluoro organic group. A fluoro vinyl polymer may be one of the polymers described in the examples of patent application WO 03/045 337.

According to one preferred embodiment, a vinyl polymer grafted in the sense of the present invention may be conveyed in an oil or a mixture of oils, which are preferably volatile, chosen in particular from silicone oils and hydrocarbon-based oils, and mixtures thereof.

According to one particular embodiment, a silicone oil that is suitable for use in the present invention may be cyclopentasiloxane.

According to another particular embodiment, a hydrocarbon-based oil that is suitable for use in the present invention may be isododecane.

Vinyl polymers grafted with at least one carbosiloxane dendrimer-based unit that may be particularly suitable for use in the present invention are the polymers sold under the names TIB 4-100, TIB 4-101, TIB 4-120, TIB 4-130, TIB 4-200, FA 4002 ID (TIB 4-202), TIB 4-220 and FA 4001 CM (TIB 4-230) by the company Dow Corning. The polymers sold under the names FA 4002 ID (TIB 4-202) and FA 4001 CM (TIB 4-230) by the company Dow Corning will preferably be used.

Preferably, the vinyl polymer grafted with at least one carbosiloxane dendrimer-based unit that may be used in a cosmetic composition of the present invention is an acrylate/polytrimethyl siloxymethacrylate copolymer, especially the product sold in isododecane under the name Dow Corning FA 4002 ID Silicone Acrylate by the company Dow Corning.

Preferably, the vinyl polymer comprising at least one carbosiloxane dendrimer derivative may be present in the composition in an active material content ranging from 0.1% to 20%, better still from 1% to 15%, better still from 2% to 12% and even better still from 4% to 10% by weight relative to the total weight of the composition.

(4) Copolymer Comprising Carboxylate Groups and Polydimethylsiloxane Groups

According to one particular embodiment, a cosmetic composition according to the present invention may comprise, as a hydrophobic film-forming polymer, at least one copolymer comprising carboxylate groups and polydimethylsiloxane groups.

In the present patent application, the expression "copolymer comprising carboxylate groups and polydimethylsiloxane groups" means a copolymer obtained from (a) one or more carboxylic (acid or ester) monomers, and (b) one or more polydimethylsiloxane (PDMS) chains.

In the present patent application, the term "carboxylic monomer" means both carboxylic acid monomers and carboxylic acid ester monomers. Thus, the monomer (a) may be chosen, for example, from acrylic acid, methacrylic acid, maleic acid, fumaric acid, itaconic acid, crotonic acid, esters thereof and mixtures of these monomers. Esters that may be mentioned include the following monomers: acrylate, methacrylate, maleate, fumarate, itaconate and/or crotonate. According to one preferred embodiment of the present invention, the monomers in ester form are more particularly chosen from linear or branched, preferably $C_1$-$C_{24}$ and better still $C_1$-$C_{22}$ alkyl acrylates and methacrylates, the alkyl radical preferably being chosen from methyl, ethyl, stearyl, butyl and 2-ethylhexyl radicals, and mixtures thereof.

Thus, according to one particular embodiment of the present invention, the copolymer comprises as carboxylate groups at least one group chosen from acrylic acid and methacrylic acid, and methyl, ethyl, stearyl, butyl or 2-ethylhexyl acrylate or methacrylate, and mixtures thereof.

In the present patent application, the term "polydimethylsiloxanes" (also known as organopolysiloxanes and abbreviated as PDMS) denotes, in accordance with what is generally accepted, any organosilicon polymer or oligomer of linear structure, of variable molecular weight, obtained by polymerization and/or polycondensation of suitably functionalized silanes, and consisting essentially of a repetition of main units in which the silicon atoms are linked together via oxygen atoms (siloxane bond ≡Si—O—Si≡), comprising trimethyl radicals directly linked via a carbon atom to the said silicon atoms. The PDMS chains that may be used to obtain the copolymer used according to the present invention comprise at least one polymerizable radical group, preferably located on at least one of the ends of the chain, i.e. the PDMS may contain, for example, a polymerizable radical group on the two ends of the chain or one polymerizable radical group on one end of the chain and one trimethylsilyl end group on the other end of the chain. The radical-polymerizable group may especially be an acrylic or methacrylic group, in particular a group $CH_2$=$CR_1$—CO—O—$R_2$, in which $R_1$ represents a hydrogen or a methyl group, and $R_2$ represents —$CH_2$—, —$(CH_2)_n$— with n=3, 5, 8 or 10, —$CH_2$—$C(CH_3)$—$CH_2$—, —$CH_2$—$CH_2$—O—$CH_2$—$CH_2$—, —$CH_2$—$CH_2$—O—$CH_2$—$CH_2$—CH($CH_3$)—$CH_2$— or —$CH_2$—$CH_2$—O—$CH_2CH_2$—O—$CH_2$—$CH_2$—$CH_2$—.

The copolymers used in the cosmetic composition of the present invention are generally obtained according to the usual methods of polymerization and grafting, for example by free-radical polymerization (A) of a PDMS comprising at least one polymerizable radical group (for example on one of the ends of the chain or on both ends) and (B) of at least one carboxylic monomer, as described, for example, in documents U.S. Pat. Nos. 5,061,481 and 5,219,560.

The copolymers obtained generally have a molecular weight ranging from about 3000 to 200 000 and preferably from about 5000 to 100 000.

The copolymer used in the cosmetic composition of the present invention may be in its native form or in dispersed form in a solvent such as lower alcohols containing from 2 to 8 carbon atoms, for instance isopropyl alcohol, or oils, for instance volatile silicone oils (for example cyclopentasiloxane).

As copolymers that may be used in the cosmetic composition of the present invention, mention may be made, for example, of copolymers of acrylic acid and of stearyl acrylate containing polydimethylsiloxane grafts, copolymers of stearyl methacrylate containing polydimethylsiloxane grafts, copolymers of acrylic acid and of stearyl methacrylate containing polydimethylsiloxane grafts, copolymers of methyl methacrylate, butyl methacrylate, 2-ethylhexyl acrylate and stearyl methacrylate containing polydimethylsiloxane grafts. As copolymers that may be used in the cosmetic composition of the present invention, mention may be made in particular of the copolymers sold by the company Shin-Etsu under the names KP-561 (CTFA name: acrylates/dimethicone), KP-541 in which the copolymer is dispersed at 60% by weight in isopropyl alcohol (CTFA name: acrylates/dimethicone and isopropyl alcohol), and KP-545 in which the copolymer is dispersed at 30% in cyclopentasiloxane (CTFA name: acrylates/dimethicone and cyclopentasiloxane). According to one preferred embodiment of the present invention, KP561 is preferably used; this copolymer is not dispersed in a solvent, but is in waxy form, its melting point being about 30° C.

Mention may also be made of the grafted copolymer of polyacrylic acid and dimethylpolysiloxane dissolved in isododecane, sold by the company Shin-Etsu under the name KP-550.

Preferably, the copolymer comprising carboxylate groups and polydimethylsiloxane groups may be present in the composition in an active material content ranging from 0.01% to 20%, better still from 0.1% to 15%, better still from 0.5% to 12% and even better still from 1% to 10% by weight relative to the total weight of the composition.

(5) Silicone Resin

According to one embodiment variant, a cosmetic composition according to the present invention may comprise, as a hydrophobic film-forming polymer, at least one silicone resin.

More generally, the term "resin" means a compound whose structure is three-dimensional. "Silicone resins" are also known as "silicone-based resins" or "siloxane resins". Thus, for the purposes of the present invention, a polydimethylsiloxane is not a silicone resin.

The nomenclature of silicone resins (also known as siloxane resins) is known under the name "MDTQ", the resin being described as a function of the various siloxane monomer units that it comprises, each of the letters "MDTQ" characterizing a type of unit.

The letter "M" represents the Monofunctional unit of formula $R_1R_2R_3SiO_{1/2}$, the silicon atom being connected to only one oxygen atom in the polymer comprising this unit.

The letter "D" means a Difunctional unit $R_1R_2SiO_{2/2}$ in which the silicon atom is connected to two oxygen atoms.

The letter "T" represents a Trifunctional unit of formula $R_1SiO_{3/2}$.

Such resins are described, for example, in the "Encyclopaedia of Polymer Science and Engineering, vol. 15, John Wiley & Sons, New York (1989), pp. 265-270 and U.S. Pat.

Nos. 2,676,182, 3,627,851, 3,772,247 and 5,248,739 or alternatively U.S. Pat. Nos. 5,082,706, 5,319,040, 5,302,685 and 4,935,484.

In the M, D and T units defined previously, R, i.e. $R_1$, $R_2$, and $R_3$, represents a hydrocarbon-based radical (especially alkyl) containing from 1 to 10 carbon atoms, a phenyl group, a phenylalkyl group or a hydroxyl group.

Finally, the letter "Q" means a tetrafunctional unit $SiO_{4/2}$ in which the silicon atom is linked to four oxygen atoms, which are themselves linked to the rest of the polymer.

Various silicone resins with different properties may be obtained from these different units, the properties of these polymers varying as a function of the type of monomer (or unit), the nature and number of the radical R, the length of the polymer chain, the degree of branching and the size of the pendent chains.

As silicone resins that may be used in the cosmetic composition according to the present invention, use may be made, for example, of silicone resins of MQ type, of T type or of MQT type.

MQ Resins:

As examples of silicone resins of MQ type, mention may be made of the alkyl siloxysilicates of formula $[(R1)_3SiO_{1/2}]_x(SiO_{4/2})_y$ (MQ units) in which x and y are integers ranging from 50 to 80, and such that the group R1 represents a radical as defined previously, and is preferably an alkyl group containing from 1 to 8 carbon atoms, preferably a methyl group.

As examples of solid silicone resins of MQ type of trimethyl siloxysilicate type, mention may be made of those sold under the reference SR1000 by the company General Electric, under the reference TIMS 803 by the company Wacker, or under the name KF-7312J by the company Shin-Etsu or DC749 or DC593 by the company Dow Corning.

As silicone resins comprising MQ siloxysilicate units, mention may also be made of phenylalkylsiloxysilicate resins, such as phenylpropyldimethylsiloxysilicate (Silshine 151 sold by the company General Electric). The preparation of such resins is described especially in U.S. Pat. No. 5,817,302.

Resins T:

Examples of these silicone resins of type T that may be mentioned include the polysilsesquioxanes of formula $(RSiO_{3/2})_x$ (units T) in which x is greater than 100 and such that the group R is an alkyl group containing from 1 to 10 carbon atoms, the said polysilsesquioxanes also possibly comprising Si—OH end groups.

Polymethylsilsesquioxane resins that may preferably be used are those in which R represents a methyl group, for instance those sold:

by the company Wacker under the reference Resin MK, such as Belsil PMS MK: polymer comprising $CH_3SiO_{3/2}$ repeating units (units T), which may also comprise up to 1% by weight of $(CH_3)_2SiO_{2/2}$ units (units D) and having an average molecular weight of about 10 000 g/mnol, or by the company Shin-Etsu under the reference KR-220L, which are composed of units T of formula $CH_3SiO_{3/2}$ and have Si—OH (silanol) end groups, under the reference KR-242A, which comprise 98% of units T and 2% of dimethyl units D and have Si—OH end groups, or alternatively under the reference KR-251 comprising 88% of units T and 12% of dimethyl units D and have Si—OH end groups.

MQT Resins:

Resins comprising MQT units that are especially known are those mentioned in document U.S. Pat. No. 5,110,890.

A preferred form of resins of MQT type are MQT-propyl (also known as MQTPr) resins. Such resins that may be used in the cosmetic composition according to the present invention are especially the resins described and prepared in patent application WO 2005/075 542, the content of which is incorporated herein by reference.

The MQ-T-propyl resin preferably comprises the following units:

(i) $(R1_3SiO_{1/2})_a$
(ii) $(R2_2SiO_{2/2})_b$
(iii) $(R3SiO_{3/2})_c$ and
(iv) $(SiO_{4/2})_d$
with
R1, R2 and R3 independently representing a hydrocarbon-based radical (especially alkyl) containing from 1 to 10 carbon atoms, a phenyl group, a phenylalkyl group or a hydroxyl group, and preferably an alkyl radical containing from 1 to 8 carbon atoms or a phenyl group,
a being between 0.05 and 0.5,
b being between 0 and 0.3,
c being greater than 0,
d being between 0.05 and 0.6,
a+b+c+d=1, and a, b, c and d being mole fractions,
on condition that more than 40 mol % of the groups R3 of the siloxane resin are propyl groups.

Preferably, the siloxane resin comprises the following units:

(i) $(R1_3SiO_{1/2})_a$
(iii) $(R3SiO_{3/2})_c$ and
(iv) $(SiO_{4/2})_d$
with
R1 and R3 independently representing an alkyl group containing from 1 to 8 carbon atoms, R1 preferably being a methyl group and R3 preferably being a propyl group,
a being between 0.05 and 0.5 and preferably between 0.15 and 0.4,
c being greater than 0 and preferably between 0.15 and 0.4,
d being between 0.05 and 0.6, preferably between 0.2 and 0.6, or alternatively between 0.2 and 0.55,
a+b+c+d=1 and a, b, c and d being mole fractions,
on condition that more than 40 mol % of the groups R3 of the siloxane resin are propyl groups.

The siloxane resins that may be used according to the present invention may be obtained via a process comprising the reaction of:

A) an MQ resin comprising at least 80 mol % of units $(R1_3SiO_{1/2})_a$ and $(SiO_{4/2})_d$
   R1 representing an alkyl group containing from 1 to 8 carbon atoms, an aryl group, a carbinol group or an amino group,
   a and d being greater than 0,
   the ratio a/d being between 0.5 and 1.5;
and
B) a T-propyl resin comprising at least 80 mol % of units $(R3SiO_{3/2})_c$,
   R3 representing an alkyl group containing from 1 to 8 carbon atoms, an aryl group, a carbinol group or an amino group,
   c being greater than 0,
   on condition that at least 40 mol % of the groups R3 are propyl groups,
in which the mass ratio A/B is between 95/5 and 15/85 and the mass ratio A/B is preferably 30/70.

Advantageously, the mass ratio A/B is between 95/5 and 15/85. Preferably, the ratio A/B is less than or equal to 70/30.

These preferred ratios have been proven to produce deposits that are comfortable due to the absence of percolation of the rigid MQ resin particles in the deposit.

Thus, preferably, the silicone resin is chosen from the group comprising:
a) a resin of MQ type, chosen especially from (i) alkyl siloxysilicates, which may be trimethyl siloxysilicates, of formula $[(R1)_3SiO_{1/2}]_x SiO_{4/2})_y$, in which x and y are integers ranging from 50 to 80, and such that the group R1 represents a hydrocarbon-based radical containing from 1 to 10 carbon atoms, a phenyl group, a phenylalkyl group or a hydroxyl group, and preferably is an alkyl group containing from 1 to 8 carbon atoms, preferably a methyl group, and (ii) phenylalkyl siloxysilicate resins, such as phenylpropyldimethyl siloxysilicate, and/or
b) a resin of T type, chosen especially from the polysilsesquioxanes of formula $(RSiO_{3/2})_x$, in which x is greater than 100 and the group R is an alkyl group containing from 1 to 10 carbon atoms, for example a methyl group, the said polysilsesquioxanes also possibly comprising Si—OH end groups, and/or
c) a resin of MQT type, especially of MQT-propyl type, which may comprise units (i) $(R1_3SiO_{1/2})_a$, (ii) $(R2_2SiO_{2/2})_b$, (iii) $(R3SiO_{3/2})_c$ and (iv) $(SiO_{4/2})_d$,
  with R1, R2 and R3 independently representing a hydrocarbon-based radical, especially alkyl, containing from 1 to 10 carbon atoms, a phenyl group, a phenylalkyl group or a hydroxyl group and preferably an alkyl radical containing from 1 to 8 carbon atoms or a phenyl group,
  a being between 0.05 and 0.5,
  b being between 0 and 0.3,
  c being greater than 0,
  d being between 0.05 and 0.6,
  a+b+c+d=1, and a, b, c and d being mole fractions,
  on condition that more than 40 mol % of the groups R3 of the siloxane resin are propyl groups.

Preferably, silicone resin may be present in the composition in an active material content ranging from 0.1% to 20%, better still from 1% to 15%, better still from 2% to 12% and even better still from 4% to 10% by weight relative to the total weight of the composition.

(6) Lipodispersible Polymer in the Form of a Non-Aqueous Dispersion of Polymer Particles According to another embodiment variant, a cosmetic composition according to the present invention may comprise, as a hydrophobic film-forming polymer, at least one polymer chosen from lipodispersible film-forming polymers in the form of non-aqueous dispersions of polymer particles, also known as NADs.

Non-aqueous dispersions of hydrophobic film-forming polymer that may be used include dispersions of particles of a grafted ethylenic polymer; preferably an acrylic polymer, in a liquid oily phase:
  either in the form of ethylenic polymer particles dispersed in the absence of additional stabilizer at the surface of the particles, as described especially in document WO 04/055 081,
  or in the form of surface-stabilized particles dispersed in the liquid fatty phase. The dispersion of surface-stabilized polymer particles may be manufactured as described in document EP-A-749 747. The polymer particles may in particular be surface-stabilized by means of a stabilizer that may be a block polymer, a grafted polymer and/or a random polymer, alone or as a mixture. Dispersions of film-forming polymer in the liquid fatty phase, in the presence of stabilizers, are especially described in documents EP-A-748 746, EP-A-923 928 and EP-A-930 060, the content of which is incorporated by reference into the present patent application.

Advantageously, dispersions of ethylenic polymer particles dispersed in the absence of additional stabilizer at the surface of the said particles are used.

Examples of polymers of NAD type that may be mentioned more particularly include acrylic dispersions in isododecane, for instance Mexomer PAP® (acrylic copolymer as a dispersion in isododecane (25%) with pyrene/isoprene copolymer) sold by the company Chimex.

Preferably, the lipodispersible polymer in the form of a non-aqueous dispersion of polymer particles may be present in the composition in an active material content ranging from 0.01% to 20%, better still from 0.1% to 15%, better still from 0.5% to 12% and even better still from 1% to 10% by weight relative to the total weight of the composition.

(7) Olefin Copolymer Selected from Amorphous Olefin Copolymers and Olefin Copolymers with Controlled and Moderate Crystallization According to one embodiment variant, a cosmetic composition according to the present invention may comprise, as a hydrophobic film-forming polymer, at least one olefin copolymer selected from amorphous olefin copolymers and olefin copolymers with controlled and moderate crystallization.

The expression olefin copolymer for the purposes of the present application is understood to mean any copolymer formed by polymerization of at least one olefin and another additional monomer different from the said olefin.

The olefin may be in particular an ethylenically unsaturated monomer.

By way of example of an olefin, there may be mentioned ethylene hydrocarbon monomers having in particular one or two ethylene unsaturations, having from 2 to 5 carbon atoms, such as ethylene, propylene, butadiene, isoprene.

Amorphous Olefin Copolymer

According to a first embodiment, the olefin copolymer may be an amorphous copolymer formed by polymerization of at least one olefin.

The expression amorphous copolymer is understood to mean a polymer which does not have a crystalline form. The amorphous copolymer is also film-forming, that is to say that it is capable of forming a film during its application to the skin.

The amorphous olefin copolymer may be in particular a diblock, triblock, multiblock, radial, or star-shaped copolymer, or mixtures thereof.

Such amorphous olefin copolymers are described in application US-A-2002/005562 and in U.S. Pat. No. 5,221,534.

Advantageously, the amorphous olefin copolymer is an amorphous styrene and olefin block copolymer. Thus, it is preferable that the amorphous olefin copolymer comprise at least one styrene block.

The amorphous olefin copolymer is preferably hydrogenated in order to reduce the residual ethylene unsaturations after polymerization of the monomers.

In particular, the amorphous olefin copolymer is an optionally hydrogenated copolymer having styrene blocks and having ethylene/$C_3$-$C_4$ alkylene blocks.

As diblock copolymer, preferably hydrogenated, there may be mentioned styrene-ethylene/propylene copolymers, styrene/ethylene-propylene copolymer styrene-ethylene/butadiene copolymers. Diblock polymers are in particular sold under the name Kraton® G1701E by the company Kraton Polymers.

As triblock copolymer, preferably hydrogenated, there may be mentioned styrene-ethylene/propylene-styrene copolymers, styrene-ethylene/butadiene-styrene copolymers, styrene-isoprene-styrene copolymers, styrene-butadiene-styrene copolymers. Triblock polymers are in particular sold under the names Kraton® G1650, Kraton® G1652, Kraton® D1101, Kraton® D1102, Kraton® D1160 by the company Kraton Polymers.

It is also possible to use a mixture of hydrogenated styrene-butylene/ethylene-styrene triblock copolymer and hydrogenated ethylene-propylene-styrene star-shaped polymer, such a mixture being in particular in isododecane. Such mixtures are for example sold by the company PENRECO under the trade names VERSAGEL® M5960 and VERSAGEL® M5670.

Advantageously, a diblock copolymer such as those described above, and in particular a styrene-ethylene/propylene diblock copolymer, is used as amorphous olefin copolymer.

According to a preferred embodiment of the present invention, a composition according to the invention includes at least one film-forming polymer selected from amorphous olefin copolymer selected from the group consisting of a styrene-ethylene/butylene-styrene triblock copolymer, a styrene-ethylene/butylene diblock copolymer, a styrene-ethylene/isoprene-styrene triblock copolymer, a styrene-ethylene/isoprene diblock copolymer, a styrene/ethylene-propylene diblock copolymer, or a mixture thereof.

Olefin Copolymer with Controlled and Moderate Crystallization

According to a second embodiment, the olefin copolymer is an olefin copolymer with controlled and moderate crystallization.

The olefin copolymers with controlled and moderate crystallization used in the composition of the present application may be any olefin copolymer, namely a copolymer containing solely olefin units, having a controlled and moderate crystalline character, that is to say a level of crystallinity at most equal to 50%, preferably ranging from 5 to 40%, and even better ranging from 10 to 35%.

These copolymers are generally elastomers or plastomers and may be synthesized by any known process, in particular by the free radical route, by Ziegler-Natta catalysis or by metallocene catalysis. Such polymers are described in particular in the application EP-A-1 034 776.

A first class of olefin copolymers with controlled and moderate crystallization, which can be used in the cosmetic composition according to the present invention, may be copolymers of linear or branched α-olefin, in particular $C_2$-$C_{16}$, and even better $C_2$-$C_{12}$, α-olefin. Preferably, these copolymers are bi- or terpolymers and most particularly bipolymers.

Among the bipolymers recommended for the cosmetic composition of the present invention, there may be mentioned bipolymers of ethylene and $C_4$-$C_{16}$, preferably $C_4$-$C_{12}$, α-olefin and bipolymers of propylene and $C_4$-$C_{16}$, preferably $C_4$-$C_{12}$, α-olefin. Preferably still, the α-olefin is chosen from 1-butene, 1-pentene, 1-hexene, 1-octene, 1-nonene, 1-decene, 1-undecene, 1-dodecene, 3,5,5-trimethyl-1-hexene, 3-methyl-1-pentene, 4-methyl-1-pentene.

Among these monomers, 1-butene and 1-octene are particularly preferred.

The bipolymers recommended are the elastomers having a level of crystallinity ranging from 10 to 35%.

These bipolymers are preferably synthesized by metallocene catalysis.

Such bipolymers are marketed by the company DOW CHEMICAL under the trade names "AFFINTIY" (plastomers) and by the company Dupont de Nemours under the name "ENGAGE" (elastomers).

Ethylene-butene bipolymers are marketed by the company EXXON under the trade name "EXACT RESINS" and by the company ELENAC under the trade name "LUFLEXEN".

Among the terpolymers, there may be mentioned the terpolymers of ethylene, propylene and $C_4$-$C_{16}$, preferably $C_4$-$C_{12}$, α-olefin.

In these terpolymers, the $C_4$-$C_{16}$ α-olefin contents are as indicated above and the preferred α-olefins are butene, hexene and octene.

The preferred copolymers, described in the application EP-A-1 034 776, may in particular be ethyleneoctene copolymers sold under the reference "Engage 8400" by the company Dupont de Nemours.

A second class of olefin copolymers with controlled and moderate crystallization suitable for the present invention are copolymers of ethylene or propylene and a cycloolefin, in particular bipolymers.

Generally, the cycloolefin content of the copolymers is less than 20 mol %.

Among the cycloolefins which can be used, there may be mentioned cyclobutene, cyclohexene, cyclooctadiene, norbornene, dimethano-octahydronaphthalene (DMON), ethylidene norbornene, vinyl norbornene and 4-vinylcyclohexene.

The recommended copolymers of this class are copolymers of ethylene and norbornene. The norbornene content of these copolymers is generally less than 18 mol % in order to exhibit the crystalline character required and these copolymers are synthesized by metallocene catalysis.

Appropriate ethylene/norbornene copolymers are marketed by the companies MITSUI PETROCHEMICAL or MITSUI-SEKKA under the trade name "APPEL" and by the company HOECHST-CELANESE under the trade name "TOPAS".

Other recommended ethylene/cycloolefin copolymers are the ethylene/cyclobutene and ethylene/cyclohexene bipolymers containing a low cycloolefin content, generally less than 20 mol %.

A third class of olefin copolymers suitable for the present invention consists of copolymers of monoolefin and a monomer with one or more ethylene bonds such as dienes, for example ethylene/butadiene, propylene/butadiene, ethylene/isoprene and propylene/isoprene bipolymers, and ethylene/propylene/diene terpolymers, also obtained by metallocene synthesis.

The proportion of "ethylene" or "diene" units in the copolymer with controlled crystallization is generally in the range from 3 to 20 mol %.

According to a preferred embodiment, the olefin copolymer with controlled and moderate crystallization is chosen from ethylene/octene copolymers and ethylene/norbornene copolymers.

According to a preferred embodiment, the olefin copolymer may be in particular a polymeric gelling agent capable of thickening or of gelling the organic phase of the composition.

Preferably, the olefin copolymer selected from amorphous olefin copolymers and olefin copolymers with controlled and moderate crystallization may be present in the composition in an active material content ranging from 0.01% to 20%, better still from 0.1% to 15%, better still from 0.5% to 12% and even better still from 1% to 10% by weight relative to the total weight of the composition.

(8) Hydrocarbon-Based Resins Having a Number-Average Molecular Weight of Less than or Equal to 10000 g/mol According to one embodiment variant, a cosmetic composition according to the present invention may comprise, as a hydrophobic film-forming polymer, at least one hydrocarbon resin having a number-average molecular weight of less than or equal to 10000 g/mol, especially ranging from 250 to 5000 g/mol, better still less than or equal to 2000 g/mol and especially ranging from 250 to 2000 g/mol.

The number-average molecular weights (Mn) are determined by gel permeation liquid chromatography (THF solvent, calibration curve established with linear polystyrene standards, refractometric detector).

The above hydrocarbon-based resin used in the cosmetic composition according to the present invention is advantageously a tackifying resin. Such resins are described especially in the Handbook of Pressure Sensitive Adhesive, edited by Donatas Satas, 3rd edition, 1989, pp. 609-619.

It is preferable that the above hydrocarbon-based resin be selected from indene hydrocarbon-based resins.

More preferably, the hydrocarbon-based resin is chosen from low molecular weight polymers that may be classified, according to the type of monomer they comprise, as:

indene hydrocarbon-based resins, preferably such as resins derived from the polymerization in major proportion of indene monomer and in minor proportion of a monomer chosen from styrene, methylindene and methylstyrene, and mixtures thereof.

These resins may optionally be hydrogenated. These resins may have a molecular weight ranging from 290 to 1150 g/mol.

Examples of indene resins that may be mentioned include those sold under the reference Escorez 7105 by the company Exxon Chem., Nevchem 100 and Nevex 100 by the company Neville Chem., Norsolene S105 by the company Sartomer, Picco 6100 by the company Hercules and Resinall by the company Resinall Corp., or the hydrogenated indene/methylstyrene/styrene copolymers sold under the name "Regalite" by the company Eastman Chemical, in particular Regalite R1100, Regalite R1090, Regalite R7100, Regalite R1010 Hydrocarbon Resin and Regalite R1125 Hydrocarbon Resin;

aliphatic pentanediene resins such as those derived from the majority polymerization of the 1,3-pentanediene (trans- or cis-piperylene) monomer and of minor monomers chosen from isoprene, butene, 2-methyl-2-butene, pentene and 1,4-pentanediene, and mixtures thereof. These resins may have a molecular weight ranging from 1000 to 2500 g/mol. Such 1,3-pentanediene resins are sold, for example, under the references Piccotac 95 by the company Eastman Chemical, Escorez 1304 by the company Exxon Chemicals, Nevtac 100 by the company Neville Chem. or Wingtack 95 by the company Goodyear;

mixed resins of pentanediene and of indene, which are derived from the polymerization of a mixture of pentanediene and indene monomers such as those described above, for instance the resins sold under the reference Escorez 2101 by the company Exxon Chemicals, Nevpene 9500 by the company Neville Chem., Hercotac 1148 by the company Hercules, Norsolene A 100 by the company Sartomer, and Wingtack 86, Wingtack Extra and Wingtack Plus by the company Goodyear;

diene resins of cyclopentanediene dimers such as those derived from the polymerization of first monomers chosen from indene and styrene, and of second monomers chosen from cyclopentanediene dimers such as dicyclopentadiene, methyldicyclopentanediene and other pentanediene dimers, and mixtures thereof. These resins generally have a molecular weight ranging from 500 to 800 g/mol, for instance those sold under the reference Betaprene BR 100 by the company Arizona Chemical Co., Neville LX-685-125 and Neville LX-1000 by the company Neville Chem., Piccodiene 2215 by the company Hercules, Petro-Rez 200 by the company Lawter or Resinall 760 by the company Resinall Corp.;

diene resins of isoprene dimers such as terpenic resins derived from the polymerization of at least one monomer chosen from α-pinene, β-pinene and limonene, and mixtures thereof. These resins can have a molecular weight ranging from 300 to 2000 g/mol. Such resins are sold, for example, under the names Piccolyte A115 and S125 by Hercules or Zonarez 7100 or Zonatac 105 Lite by Arizona Chem.

Mention may also be made of certain modified resins such as hydrogenated resins, for instance those sold under the name Eastotac C6-C20 Polyolefin by the company Eastman Chemical Co., under the reference Escorez 5300 by the company Exxon Chemicals, or the resins Nevillac Hard or Nevroz sold by the company Neville Chem., the resins Piccofyn A-100, Piccotex 100 or Piccovar AP25 sold by the company Hercules or the resin SP-553 sold by the company Schenectady Chemical Co.

According to one preferred embodiment, the hydrocarbon-based resin is chosen from indene hydrocarbon-based resins, aliphatic pentanediene resins, mixed resins of pentanediene and of indene, diene resins of cyclopentanediene dimers and diene resins of isoprene dimers, or mixtures thereof.

Preferably, the composition comprises at least one compound chosen from hydrocarbon-based resins as described previously, especially indene hydrocarbon-based resins and aliphatic pentanediene resins, or mixtures thereof. According to one preferred embodiment, the hydrocarbon-based resin is chosen from indene hydrocarbon-based resins.

According to one preferred embodiment, the resin is chosen from indene/methylstyrene/hydrogenated styrene copolymers.

In particular, use may be made of indene/methylstyrene/hydrogenated styrene copolymers, such as those sold under the name Regalite by the company Eastman Chemical, such as Regalite R 1100, Regalite R 1090, Regalite R-7100, Regalite R 1010 Hydrocarbon Resin and Regalite R 1125 Hydrocarbon Resin.

Preferably, the hydrocarbon-based resins having a number-average molecular weight of less than or equal to 10000 g/mol may be present in the composition in an active material content ranging from 0.01% to 20%, better still from 0.1% to 15%, better still from 0.5% to 12% and even better still from 1% to 10% by weight relative to the total weight of the composition.

[Pulverulent Phase]

The cosmetic composition according to the present invention includes a pulverulent phase.

A cosmetic composition according to the present invention advantageously has a content of a pulverulent phase of greater than or equal to 40% by weight, preferably from 50% to 75% by weight, and more preferably from 55% to 70% by weight, relative to the total weight of the composition.

It is preferable that the amount of the oil phase (and preferably of the liquid fatty phase) and the amount of the pulverulent phase are such that the weight ratio of the oil phase (and preferably of the liquid fatty phase):the pulverulent phase is ranging from 20:80 to 45:55, preferably 25:75 to 40:60, and more preferably 30:70 to 38:62.

(Filler)

According to the present invention, the pulverulent phase comprises at least one filler.

The term "fillers" should be understood as meaning colourless or white solid particles of any form, which are in a form that is insoluble and dispersed in the medium of the composition. Mineral or organic in nature, they make it possible to confer softness, mattness and uniformity of makeup on the composition.

The fillers used in the cosmetic compositions according to the present invention may be in non-spherical (lamellar or platelet) or spherical (or globular) form, in the form of fibres or in any other intermediate form between these defined forms. Preferably, the cosmetic composition according to the present invention comprises predominantly, or even exclusively, lamellar fillers.

The fillers may be present in a content ranging from 1% to 75% by weight, preferably from 3% to 70% by weight, and more preferentially from 40% to 65% by weight relative to the total weight of the composition.

These fillers according to the present invention may or may not be surface-coated, and in particular they may be surface-treated with silicones, amino acids, fluoro derivatives or any other substance that promotes the dispersion and compatibility of the filler in the cosmetic composition.

Preferably, the pulverulent phase comprises at least one mineral filler. Preferably, this (these) mineral filler(s) are chosen from talc, mica, silica, magnesium aluminium silicate, perlite, trimethyl siloxysilicate, kaolin, bentone, calcium carbonate, magnesium hydrogen carbonate, hydroxyapatite, boron nitride, hollow silica microspheres (Silica Beads from Maprecos), glass or ceramic microcapsules, silica-based fillers, for instance Aerosil 200 or Aerosil 300; Sunsphere H-33 and Sunsphere H-51 sold by Asahi Glass; Chemicelen sold by Asahi Chemical; composites of silica and of titanium dioxide, for instance the TSG series sold by Nippon Sheet Glass, and fluorphlogopite, and mixtures thereof.

The pulverulent phase may comprise at least one organic filler. Preferably, this (these) mineral/organic filler(s) are chosen from polyamide powders (Nylon® Orgasol from Atochem), poly-β-alanine powders and polyethylene powders, polytetrafluoroethylene powders (Teflon®), lauroyllysine, starch, tetrafluoroethylene polymer powders, hollow polymer microspheres, for example comprising an (alkyl) acrylate, such as Expancel® (Nobel Industrie), metal soaps derived from organic carboxylic acids containing from 8 to 22 carbon atoms and preferably from 12 to 18 carbon atoms, for example zinc stearate, magnesium stearate, lithium stearate, zinc laurate, magnesium myristate, Polypore® L200 (Chemdal Corporation), silicone resin microbeads (for example Tospearl® from Toshiba), polyurethane powders, in particular powders of crosslinked polyurethane comprising a copolymer, the said copolymer comprising trimethylol hexyl lactone, for instance the hexamethylene diisocyanate/trimethylol hexyl lactone polymer sold under the name Plastic Powder D-400® or Plastic Powder D-800® by the company Toshiki, carnauba microwaxes, such as the product sold under the name Micro Care 350® by the company Micro Powders, synthetic microwaxes, such as the product sold under the name MicroEase 114S® by the company Micro Powders, microwaxes formed from a mixture of carnauba wax and polyethylene wax, such as those sold under the names Micro Care 300® and 310® by the company Micro Powders, microwaxes formed from a mixture of carnauba wax and of synthetic wax, such as the product sold under the name Micro Care 325® by the company Micro Powders, polyethylene microwaxes, such as those sold under the names Micropoly 200®, 220®, 220L® and 250S® by the company Micro Powders; fibres of synthetic or natural, mineral or organic origin. They may be short or long, individual or organized, for example braided, and hollow or solid. They may have any shape and may especially have a circular or polygonal (square, hexagonal or octagonal) cross section depending on the specific application envisaged. In particular, their ends are blunted and/or polished to prevent injury. The fibres have a length ranging from 1 µm to 10 mm, preferably from 0.1 mm to 5 mm and better still from 0.3 mm to 3 mm. Their cross section may be included in a circle with a diameter ranging from 2 nm to 500 µm, preferably ranging from 100 nm to 100 µm and better still from 1 µm to 50 µm. As fibres that can be used in the cosmetic composition according to the present invention, mention may be made of non-rigid fibres such as polyamide (Nylon®) fibres or rigid fibres such as polyimideamide fibres, for instance those sold under the names Kermel® and Kennel Tech® by the company Rhodia or poly(p-phenyleneterephthalamide) (or aramid) fibres sold especially under the name Kevlar® by the company DuPont de Nemours, and mixtures thereof.

It is more preferable that the pulverulent phase comprises at least one non-spherical filler preferably selected from the group consisting of talc, mica, silica, kaolin, sericite, calcinated talc, calcinated mica, calcinated sericite, synthetic mica, lauroyl lysine, metal soap, bismuth oxychloride, barium sulfate, boron nitride, calcium carbonate, magnesium carbonate, magnesium hydrogen carbonate, hydroxyapatite, and a mixture thereof.

The pulverulent phase may preferably comprise at least one spherical filler preferably selected from the group consisting of organic filler and silica, preferably selected from the group consisting of polyurethane powder, polyamide powder and silica.

(Coloring Agent)

The pulverulent phase advantageously also comprise at least one colouring agent. The total amount of coloring agent(s) is preferably greater than 5% by weight compared to the total weight of the composition, advantageously going from 6% to 70% by weight compared to the total weight of the composition.

The colouring agent(s) or dyestuff(s) according to the present invention are preferably chosen from pigments, nacres and reflective particles, and mixtures thereof. Preferably, the pulverulent phase comprises at least one pigment.

The term "pigments" should be understood as meaning white or coloured, mineral or organic particles of any shape, which are insoluble in the physiological medium, and which are intended to colour the composition.

The pigments may be white or coloured, and mineral and/or organic.

Among the mineral pigments that may be mentioned are titanium dioxide, optionally surface-treated, zirconium oxide or cerium oxide, and also zinc oxide, iron (black, yellow or red) oxide or chromium oxide, manganese violet, ultramarine blue, chromium hydrate and ferric blue, and metal powders, for instance aluminium powder and copper powder.

The organic pigments may be chosen from the materials below, and mixtures thereof cochineal carmine; and organic pigments of azo dyes, anthraquinone dyes, indigoid dyes, xanthene dyes, pyrene dyes, quinoline dyes, triphenylmethane dyes and fluoran dyes.

Among the organic pigments, mention may be made especially of the D&C certified pigments known under the following names: D&C Blue No. 4, D&C Brown No. 1, D&C Green No. 5, D&C Green No. 6, D&C Orange No. 4, D&C Orange No. 5, D&C Orange No. 10, D&C Orange No. 11, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, D&C Violet No. 2, D&C Yellow No. 7, D&C Yellow No. 8, D&C Yellow No. 10, D&C Yellow No. 11, FD&C Blue No. 1, FD&C Green No. 3, FD&C Red No. 40, FD&C Yellow No. 5, FD&C Yellow No. 6.

The chemical materials corresponding to each of the organic dyestuffs mentioned previously are mentioned in the publication "International Cosmetic Ingredient Dictionary and Handbook", 1997 edition, pages 371 to 386 and 524 to 528, published by The Cosmetic, Toiletries and Fragrance Association, the content of which is incorporated into the present patent application by reference.

The pulverulent phase may comprise a content of pigments ranging from 0 to 75% by weight relative to the total weight of the composition, preferably ranging from 2% to 70% by weight and preferentially ranging from 10% to 65% by weight, relative to the total weight of the composition.

The colouring agents may be pearlescent agents or nacres.

The terms "pearlescent pigments" or "nacres" should be understood as meaning coloured particles of any form, which may or may not be iridescent, especially produced by certain molluscs in their shell, or alternatively synthesized, and which have a colour effect via optical interference.

Examples of nacres that may be mentioned include nacreous pigments such as titanium mica coated with an iron oxide, mica coated with bismuth oxychloride, titanium mica coated with chromium oxide, and nacreous pigments based on bismuth oxychloride. They may also be mica particles at the surface of which are superposed at least two successive layers of metal oxides and/or of organic dyestuffs.

The nacres may more particularly have a yellow, pink, red, bronze, orange, brown, gold and/or coppery colour or glint.

As illustrations of nacres that may be introduced into the composition, mention may be made of the gold-coloured nacres sold especially by the company Engelhard under the name Brilliant gold 212G (Timica), Gold 222C (Cloisonne), Sparkle gold (Timica), Gold 4504 (Chromalite) and Monarch gold 233X (Cloisonne); the bronze nacres sold especially by the company Merck under the name Bronze fine (17384) (Colorona) and Bronze (17353) (Colorona) and by the company Engelhard under the name Super bronze (Cloisonne); the orange nacres sold especially by the company Engelhard under the name Orange 363C (Cloisonne) and Orange MCR 101 (Cosmica) and by the company Merck under the name Passion orange (Colorona) and Matte orange (17449) (Microna); the brown nacres sold especially by the company Engelhard under the name Nu-antique copper 340XB (Cloisonne) and Brown CL4509 (Chromalite); the nacres with a copper tint sold especially by the company Engelhard under the name Copper 340A (Timica); the nacres with a red tint sold especially by the company Merck under the name Sienna fine (17386) (Colorona); the nacres with a yellow tint sold especially by the company Engelhard under the name Yellow (4502) (Chromalite); the red nacres with a gold tint sold especially by the company Engelhard under the name Sunstone G012 (Gemtone); the pink nacres sold especially by the company Engelhard under the name Tan opale G005 (Gemtone); the black nacres with a gold tint sold especially by the company Engelhard under the name Nu antique bronze 240 AB (Timica), the blue nacres sold especially by the company Merck under the name Matte blue (17433) (Microna), the white nacres with a silvery tint sold especially by the company Merck under the name Xirona Silver, and the golden-green pink-orange nacres sold especially by the company Merck under the name Indian summer (Xirona), and mixtures thereof.

Still as examples of nacres, mention may also be made of particles comprising a borosilicate substrate coated with titanium oxide.

Particles having a glass substrate coated with titanium oxide are especially sold under the name Metashine MC1080RY by the company Toyal.

Finally, examples of nacres that may also be mentioned include polyethylene terephthalate flakes, especially those sold by the company Meadowbrook Inventions under the name Silver 1P 0.004×0.004 (silver flakes).

The pulverulent phase may have a nacre content ranging from 0 to 75% by weight, for example from 2% to 70% by weight, from 10% to 65% by weight, relative to the total weight of the composition.

The colouring agents may be reflective particles.

The term "reflective particles" denotes particles whose size, structure, especially the thickness of the layer(s) of which they are made and their physical and chemical nature, and surface state, allow them to reflect incident light. This reflection may, where appropriate, have an intensity sufficient to create at the surface of the composition or of the mixture, when it is applied to the support to be made up, points of overbrightness that are visible to the naked eye, i.e. more luminous points that contrast with their environment by appearing to sparkle.

The reflective particles may be selected so as not to significantly alter the colouration effect generated by the colouring agents with which they are combined, and more particularly so as to optimize this effect in terms of colour yield. They may more particularly have a yellow, pink, red, bronze, orange, brown, gold and/or coppery colour or tint.

These particles may have varied forms and may especially be in platelet or globular form, in particular in spherical form.

The reflective particles, whatever their form, may or may not have a multilayer structure and, in the case of a multilayer structure, may have, for example, at least one layer of uniform thickness, in particular of a reflective material.

When the reflective particles do not have a multilayer structure, they may be composed, for example, of metal oxides, especially titanium or iron oxides obtained synthetically.

When the reflective particles have a multilayer structure, they may comprise, for example, a natural or synthetic substrate, especially a synthetic substrate at least partially coated with at least one layer of a reflective material, especially of at least one metal or metallic material. The substrate may be made of one or more organic and/or inorganic materials.

More particularly, it may be chosen from glasses, ceramics, graphite, metal oxides, aluminas, silicas silicates, especially aluminosilicates and borosilicates, and synthetic mica, and mixtures thereof this list not being limiting.

The reflective material may comprise a layer of metal or of a metallic material.

Reflective particles are described especially in documents JP-A-09188830, JP-A-10158450, JP-A-10158541, JP-A-07258460 and JP-A-05017710.

Again as an example of reflective particles comprising a mineral substrate coated with a layer of metal, mention may also be made of particles comprising a silver-coated borosilicate substrate.

Particles with a silver-coated glass substrate, in the form of platelets, are sold under the name Microglass Metashine REFSX 2025 PS by the company Toyal. Particles with a glass substrate coated with nickel/chromium/molybdenum alloy are sold under the name Crystal Star GF 550 and GF 2525 by this same company.

Use may also be made of particles comprising a metallic substrate such as silver aluminium, iron, chromium, nickel, molybdenum, gold, copper, zinc, tin, manganese, steel, bronze or titanium, said substrate being coated with at least one layer of at least one metal oxide such as titanium oxide, aluminium oxide, iron oxide, cerium oxide, chromium oxide or silicon oxides, and mixtures thereof.

Examples that may be mentioned include aluminium powder, bronze powder or copper powder coated with $SiO_2$ sold under the name Visionaire by the company Eckart.

The pulverulent phase may have a content of reflective particles ranging from 0 to 30% by weight, for example from 0.01% to 5% by weight, relative to the total weight of the composition.

Preferably, the pulverulent phase comprises at least one compound chosen from:
- at least one non-spherical filler; preferably at least one inorganic filler, advantageously chosen from talc, mica, perlite, metal soap and a mixture thereof;
- at least one spherical filler, preferably silica and organic fillers advantageously chosen from polyurethane powders polyamide powders; and
- at least one coloring agent selected from inorganic pigments advantageously chosen from iron oxide, titanium oxide, zirconium oxide, cerium oxide, zinc oxide or chromium oxide, ferric blue, manganese violet, ultramarine blue, pink or violet, chromium hydrate, chromium hydroxide and bismuth oxychloride, and mixtures thereof, from pearlescent pigments, from nacres, and their mixture.

[Aqueous Phase]

The cosmetic composition according to the present invention may comprise an aqueous phase.

This aqueous phase, when present, is used in an amount that is compatible with the pulverulent galenical form required according to the present invention.

The aqueous phase may be a demineralized water or alternatively a floral water such as cornflower water and/or a mineral water such as Vittel water, Lucas water or La Roche Posay water and/or a spring water.

The aqueous phase may also comprise a polyol that is miscible with water at room temperature (25° C.) chosen especially from polyols especially containing from 2 to 20 carbon atoms, preferably containing from 2 to 10 carbon atoms and preferentially containing from 2 to 6 carbon atoms, such as glycerol, propylene glycol, butylene glycol, pentylene glycol, hexylene glycol, dipropylene glycol or diethylene glycol; glycol ethers (especially containing from 3 to 16 carbon atoms) such as mono-, di- or tripropylene glycol ($C_1$-$C_4$)alkyl ethers, mono-, di- or triethylene glycol ($C_1$-$C_4$)alkyl ethers; and mixtures thereof.

The cosmetic composition according to the present invention may comprise a polyol that is miscible with water at room temperature. Such polyols may promote the moisturization of the surface of the skin on which the composition is applied.

In addition, the cosmetic composition according to the present invention may comprise a monoalcohol containing from 2 to 6 carbon atoms, such as ethanol or isopropanol.

A cosmetic composition according to the present invention advantageously comprises less than 5% by weight, preferably 3% by weight, more preferably 2% by weight of aqueous phase, and in particular of water, relative to the total weight of the composition. Preferentially, a cosmetic composition according to the present invention is free of aqueous phase, and in particular free of water.

[Adjuvants]

The composition may comprise other ingredients (adjuvants) usually used in cosmetics, such as antioxidants, fragrances, preservatives, neutralizing agents, surfactants, waxes, sunscreens, vitamins, moisturizing agents, self-tanning compounds or antiwrinkle active principles.

Needless to say, a person skilled in the art will take care to select the optional adjuvant(s) added to the cosmetic composition according to the present invention such that the advantageous properties intrinsically associated with the cosmetic composition in accordance with the present invention are not, or are not substantially, adversely affected by the envisaged addition.

[Wet Process]

The cosmetic composition according to the present invention is obtained by a wet process comprising the steps of: mixing the oil phase, the film-forming polymer(s), the pulverulent phase, and at least one additional solvent to prepare a slurry; and
shaping the slurry in a container by compression and/or aspiration to prepare the cosmetic composition.

The oil phase and the film-forming polymer(s) form a fatty phase and preferably a liquid fatty phase.

The employed wet process includes the steps of mixing the components of the fatty phase and the pulverulent phase, as well as one or more additional solvents to obtain a slurry; and shaping the slurry in a container by compression or aspiration. It is preferable that the wet process include the step of drying the shaped slurry. The details of each step will be explained below.

It should be noted that so-called semi-wet process, in which only a small amount of additional solvent(s) is used and a slurry is not prepared, does not correspond to the wet-process. In the semi-wet process, the solvent may not be removed. Furthermore, another process in which a slurry is prepared but dried before being pressed, and the dried matter is broken to be pressed does not correspond to the wet process either.

(Mixing Step)

In this step, the components of the fatty phase and the pulverulent phase as well as one or more additional solvents are mixed to prepare a slurry. The slurry here means a thick suspension of powder-based materials in the solvent.

According to one embodiment, in the mixing step, the components in the fatty phase and the pulverulent phase are mixed to form a mixture, and one or more additional solvents are further mixed with the mixture.

According to another embodiment, in the mixing step, the components in the fatty phase are mixed with one or more additional solvents to form a mixture, and the components of the pulverulent phase are further mixed with the mixture.

It is preferable that the amount of the liquid fatty phase and the amount of the pulverulent phase are such that the weight ratio of the oil phase (and preferably the liquid fatty phase):the pulverulent phase is ranging from 20:80 to 45:55, preferably 25:75 to 40:60, and more preferably 30:70 to 38:62.

It is preferable that one or more additional solvents are selected from volatile solvents. As the volatile solvent, mention may be made of water, lower alcohols such as ethanol and isopropanol, ethers, fluorocarbons, volatile silicones such as low molecular weight cyclic or linear silicones, and hydrocarbons such as light liquid isoparaffin. In terms of usability, volatile organic solvents such as isopropanol and light liquid isoparaffin are preferable. Light liquid isoparaffin is most preferable. The above volatile solvent may be use alone or in combination.

According to one embodiment of the present invention, the mixing with the pulverulent phase may be performed in any mixer such as a Henschel mixer. Preferably, the mixed powdery product may be subjected to milling by, for example, a hammer mill.

According to another embodiment, the mixing with the additional solvent(s) may be performed in an appropriate vessel such as a bowl. This may be performed in a planetary mixer. The time required for dispersing is not limited, and may depend on some factors such as the type of a mixer. For example, if a planetary mixer is used for dispersing, from about 15 minutes to about 20 minutes may be necessary.

The amounts of a sum of the fatty phase and the pulverulent phase and the additional solvent(s) are not limited. The ratio of the amount of the additional solvent(s) to that of the sum of the liquid fatty phase and the pulverulent phase may be determined in terms of usability. If the amount of the additional solvent(s) is too high, the obtained slurry may overflow or drip off from a container in the next shaping step, or may shrink too much after the last drying step. On the other hand, if the amount of the additional solvent(s) is too low, the obtained slurry may not easily be shaped in the next shaping step, or may have cracks after the last drying step. For example, the sum of the liquid fatty phase and the pulverulent phase and the additional solvent(s) may be used in a weight ratio of 5:1, preferably 3:1, and more preferably 2:1.

If necessary, degassing may be performed during the mixing step. The degassing can be performed, for example, by mixing the liquid fatty phase and/or the pulverulent phase in the additional solvent(s) in a vacuum chamber. The time required for degassing is not limited, and may depend on some factors such as the pressure in the vacuum chamber. For example, degassing may be performed from about 15 minutes to about 20 minutes. It is preferable to stir the slurry for efficient degassing.

(Shaping Step)

In this step, the slurry is shaped in a container by compression or aspiration. For example, the slurry obtained by the previous mixing step is poured into a container, and the slurry is pressed and/or aspirated to give a shape to the slurry.

As the container, any vessel such as a dish or a pan can be used. Preferably, a pan may be used as the container. The container may have small holes through which the components of the cosmetic cannot move but a solvent can move for aspiration of the solvent.

The mode of pouring the slurry into a container is not limited. Typically, there are two modes, i.e., top injection and back injection.

According to the top injection, the slurry is poured into a container from the top of the container. The top injection is preferable to prepare a cosmetic product having a plurality of colors. Further, the top injection is more cost effective as compared to the back injection, because the container does not need to have a complicated mechanism for injection of the slurry.

According to the back injection, the slurry is poured into a container from the bottom of the container. For the injection, the bottom of the container typically needs to have a mechanism for supplying the slurry into the container. The back injection is preferable to prepare a cosmetic product with a large scale. Further, the back injection can easily prepare a cosmetic product with a complicated shape. The slurry introduced into a container is shaped by compression and/or aspiration. Preferably, the press and aspiration are performed simultaneously.

The compression may be performed by pressing the slurry in a container by a mechanical means such as a press member having a plane surface. The aspiration may be performed, for example, by reducing the pressure in the container by vacuuming. The compression and aspiration may be performed several times. If necessary, vibration may be given to the container and/or the press member. It is preferable that at least a part of the additional solvent(s) in the slurry is removed by the compression and the aspiration to solidify the slurry. It is more preferable that a large part of the additional solvent(s) is removed from the slurry.

(Drying Step)

In this step, the shaped slurry can be dried to obtain a cosmetic composition without the additional solvent(s). By drying, the additional solvent remaining in the slurry can be completely removed. The temperature for drying depends on several factors such as the components in the cosmetic composition and the type of the used additional solvent. For example, the drying may be performed at from about 60° to 100°. The time required for drying also depends on the above factors. For example, the drying is performed for about 1 to 12 hours.

[Cosmetic Process]

According to another aspect of the present invention, a subject of the present invention is also processes for a cosmetic process including a step of applying to skin, preferably face or eyelid, a cosmetic composition according to the present invention.

The cosmetic process preferably includes making up and/or caring for the skin, preferably facial skin and eyelid skin. Preferably, the cosmetic composition according to the present invention can be a powdery foundation, a pressed powder, a blusher, a bronzer, an eye shadow.

The cosmetic composition used in the cosmetic process according to the present invention is preferably of the leave-in type. The term "leave-in" means a composition that is not intended to be washed out or removed immediately after application.

Since the cosmetic composition according to the present invention is obtained by a wet process, the texture of the cosmetic film on the skin is smooth and uniform, and the cosmetic film has good staying power on the skin over time and good maintenance of matt effects over time.

Furthermore, the cosmetic composition according to the present invention can have wet feeling, good spreadability and the like.

The cosmetic composition according to the present invention can be resistant to impacts, and may not be easy to collapse or erode. Thus, it is preferable that the cosmetic composition according to the present invention is in the form of a compact powder.

The term "compact powder" means a mass of product whose cohesion is at least partly provided by compacting during the manufacture. In particular, by taking a measurement using a TA.XT.plus Texture Analyser texturometer sold by the company Stable Micro Systems, the cosmetic composition in the form of a compact powder according to the present invention may advantageously have a pressure resistance of between 0.1 and 1 kg and especially between 0.2 and 0.8 kg, relative to the surface area of the spindle used (in the present case 7.07 mm$^2$). The measurement of this resistance is performed by moving an SMS P/3 flat-ended cylindrical cylinder in contact with the powder over a distance of 2 mm at a speed of 0.5 mm/second; more generally, this powder is obtained by compacting. The term "compact powder" should be understood more precisely to mean that these powders have a shore A hardness, measured using a Zwick durometer, which ranges, according to the intensity of the shades under consideration, from 12 to 30° Shore A.

The cosmetic composition according to the present invention is in the form of a solid composition.

The term "solid" means the state of the composition at room temperature (25° C.) and at atmospheric pressure (760 mmHg), i.e. a composition of high consistency, which conserves its form during storage. As opposed to "fluid" compositions, it does not flow under its own weight. It is advantageously characterized by a hardness as defined below.

The cosmetic composition according to the present invention advantageously comprises a solids content of greater than or equal to 95%, better still 98%, or even equal to 100%.

For the purposes of the present invention, the "solids content" denotes the content of non-volatile matter.

The solids content (abbreviated as SC) of a cosmetic composition according to the present invention is measured using a "Halogen Moisture Analyzer HR 73" commercial halogen desiccator from Mettler Toledo. The measurement is performed on the basis of the weight loss of a sample died by halogen heating, and thus represents the percentage of residual matter once the water and the volatile matter have evaporated off.

This technique is fully described in the machine documentation supplied by Mettler Toledo.

The measuring protocol is as follows.

Approximately 2 g of the composition, referred to hereinbelow as the sample, are spread out on a metal crucible, which is placed in the halogen desiccator mentioned above. The sample is then subjected to a temperature of 105° C. until a constant weight is obtained. The wet mass of the sample, corresponding to its initial mass, and the dry mass of the sample, corresponding to its mass after halogen heating, are measured using a precision balance.

The experimental error associated with the measurement is of the order of plus or minus 2%.

The solids content is calculated in the following manner:

Solids content(expressed as weight percentage)=
100×(dry mass/wet mass).

EXAMPLES

The present invention will be described in more detail by way of examples, which however should not be construed as limiting the scope of the present invention.

Examples 1-6 and Comparative Example 1

[Preparations]

The following compositions according to Examples 1-6 and Comparative Example 1, shown in Table 1, were prepared by mixing the components shown in Table 1 in accordance with the wet process shown below to form a powder foundation. The numerical values for the amounts of the components shown in Table 1 are all based on "% by weight" as active raw materials.

For example 2 in the table here-below:

Example a: Preparation of a Poly(Isobornyl Acrylate/Isobornyl Methacrylate/Isobutyl Acrylate/Acrylic Acid) Copolymer 300 g of isododecane are introduced into a 1 litre reactor and then the temperature is increased so as to change from ambient temperature (25° C.) to 90° C. in 1 hour.

105 g of isobornyl methacrylate, 105 g of isobornyl acrylate and 1.8 g of 2,5-bis(2-ethylhexanoylperoxy)-2,5-dimethylhexane (Trigonox® 141 from Akzo Nobel) are subsequently added at 90° C. in 1 hour.

The mixture is maintained at 90° C. for 1 h 30.

75 g of isobutylacrylate, 15 g of acrylic acid and 1.2 g of 2,5-bis(2-ethylhexanoylperoxy)-2,5-dimethylhexane are subsequently introduced into the preceding mixture, still at 90° C. and in 30 minutes.

The mixture is maintained at 90° C. for 3 hours and then the combined product is cooled.

A solution is thus obtained comprising 50% of copolymer dry matter in 50% of isododecane, the copolymer comprising a first poly(isobornyl acrylate/isobornyl methacrylate) block or sequence having a Tg of 128° C., a second poly(isobutyl acrylate/acrylic acid) block having a Tg of −9° C. and an intermediate block which is an isobornyl acrylate/isobornyl methacrylate/isobutyl acrylate/acrylic acid random copolymer.

The Tg of the copolymer is 74° C.

These are theoretical Tg values calculated by the Fox law.

Example b: Distillation of the Synthesis Solvent (the Isododecane) with Addition of Octyldodecyl Neopentanoate The solution obtained in Example 1 is heated at 130° C. under a vacuum of 100 mbar in order to evaporate the isododecane, while simultaneously adding octyldodecyl neopentanoate. The whole of the isododecane is replaced by as much octyldodecyl neopentanoate by weight.

The use of octyldodecyl neopentanoate makes it possible to evaporate all of the isododecane, the latter possibly remaining only in the form of residual traces. A solution comprising 50% of copolymer dry matter in 50% of octyldodecyl neopentanoate is thus obtained.

TABLE 1

|   |   | Ex. 1 | Ex. 2 | Ex. 3 | Ex. 4 | Ex. 5 | Ex. 6 | Comp Ex. 1 |
|---|---|---|---|---|---|---|---|---|
| P | Mica | 50.66 | 50.66 | 50.66 | 50.66 | 50.66 | 50.66 | 50.66 |
|   | Talc | 4.30 | 4.30 | 4.30 | 4.30 | 4.30 | 4.30 | 4.30 |
|   | Pigments | 10.04 | 10.04 | 10.04 | 10.04 | 10.04 | 10.04 | 10.04 |
|   |   | 65 | 65 | 65 | 65 | 65 | 65 | 65 |
| F1 | Styrene/isoprene block copolymer KRATON G1701 EU | 1.5 | — | — | — | — | — | — |
|   | Hydrogenated styrene/methylstyrene/indene copolymer REGALITE R1100 CG | 3 | — | — | — | — | — | — |
|   | Poly(isobornyl meth-acrylate-co-isobornyl acrylate-co-isobutyl acrylate-co-acrylic acid) at 50% of active material in 50% of octyldodecyl neopentanoate, according to Example of preparation a) and b) above CHIMEX MEXOMERE PAZ | — | 8 | — | — | — | — | — |
|   | Polymethylsilsesquioxane SILFORM FLEXIBLE RESIN | — | — | 10 | — | — | — | — |
|   | Polypropylsilsesquixane at 72% of active material in 28% of isododecane DOW CORNING 680 ID FLUID | — | — | — | 10 | — | — | — |
|   | Nylon-611/dimethicone copolymer DOW CORNING 2-8179 GELLANT | — | — | — | — | 1.5 | — | — |
|   | Acrylates/polytrimethylsiloxymethacrylate copolymer DOW CORNING FA 4002 ID SILICONE ACRYLATE | — | — | — | — | — | 5 | — |
| F2 | Isononyl isononanoate WICKENOL 151 | 25 | 21.5 | 19.5 | 19.5 | 28 | 24.5 | 29.5 |
|   | Dimethicone XIAMETER PMX-200 SILICONE FLUID 10 cSt | 5 | 5 | 5 | 5 | 5 | 5 | 5 |
|   | Preservative system | 0.5 | 0.5 | 0.5 | 0.5 | 0.5 | 0.5 | 0.5 |
|   |   | 35 | 35 | 35 | 35 | 35 | 35 | 35 |
|   |   | 100 | 100 | 100 | 100 | 100 | 100 | 100 |

P: Pulverulent phase
F1: Film-forming polymer and the like,
F2: Oil phase and Preservative (Wet Process)

The components in the pulverulent phase (P) were mixed in a mixer. The components in the film-forming polymer and the like (F1), the oil phase and the preservative (F2), which form together a liquid fatty phase, were heated and mixed in a separate mixer. Both mixtures were mixed together to prepare a bulk mixture.

100 parts by weight of the above bulk mixture was mixed with from 35 to 55 parts by weight of hydrogenated polyisobutene as an additional solvent, depending on the type of the components, to form a slurry. The slurry was charged in to a pan, followed by being pressed at a pressure of 100 kgf/cm$^2$, aspirated and dried to form a powder foundation in the form of a compressed powder.

[Evaluations]
(Sensory Evaluation)

The powder foundations according to Examples 1-3 and Comparative Example 1 were compared in terms of skin adhesion by panelists under the conditions that the powder foundation of any of Examples 1-3 was applied onto the half of the face of each panelist, and the powder foundation of Comparative Example 1 was applied to the other half of the face of each panelist, wherein the amount of the powder foundation applied to the each half of the face was the same. All of the panelist reported that the powder foundations according to Examples 1-3 had better adhesion onto the skin than the powder foundation according to Comparative Example 1.

The powder foundations according to Examples 4-6 are also evaluated as above, and all the panelist reports that the powder foundations according to Examples 4-6 have better adhesion onto the skin than the powder foundation according to Comparative Example 1.

(Matte Evaluation)

The powder foundations according to Examples 1-2 and Comparative Example 1 were compared in terms of gloss intensity by panelists under the conditions that the powder foundations of Examples 1-2 and Comparative Example 1 were applied to the face of each panelist Next, the gloss (reflected light on the face) of the face was measured by a polarimetric camera immediately after the application (T0) and 3 hours later the application (T3). The difference in the gloss between T0 and T3 was determined as a matte value, and compared under the condition that the difference in the gloss for the powder foundation according to Comparative Example 1 is set as 1. The results are shown in Table 2.

TABLE 2

|   | Ex. 1 | Ex. 2 | Comp. Ex. 1 |
|---|---|---|---|
| Matte (T3-T0) | 0.72 | 0.48 | 1 |

The lower the matte value was, the longer the cosmic effect lasts. The results shown in Table 2 show that the powder foundations according to Examples 1 and 2 provided cosmetic effects longer than that according to Comparative Example 1.

The powder foundations according to Examples 3-6 are also evaluated as above, and it is found that the matte values of the powder foundations according to Examples 3-6 are smaller than that of the powder foundation according to Comparative Example 1, and therefore, the powder foundations according to Examples 3-6 provide cosmetic effects longer than that according to Comparative Example 1.

Examples 7-12

[Preparations]

The following compositions according to Examples 7-12, shown in Table 3, are prepared by mixing the components shown in Table 3 in accordance with the wet process shown below to form a powder foundation. The numerical values for the amounts of the components shown in Table 3 are all based on "% by weight" as active raw materials.

[Evaluations]
(Sensory Evaluation)

The powder foundations according to Examples 7-12 are compared in terms of skin adhesion by panelists under the conditions that the powder foundation of any of Examples 7-12 is applied onto the half of the face of each panelist, and the powder foundation of Comparative Example 1 is applied to the other half of the face of each panelist, wherein the amount of the powder foundation applied to each half of the face was the same. All of the panelist report that the powder foundations according to Examples 7-12 have better adhesion onto the skin than the powder foundation according to Comparative Example 1.

TABLE 3

| | | Ex. 7 | Ex. 8 | Ex. 9 | Ex. 10 | Ex. 11 | Ex. 12 |
|---|---|---|---|---|---|---|---|
| P | Mica | 50.66 | 50.66 | 50.66 | 39.66 | 39.66 | 50.66 |
| | Zea mays (corn) starch | — | — | — | 5 | 5 | — |
| | HDI/Trimethylol hexyllactone crosspolymer PLASTIC POWDER D400 | — | — | — | 6 | 6 | — |
| | Talc | 4.30 | 4.30 | 4.30 | 4.30 | 4.30 | 4.30 |
| | Pigments (Iron oxides) | 10.04 | 10.04 | 10.04 | 10.04 | 10.04 | 10.04 |
| | | 65 | 65 | 65 | 65 | 65 | 65 |
| F1 | Acrylates/stearyl acrylate/dimethicone methacrylate copolymer SHINETSU KP 561 P | 1 | — | — | — | — | — |
| | Trimethylsiloxysilicate MOMENTIVE SR 1000 | — | 10 | — | — | — | — |
| | styrene/isoprene block copolymer KRATON G1701 EU | — | — | 2 | — | — | — |
| | styrene/butadiene block copolymer KRATON G1657M | — | — | — | 1 | — | — |
| | Hydrogenated styrene/methyl styrene/indene copolymer REGALITE R1100 CG | — | — | — | — | 1 | — |
| | Mixture of Acrylates copolymer and Hydrogenated styrene/isoprene copolymer respectively at 21.3% and 3.2% of active material in 75.5% of Isododecane CHIMEX MEXOMERE PAP | — | — | — | — | — | 5 |
| F2 | Isononyl isononanoate WICKENOL 151 | 28.5 | — | 27.5 | — | — | 24.5 |
| | Hydrogenated polyisobutene PARLEAM FROM NOF CORP. | — | 19.5 | — | 23.5 | 23.5 | — |
| | Dimethicone XIAMETER PMX-200 SILICONE FLUID 10 cSt | 5 | 5 | 5 | — | — | 5 |
| | Phenyltrimethicone SHINETSU KF-56A | — | — | — | 10 | 10 | — |
| | Preservative system | 0.5 | 0.5 | 0.5 | 0.5 | 0.5 | 0.5 |
| | | 35 | 35 | 35 | 35 | 35 | 35 |
| | | 100 | 100 | 100 | 100 | 100 | 100 |

P: Pulverulent phase
F1: Film-forming polymer and the like,
F2: Oil phase and Preservative (Wet Process)

The components in the pulverulent phase (P) are mixed in a mixer. The components in the film-forming polymer and the like (F1), the oil(s) and the preservative (F2), which form a liquid fatty phase, are heated and mixed in a separate mixer. Both mixtures are mixed together to prepare a bulk mixture.

100 parts by weight of the above bulk mixture is mixed with from 35 to 55 parts by weight of hydrogenated polyisobutene as an additional solvent, depending on the type of the components, to form a slurry. The slurry is charged in to a pan, followed by being pressed at a pressure of 20 kgf/cm², aspirated and dried to form a powder foundation in the form of a compressed powder.

(Matte Evaluation)

The powder foundations according to Examples 7-12 and Comparative Example 1 are compared in terms of gloss intensity by panelists under the conditions that the powder foundations of Examples 7-12 and Comparative Example 1 are applied to the face of each panelist.

Next, the gloss (reflected light on the face) of the face is measured by a polarimetric camera immediately after the application (T0) and 3 hours after the application (T3). The difference in the gloss between T0 and T3 is determined as a matte value, and compared under the condition that the difference in the gloss for the powder foundation according to Comparative Example 1 is set as 1.

It is found that the matte values of the powder foundations according to Examples 7-12 are smaller than that of the powder foundation according to Comparative Example 1, and therefore, the powder foundations according to Examples 7-12 provide cosmetic effects longer than that according to Comparative Example 1.

Example 13 and Comparative Example 2

[Preparations]

The following eye-shadow compositions, shown in Table 4, were prepared by mixing the components in accordance with a wet process (Example 13) and comparatively in accordance with a dry process (example 2). The numerical values for the amounts of the components shown in Table 4 are all based on "% by weight" as active raw materials.

TABLE 4

|   |   | Ex. 13 | Comp. Ex. 2 |
|---|---|---|---|
| P | HDI/Trimethylol hexyllactone crosspolymer PLASTIC POWDER D400 | 2.64 | 2.64 |
|   | Mica | 1.65 | 1.65 |
|   | Nacres (Mica coated with titanium oxide) | 61.71 | 61.71 |
|   |   | 66 | 66 |
| F1 | styrene/butadiene block copolymer KRATON G1657M | 3.35 | 3.35 |
| F2 | $C_{12-15}$ alkyl benzoate TEGGOSOFT TN FROM EVONIK GOLDSCHMIDT | 20.1 | 20.1 |
|   | Phenyl trimethicone DOW CORNING 556 COSMETIC GRADE FLUID | 10.05 | 10.05 |
|   | Preservative system | 0.5 | 0.5 |
|   |   | 34 | 34 |
|   |   | 100 | 100 |

P: Pulverulent phase
F1: Film-forming polymer,
F2: Oils and Preservative

Preparation of Example 13 by Wet Process

The film-forming polymer (F1), the oil(s) and the preservative (F2), which form a liquid fatty phase, were heated and then mixed with 40 parts by weight of isoparaffine as an additional solvent. The components in the pulverulent phase (P) are then add to said mixture and mixed together so as to foam a slurry bulk mixture. The slurry was charged in to a pan, followed by being pressed at a pressure of 20 kgf/cm², aspirated and dried to form an eye shadow in the form of a pressed powder.

Preparation of the Comparative Example 2 by Dry Process

The components in the pulverulent phase (P) were mixed in a mixer. The film-forming polymer(s) (F1), the oil(s) and the preservative (F2), which forms a liquid fatty phase, were heated and mixed in a separate mixer. The both mixtures were mixed together to prepare a bulk mixture.

The bulk mixture was charged into a pan followed by being pressed at a pressure of 40 kgf/cm² to form an eye shadow in the form of a pressed powder.

[Evaluation]

(Sensory Evaluation)

The eye shadows according to Example 13 and Comparative Example 2 were compared in terms of long lasting cosmetic effects (coverage, smudge, and color change) for 5 hours by panelists under the conditions that the eye shadow of Example 13 was applied onto the half of the eyelids of each panelist, and the eye shadow of Comparative Example 2 was applied to the other half of the eyelids of each panelist, wherein the amount of the eye shadow applied to the each half of the face was the same. All of the panelist reported that the eye shadow according to Example 13 had an optimized long lasting effects than the eye shadow according to Comparative Example 2.

The invention claimed is:

1. A process for preparing a cosmetic powdery composition, in the form of a compact powder, the process comprising:
   mixing together to prepare a slurry comprising:
      an oil phase in an amount of at least about 20% by weight, relative to the total weight of the composition, wherein the oil phase comprises at least one non-volatile hydrocarbon oil in an amount of from 10% to 40% by weight relative to the total weight of the composition;
      a pulverulent phase in an amount of at least about 50% by weight, relative to the total weight of the composition;
      at least one hydrophobic film-forming polymer; and
      at least one additional solvent;
      wherein the weight ratio of the total oil phase to the total pulverulent phase ranges from about 20:80 to about 45:55;
      wherein the weight ratio of the total oil phase to the total amount of hydrophobic film-forming polymer ranges from about 98:2 to about 70:30,
   shaping the slurry in a container by compression and/or aspiration to prepare a cosmetic powdery composition, and
   drying the cosmetic powdery composition, after the step of shaping.

2. The process according to claim 1, wherein the at least one hydrophobic film-forming polymer is chosen from polyamide-silicone block polymers, block ethylenic polymers, vinyl polymers comprising at least one carbosiloxane dendrimer derivative, copolymers comprising carboxylate groups and polydimethylsiloxane groups, silicone resins, lipodispersible polymers in the form of a non-aqueous dispersion of polymer particles, olefin copolymers chosen from amorphous olefin copolymers or olefin copolymers with controlled and moderate crystallization, hydrocarbon-based resins having a number-average molecular weight of less than or equal to about 10000 g/mol, or mixtures thereof.

3. The process according to claim 1, wherein the at least one hydrophobic film-forming polymer comprises a polyamide-silicone block polymer comprising a polyamide-silicone block copolymer comprising at least one unit of formula (III) or (IV):

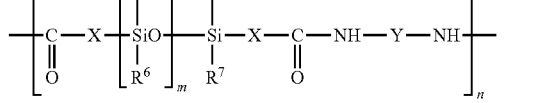

wherein:

6) $R^4$, $R^5$, $R^6$ and $R^7$, which may be identical or different, each represent a group chosen from:

linear, branched or cyclic, saturated or unsaturated, $C_1$ to $C_{40}$ hydrocarbon-based groups, optionally containing in their chain at least one oxygen, sulfur and/or nitrogen atom, and optionally being partially or totally substituted with fluorine atoms, $C_6$-$C_{10}$ aryl groups, optionally substituted with at least one $C_1$-$C_4$ alkyl group, polyorganosiloxane chains optionally containing at least one oxygen, sulfur and/or nitrogen atom, 7) the groups X, which may be identical or different, represent a linear or branched $C_1$-$C_{30}$ alkylenediyl group, optionally containing in its chain at least one oxygen and/or nitrogen atom;

8) Y is chosen from:

a saturated or unsaturated $C_1$ to $C_{50}$ linear or branched alkylene, arylene, cycloalkylene, alkylarylene or arylalkylene divalent group, which may comprise least one oxygen, sulfur and/or nitrogen atom, and/or may bear as substituent one of the following atoms or groups of atoms: fluorine, hydroxyl, $C_3$ to $C_8$ cycloalkyl, $C_1$ to $C_{40}$ alkyl, $C_5$ to $C_{10}$ aryl, phenyl optionally substituted with 1 to 3 $C_1$ to $C_3$ alkyl, $C_1$ to $C_3$ hydroxyalkyl or $C_1$ to $C_6$ aminoalkyl groups, or a group corresponding to the formula:

wherein:

T is chosen from:

a linear or branched, saturated or unsaturated, $C_3$-$C_{24}$ trivalent or tetravalent hydrocarbon-based group optionally substituted with a polyorganosiloxane chain, and optionally containing at least one atom chosen from O, N and S, or a trivalent atom chosen from N, P or Al, and $R^8$ is chosen from a linear or branched $C_1$-$C_{50}$ alkyl group or a polyorganosiloxane chain, optionally comprising at least one ester, amide, urethane, thiocarbamate, urea, thiourea and/or sulfonamide group, which may optionally be linked to another chain of the polymer;

9) n is an integer ranging from 2 to 500; and 10) m is an integer ranging from 50 to 1000.

4. The process according to claim 1, wherein the at least one hydrophobic film-forming polymer comprises a silicone resin chosen from polymethylsilsesquioxanes, siloxysilicate resins, trimethyl siloxysilicate resins, or mixtures thereof.

5. The process according to claim 1, wherein the at least one hydrophobic film-forming polymer comprises a block ethylenic polymer comprising a block ethylenic copolymer comprising:

at least a first block with a glass transition temperature (Tg) of greater than or equal to about 40° C. and being totally or partly derived from at least one first monomer, wherein the homopolymer prepared from the at least one first monomer has a glass transition temperature of greater than or equal to about 40° C.; and at least a second block with a glass transition temperature of less than or equal to about 20° C. and being derived totally or partly from at least one second monomer, wherein the homopolymer prepared from the at least one second monomer has a glass transition temperature of less than or equal to about 20° C., wherein the first block and the second block are connected together via a statistical intermediate segment comprising at least one of the first monomers of the first block and at least one of the second monomers of the second block, and wherein the block copolymer has a polydispersity index (I) of at least 2.

6. The process according to claim 5, wherein the block ethylenic copolymer is such that:

the first block is obtained from at least one acrylate monomer of formula $CH_2$=CH—$COOR_2$ in which $R_2$ is chosen from a $C_4$ to $C_{12}$ cycloalkyl group and from at least one methacrylate monomer of formula $CH_2$=C($CH_3$)—COOR'$_2$ in which R'$_2$ is chosen from a $C_4$ to $C_{12}$ cycloalkyl group, and the second block is obtained from at least a second monomer with a glass transition temperature of less than or equal to about 20° C. and from an additional monomer.

7. The process according to claim 1, wherein the at least one hydrophobic film-forming polymer comprises a vinyl polymer comprising at least one carbosiloxane dendrimer derivative comprising at least one carbosiloxane dendrimer-based unit and is the product of polymerization of:

(A) from about 0 to about 99.9 parts by weight of a vinyl monomer; and (B) from about 100 to about 0.1 parts by weight of a carbosiloxane dendrimer containing a radical-polymerizable organic group, represented by the formula:

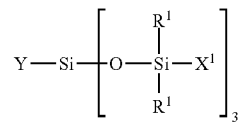

wherein:

Y is chosen from a radical-polymerizable organic group, $R^1$ is chosen from an aryl group or an alkyl group containing from 1 to 10 carbon atoms, and $X^i$ is chosen from a silylalkyl group which, when i=1, is represented by the formula:

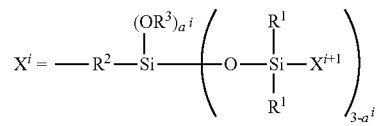

wherein:

$R^1$ is chosen from an aryl group or an alkyl group containing from 1 to 10 carbon atoms, $R^2$ is chosen from an alkylene group containing from 2 to 10 carbon atoms, $R^3$ is chosen from an alkyl group containing from 1 to 10 carbon atoms, $X^{i+1}$ is chosen from a hydrogen atom, an alkyl group containing from 1 to 10 carbon atoms, an aryl group, or the silylalkyl group defined above with i=i+1;

i is an integer from 1 to 10 that represents the generation of the said silylalkyl group, and $a^i$ is an integer from 0 to 3;

wherein the radical-polymerizable organic group Y contained in component (B) is chosen from the group formed by:
(1) an organic group that contains a methacrylic group or an acrylic group and that is chosen from the compounds represented by the formulae:

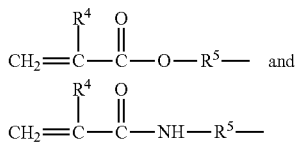

wherein:
$R^4$ is chosen from a hydrogen atom or an alkyl group, and
$R^5$ is chosen from an alkylene group containing from 1 to 10 carbon atoms; and
(2) an organic group containing a styryl group and that is represented by the formula:

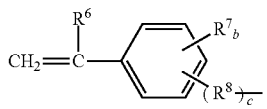

wherein:
$R^6$ is chosen from a hydrogen atom or an alkyl group,
$R^7$ is chosen from an alkyl group containing from 1 to 10 carbon atoms,
$R^8$ is chosen from an alkylene group containing from 1 to 10 carbon atoms,
b is an integer from 0 to 4, and
c is 0 or 1,
with the proviso that if c is 0, $-(R^8)_c-$ represents a bond.

8. The process according to claim 7, wherein the vinyl polymer comprising at least one carbosiloxane dendrimer derivative is an acrylate/polytrimethyl siloxymethacrylate copolymer.

9. The process according to claim 1, wherein the at least one hydrophobic film-forming polymer comprises a copolymer comprising carboxylate groups and polydimethylsiloxane groups chosen from copolymers of acrylic acid and of stearyl acrylate containing polydimethylsiloxane grafts; copolymers of stearyl methacrylate containing polydimethylsiloxane grafts; copolymers of acrylic acid and of stearyl methacrylate containing polydimethylsiloxane grafts; or copolymers of methyl methacrylate, butyl methacrylate, 2-ethylhexylacrylate and stearyl methacrylate containing polydimethylsiloxane grafts.

10. The process according to claim 1, wherein the at least one hydrophobic film-forming polymer comprises an amorphous olefin copolymer comprising at least one styrene block.

11. The process according to claim 1, wherein the at least one hydrophobic film-forming polymer comprises an amorphous olefin copolymer chosen from styrene-ethylene/butylene-styrene triblock copolymers, styrene-ethylene/butylene diblock copolymers, styrene-ethylene/isoprene-styrene triblock copolymers, styrene/ethylene-propylene diblock copolymers, styrene-ethylene/isoprene diblock copolymers, or mixtures thereof.

12. The process according to claim 1, wherein the at least one hydrophobic film-forming polymer comprises a hydrocarbon-based resin having a number-average molecular weight of less than or equal to 10,000 g/mol chosen from indene hydrocarbon-based resins.

13. The process according to claim 1, wherein the total amount of hydrophobic film-forming polymer is at least about 0.1% by weight, relative to the total weight of the composition.

14. The process according to claim 1, wherein the oil phase comprises at least one non-volatile silicone oil chosen from phenyl silicone oils and non-phenyl linear silicone oils, in an amount ranging from about 1% to about 20% by weight, relative to the total weight of the composition.

15. The process according to claim 1, wherein the non-volatile hydrocarbon-based oil is chosen from fatty esters represented by the formula RCOOR' wherein R denotes a $C_{1-29}$ fatty acid residue, and R' denotes $C_{2-30}$ hydrocarbon group, wherein the total amount of fatty esters ranges from 10% to 40% by weight, relative to the total weight of the composition.

16. The process according to claim 1, wherein the pulverulent phase comprises at least one non-spherical filler chosen from the group of talc, mica, silica, kaolin, sericite, calcinated talc, calcinated mica, calcinated sericite, synthetic mica, lauroyl lysine, metal soap, bismuth oxychloride, barium sulfate, boron nitride, calcium carbonate, magnesium carbonate, magnesium hydrogen carbonate, hydroxyapatite, or a mixture thereof.

17. The process according to claim 1, wherein the pulverulent phase comprises at least one pigment or at least one pearlescent pigment.

18. The process according to claim 1, wherein the mixing step comprises:
mixing the oil phase, the at least one film-forming polymer, and the pulverulent phase to form a mixture, and
mixing the at least one additional solvent with the mixture.

19. The process according to claim 1, wherein the mixing step comprises:
mixing the oil phase, the at least one film-forming polymer, and the at least one additional solvent to form a mixture, and
mixing the pulverulent phase with the mixture.

20. The process according to claim 1, wherein the additional solvent comprises a volatile solvent or a volatile organic solvent.

* * * * *